US012763168B2

(12) United States Patent
(10) Patent No.: US 12,763,168 B2
(45) Date of Patent: *Oct. 13, 2026

Mahajan et al.

(54) METHODS AND SYSTEMS FOR DETECTING CANCER VIA NUCLEIC ACID METHYLATION ANALYSIS

(71) Applicant: Freenome Holdings, Inc., South San Francisco, CA (US)

(72) Inventors: Shivani Mahajan, San Francisco, CA (US); Billie Gould, San Mateo, CA (US); Peter Ulz, Graz (AT)

(73) Assignee: Freenome Holdings, Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/163,174

(22) Filed: Feb. 1, 2023

(65) Prior Publication Data

US 2023/0178181 A1 Jun. 8, 2023

Related U.S. Application Data

(63) Continuation of application No. PCT/US2022/021662, filed on Mar. 24, 2022.

(60) Provisional application No. 63/166,641, filed on Mar. 26, 2021.

(51) Int. Cl.

| | |
|---|---|
| ***G16B 30/00*** | (2019.01) |
| ***C12Q 1/6886*** | (2018.01) |
| ***G16B 40/00*** | (2019.01) |
| ***G16B 40/20*** | (2019.01) |
| ***G16H 50/20*** | (2018.01) |

(52) U.S. Cl.

CPC .......... *G16B 30/00* (2019.02); *C12Q 1/6886* (2013.01); *G16B 40/00* (2019.02); *G16B 40/20* (2019.02); *G16H 50/20* (2018.01)

(58) Field of Classification Search

CPC ........ G16B 30/00; G16B 40/00; G16B 40/20; G16B 20/00; C12Q 1/6886; C12Q 2600/154; G16H 50/20

See application file for complete search history.

(56) References Cited

U.S. PATENT DOCUMENTS

| | | | |
|---|---|---|---|
| 5,786,146 | A | 7/1998 | Herman et al. |
| 7,270,960 | B2 | 9/2007 | Hellstrom et al. |
| 7,727,720 | B2 | 6/2010 | Dhallan |
| 7,754,429 | B2 | 7/2010 | Rigatti et al. |
| 8,168,385 | B2 | 5/2012 | Brenner |
| 8,318,433 | B2 | 11/2012 | Brenner |
| 9,040,239 | B1 | 5/2015 | Zheng et al. |
| 9,080,210 | B2 | 7/2015 | Van Eijk et al. |
| 9,447,452 | B2 | 9/2016 | Rao et al. |
| 10,295,540 | B1 | 5/2019 | Buturovic et al. |
| 10,337,053 | B2 | 7/2019 | Rao et al. |
| 10,443,091 | B2 | 10/2019 | Rao et al. |
| 10,533,213 | B2 | 1/2020 | Rao et al. |
| 10,731,204 | B2 | 8/2020 | Rao et al. |
| 10,731,223 | B2 | 8/2020 | Kennedy et al. |
| 10,767,216 | B2 | 9/2020 | Rao et al. |
| 10,774,373 | B2 | 9/2020 | Rao et al. |
| 10,978,175 | B2 | 4/2021 | Van Eijk et al. |
| 11,072,818 | B2 | 7/2021 | Rao et al. |
| 11,208,683 | B2 | 12/2021 | Rao et al. |
| 11,514,289 | B1 | 11/2022 | Otte et al. |
| 11,681,953 | B2 | 6/2023 | Drake et al. |
| 11,781,959 | B2 | 10/2023 | Delubac |
| 11,847,532 | B2 | 12/2023 | Drake et al. |
| 2006/0177837 | A1 | 8/2006 | Borozan et al. |
| 2008/0194413 | A1 | 8/2008 | Albert |

(Continued)

FOREIGN PATENT DOCUMENTS

| | | | |
|---|---|---|---|
| AU | 2006203948 | A1 | 7/2006 |
| CN | 101268367 | A | 9/2008 |

(Continued)

OTHER PUBLICATIONS

Chatterjee, S.; Iyer, A.; Avva, S.; Kollara, A.; Sankarasubbu, M. Convolutional Neural Networks in Classifying Cancer Through DNA Methylation. arXiv Jul. 24, 2018. http://arxiv.org/abs/1807.09617 (accessed Jul. 6, 2023).*

Khwaja, M.; Kalofonou, M.; Toumazou, C. A Deep Autoencoder System for Differentiation of Cancer Types Based on DNA Methylation State. arXiv Oct. 5, 2018. http://arxiv.org/abs/1810.01243 (accessed Jul. 6, 2023).*

Liu, B.; Liu, Y.; Pan, X.; Li, M.; Yang, S.; Li, S. C. DNA Methylation Markers for Pan-Cancer Prediction by Deep Learning. Genes 2019, 10 (10), 778:1-17.*

Xia, C.; Xiao, Y.; Wu, J.; Zhao, X.; Li, H. A Convolutional Neural Network Based Ensemble Method for Cancer Prediction Using DNA Methylation Data. In Proceedings of the 2019 11th International Conference on Machine Learning and Computing; ACM: Zhuhai China, 2019; pp. 191-196.*

(Continued)

*Primary Examiner* — Mary K Zeman
*Assistant Examiner* — Vy Rossi
(74) *Attorney, Agent, or Firm* — WILSON SONSINI GOODRICH & ROSATI

(57) ABSTRACT

The present disclosure provides methods and systems for screening or detecting a tumor or following disease progression that may be applied to cell-free nucleic acids, such as cell-free DNA. The method may use detection of methylation signals within a single sequencing read in identified genomic regions as input features to train a machine learning model and generate a classifier useful for stratifying populations of individuals. The method may comprise extracting DNA from a cell-free sample obtained from a subject, converting the DNA for methylation sequencing, generating sequencing reads, detecting proliferative cell disorder-associated signals in the sequencing information, and training a machine learning model to provide a discriminator capable of distinguishing groups in a subject population such as healthy, cancer, or distinguishing disease subtype or stage. The method may be used for, e.g., predicting, prognosticating, and/or monitoring response to treatment, tumor load, relapse, or cancer development.

7 Claims, 3 Drawing Sheets

(56) References Cited

U.S. PATENT DOCUMENTS

| | | | |
|---|---|---|---|
| 2008/0194414 | A1 | 8/2008 | Albert et al. |
| 2009/0221438 | A1 | 9/2009 | Kitzman et al. |
| 2010/0131286 | A1 | 5/2010 | Houlgatte et al. |
| 2010/0151471 | A1 | 6/2010 | Faham et al. |
| 2013/0022974 | A1 | 1/2013 | Chinnaiyan et al. |
| 2014/0234854 | A1 | 8/2014 | Blume et al. |
| 2014/0274767 | A1 | 9/2014 | Yegnasubramanian et al. |
| 2014/0365243 | A1 | 12/2014 | Varadan et al. |
| 2015/0218646 | A1 | 8/2015 | Haince et al. |
| 2015/0324527 | A1 | 11/2015 | Siegel et al. |
| 2016/0040246 | A1 | 2/2016 | Ahlquist et al. |
| 2016/0040248 | A1 | 2/2016 | Lehrer |
| 2016/0068915 | A1 | 3/2016 | Kennedy et al. |
| 2017/0091637 | A1 | 3/2017 | Chae et al. |
| 2017/0261509 | A1 | 9/2017 | Wang et al. |
| 2017/0277844 | A1 | 9/2017 | Apte et al. |
| 2018/0037953 | A1 | 2/2018 | Emerson et al. |
| 2018/0068083 | A1 | 3/2018 | Cohen et al. |
| 2018/0102187 | A1 | 4/2018 | Apte et al. |
| 2018/0119137 | A1 | 5/2018 | Matsuguchi et al. |
| 2018/0122508 | A1 | 5/2018 | Wilde et al. |
| 2018/0349548 | A1 | 12/2018 | Walsh et al. |
| 2018/0358132 | A1 | 12/2018 | Bagaev et al. |
| 2019/0196877 | A1 | 6/2019 | Biener et al. |
| 2019/0256924 | A1 | 8/2019 | Vogelstein et al. |
| 2019/0391151 | A1 | 12/2019 | Gatto et al. |
| 2020/0005899 | A1* | 1/2020 | Nicula .................. G16B 25/10 |
| 2020/0131582 | A1 | 4/2020 | Zhou et al. |
| 2020/0232894 | A1 | 7/2020 | Delubac |
| 2020/0377956 | A1 | 12/2020 | Vogelstein et al. |
| 2021/0010076 | A1 | 1/2021 | Delubac et al. |
| 2021/0017609 | A1 | 1/2021 | Gross et al. |
| 2021/0020314 | A1 | 1/2021 | Ehrich et al. |
| 2021/0057046 | A1 | 2/2021 | Liu et al. |
| 2021/0174958 | A1 | 6/2021 | Drake et al. |
| 2021/0210205 | A1 | 7/2021 | Drake et al. |
| 2021/0230684 | A1 | 7/2021 | Ariazi et al. |
| 2021/0272653 | A1 | 9/2021 | Ulz et al. |
| 2023/0101485 | A1 | 3/2023 | St. John et al. |
| 2023/0220492 | A1 | 7/2023 | St. John et al. |
| 2024/0084397 | A1 | 3/2024 | Mahajan et al. |
| 2026/0028680 | A1 | 1/2026 | St. John et al. |

FOREIGN PATENT DOCUMENTS

| | | | |
|---|---|---|---|
| CN | 104603292 | A | 5/2015 |
| CN | 105143465 | A | 12/2015 |
| EP | 0430402 | A2 | 6/1991 |
| EP | 3152333 | B1 | 9/2019 |
| JP | 2014522993 | A | 9/2014 |
| JP | 2017516504 | A | 6/2017 |
| JP | 2018508228 | A | 3/2018 |
| WO | WO-2006074360 | A2 | 7/2006 |
| WO | WO-2013022995 | A2 | 2/2013 |
| WO | WO-2014012176 | A1 | 1/2014 |
| WO | WO-2015187823 | A2 | 12/2015 |
| WO | WO-2016115530 | A1 | 7/2016 |
| WO | WO-2016119190 | A1 | 8/2016 |
| WO | WO2017062867 | A1 | 4/2017 |
| WO | WO-2018009723 | A1 | 1/2018 |
| WO | WO-2018013865 | A1 | 1/2018 |
| WO | WO-2019051484 | A1 | 3/2019 |
| WO | WO2019060716 | A1 | 3/2019 |
| WO | WO-2019067092 | A1 | 4/2019 |
| WO | WO-2019071161 | A1 | 4/2019 |
| WO | WO-2019100024 | A1 | 5/2019 |
| WO | WO-2019147663 | A1 | 8/2019 |
| WO | WO-2019191319 | A1 | 10/2019 |
| WO | WO-2019191649 | A1 | 10/2019 |
| WO | WO-2019195268 | A2 | 10/2019 |
| WO | WO-2019200410 | A1 | 10/2019 |
| WO | WO-2020076772 | A1 | 4/2020 |
| WO | WO-2020243609 | A1 | 12/2020 |
| WO | WO-2021202351 | A1 | 10/2021 |
| WO | WO-2021222220 | A2 | 11/2021 |
| WO | WO-2022076237 | A1 | 4/2022 |
| WO | WO-2022140116 | A1 | 6/2022 |
| WO | WO-2022204358 | A1 | 9/2022 |
| WO | WO-2022261192 | A1 | 12/2022 |
| WO | WO-2023003851 | A1 | 1/2023 |
| WO | WO-2023147472 | A1 | 8/2023 |
| WO | WO-2023183468 | A2 | 9/2023 |
| WO | WO2023235878 | A2 | 12/2023 |
| WO | WO2023244983 | A1 | 12/2023 |
| WO | WO2023250441 | A2 | 12/2023 |

OTHER PUBLICATIONS

Zheng, C.; Xu, R. Predicting Cancer Origins with a DNA Methylation-Based Deep Neural Network Model. PLoS ONE 2020, 15 (5), e0226461:1-17.*

Illumina, Inc. Infinium® HumanMethylation450 BeadChip. Product data sheet. 2012.*

Illumina Inc. Comprehensive DNA methylation analysis on the Illumina Infinium assay platform, 2010 Application Notes: Epigenetic Analysis, p. 1-6. (Year: 2010).* https://support.illumina.com/content/dam/illumina-support/documents/downloads/productfiles/humanmethylation27/productsupportfiles/illumina_humanmethylation27_content.xlsx; first 20 pages of 2086. (Year: 2010).*

Asmus et al. Simultaneous Targeted Methylation Sequencing (sTM-Seq). Curr Protoc Hum Genet 101(1):e81, pp. 1-19 doi:10.1002/cphg.81 (2019).

Booth et al. Quantitative Sequencing of 5-Methylcytosine and 5-Hydroxymethylcytosine at Single-Base Resolution. Science 336(6083):934-937 (2012).

Fay et al. Confidence intervals of the Mann-Whitney parameter that are compatible with the Wilcoxon-Mann-Whitney test. Stat Med 37(27):3991-4006 doi:10.1002/sim.7890 (2018).

Frommer et al. A genomic sequencing protocol that yields a positive display of 5-methylcytosine residues in individual DNA strands. PNAS USA 89:1827-1831 (1992).

Geneva: World Health Organization: WHO list of priority medical devices for cancer management, WHO Medical device technical series. ISBN: 978-92-4-156546-2, License: CC BY-NC-SA 3.0 IGO, pp. 1-252 (2017).

Golub et al. Molecular classification of cancer: Class discovery and class prediction by gene expression monitoring, Science, American Association for the Advancement of Science, 286:5439 (Oct. 15, 1999).

Herman, J.G. et al. Methylation-Specific PCR: A Novel PCR Assay for Methylation Status of CpG Islands. Proceedings of the National Academy of Science USA 93:9821-9826, Sep. 1996.

Kourou et al. Machine learning applications in cancer prognosis and prediction. Comput Struct Biotechnol J.13:8-17 (2014).

Liu et al. An individualized predictor of health and disease using paired reference and target samples. BMC Bioinformatics 17:47 [1-15] (2016).

Liu et al. Bisulfite-Free Direct Detection of 5-Methylcytosine and 5-Hydroxymethylcytosine at Base Resolution. Nature Biotechnology 37(4):424-429 (2019).

Manghnani et al. METCC: METric learning for Confounder Control Making distance matter in high dimensional biological analysis. arXiv:1812.03188v1 [cs.LG] [1-10] (2018).

PCT/US2022/021662 International Search Report and Written Opinion dated Aug. 2, 2022.

Schutsky et al. Nondestructive, Base-Resolution Sequencing of 5-Hydroxymethylcytosine Using a DNA Deaminase. Nature Biotechnology 36(11):1083-1090 (2018).

Singh, et al. Gene expression correlates of clinical prostate cancer behavior. Cancer Cell. vol. 1, pp. 203-209 (2002).

Wan et al. Machine learning enables detection of early-stage colorectal cancer by whole-genome sequencing of plasma cell-free DNA. bioRxiv prePrint URL:https://doi.org/10.1101/478065 [1-22] (2018).

Wolpin et al. Systemic treatment of colorectal cancer. Gastroenterology 134(5):1296-1310 doi:10.1053/j.gastro.2008.02.098 (2008).

Yu et al. Tet-assisted bisulfite sequencing of 5-hydroxymethylcytosine. Nat Protoc. 7(12):2159-2170 doi:10.1038/nprot.2012.137 (2012).

(56) References Cited

OTHER PUBLICATIONS

Zhang et al. Tet-mediated covalent labelling of 5-methylcytosine for its genome-wide detection and sequencing, Nat Commun. 2013;4:1517.
Ahlquist et al., The stool DNA test is more accurate than the plasma septin 9 test in detecting colorectal neoplasia. Clin Gastroenterol Hepatol. 10(3):272-7.e1 pp. 1-13 (2012).
Church et al., Prospective evaluation of methylated SEPT9 in plasma for detection of asymptomatic colorectal cancer. Gut. 63(2):317-325 (2014).
Cohen et al., Detection and localization of surgically resectable cancers with a multi-analyte blood test. Science. 359(6378):926-930 (2018).
Friedland et al., Development and clinical validation of a blood test for early detection of colorectal adenomas and cancer for screening and postpolypectomy surveillance. Gastro Hep Adv. 1(2): 223-230 (2022).
Glaab et al., Using rule-based machine learning for candidate disease gene prioritization and sample classification of cancer gene expression data. PLoS One. 7(7):e39932 pp. 1-18 (2012).
Golub et al.; Molecular classification of cancer: class discovery and class prediction by gene expression monitoring. Science. 286(5439):531-537 (1999).
Hasan et al., Classification of cancer cells using computational analysis of dynamic morphology. Comput Methods Programs Biomed. 156:105-112 (2018).
Holmila et al., Targeted deep sequencing of plasma circulating cell-free DNA reveals Vimentin and Fibulin 1 as potential epigenetic biomarkers for hepatocellular carcinoma. PLoS One. 12(3):e0174265 pp. 1-15 (2017).
Huang et al., Applications of support vector machine (SVM) learning in cancer genomics. Cancer Genomics Proteomics. 15(1):41-51 (2018).
Ko et al., Combining machine learning and nanofluidic technology to diagnose pancreatic cancer using exosomes. ACS Nano. 11(11):11182-11193 (2017).
Libbrecht et al., Machine learning applications in genetics and genomics. Nat Rev Genet 16(6):321-332 (2015).
Ng et al., Differential expression of microRNAs in plasma of patients with colorectal cancer: a potential marker for colorectal cancer screening. Gut. 58(10):1375-1381 (2009).
PCT/US2022/021662 Invitation to Pay Additional Fees dated Jun. 9, 2022.
Potter et al., Validation of a real-time PCR-based qualitative assay for the detection of methylated SEPT9 DNA in human plasma. Clin Chem. 60(9):1183-1191 (2014).
Warren et al., Septin 9 methylated DNA is a sensitive and specific blood test for colorectal cancer. BMC Med. 9:133 pp. 1-9 (2011).
Way et al., A machine learning classifier trained on cancer transcriptomes detects NF1 inactivation signal in glioblastoma. BMC Genomics. 18(1):127 pp. 1-11 (2017).
Zhang et al., Predicting essential genes and proteins based on machine learning and network topological features: A comprehensive review. Front Physiol. 7:75 pp. 1-11 (2016).
Cohen et al., Supplementary material for: Detection and localization of surgically resectable cancers with a multi-analyte blood test. Science 359(6378): 926-930 (2018). Available at https://www.science.org/doi/10.1126/science.aar3247#supplementary-materials.
Klett et al., Robust prediction of gene regulation in colorectal cancer tissues from DNA methylation profiles. Epigenetics. 13(4):386-397 (2018).
Li et al., Detection of colorectal cancer in circulating cell-free DNA by methylated CpG tandem amplification and sequencing. Clin Chem. 65(7):916-926 (2019).
Prescott et al., Pooled sequencing of 531 genes in inflammatory bowel disease identifies an associated rare variant in BTNL2 and implicates other immune related genes. PLoS Genet. 11(2):e1004955, pp. 1-19 (2015).
U.S. Appl. No. 18/163,174 Final Office Action dated Oct. 16, 2023.
EP21780407.9 Extended European Search Report dated Jun. 6, 2024.
Li, et al., MethPrimer: designing primers for methylation PCRs. Bioinformatics. vol. 18(11):1427-1431 (2002).
PCT/US2022/024604 International Preliminary Report on Patentability dated Sep. 29, 2022.
U.S. Appl. No. 18/163,138 Final Office Action dated Dec. 12, 2023.
U.S. Appl. No. 18/163,138 Office Action dated Aug. 10, 2023.
U.S. Appl. No. 18/163,138 Office Action Jul. 5, 2024.
Yagi, et al., Three DNA methylation epigenotypes in human colorectal cancer. Clin Cancer Res. 16(1):21-33 (2010).
Adler, Andreas. et al. Improving compliance to colorectal cancer screening using blood and stool based tests in patients refusing screening colonoscopy in Germany. BMC Gastroenterology 14(1):183, 1-8 (2014).
Albertson, D G. Localization of the ribosomal genes in Caenorhabditis elegans chromosomes by in situ hybridization using biotin-labeled probes. EMBO J 3(6):1227-1234 (1984).
Aravanis, Alexander M. et al. Next-Generation Sequencing of Circulating Tumor DNA for Early Cancer Detection. Cell 168(4):571-574 (2017).
Barringer, K J. et al. Blunt-end and single-strand ligations by *Escherichia coli* ligase: influence on an in vitro amplification scheme. Gene 89(1):117-122 (1990).
Best, Myron G. et al. RNA-Seq of Tumor-Educated Platelets Enables Blood-Based Pan-Cancer, Multiclass, and Molecular Pathway Cancer Diagnostics. Cancer Cell 28(5):666-676 (2015).
Bettegowda, Chetan. et al. Detection of Circulating Tumor DNA in Early- and Late-Stage Human Malignancies. Science translational medicine 6(224):1-25 (2014).
Bishop, Neural Networks for Pattern Recognition, Clarendon Press, Oxford 1995.
Breiman, Leo. Random Forests. Machine Learning 45(1):5-32 (2001).
Choo. Methods in Molecular Biology—In Situ Hybridization Protocols. vol. 33, Humana Press Inc., New Jersey. (1994).
CN202180039398.8 Office Action with Search Report dated Oct. 25, 2024, and a partial English translation.
Duda et al. Pattern Classification, 2.sup.nd ed., john Wiley, New York 2001.
Dudoit, Sandrine. et al. Comparison of Discrimination Methods for the Classification of Tumors Using Gene Expression Data. Journal of the American Statistical Association 97(457):77-87 (2002).
EP Serial No. 22776625.0 Partial Search Report dated Jan. 27, 2025.
Ernst, Jason. et al. Mapping and analysis of chromatin state dynamics in nine human cell types. Nature 473(7345):43-49 (2011).
Ginzonger, D G. et al. Measurement of DNA Copy Number at Microsatellite Loci Using Quantitative PCR Analysis. Cancer Research 60:5405-5409 (2000).
Guatelli. J C. et al. Isothermal, in vitro amplification of nucleic acids by a multienzyme reaction modeled after retroviral replication. Proc Natl Acad. Sci. 87(5):1874-1878 (1990).
Hansen, Kasper Daniel, et al. Increased Methylation Variation in Epigenetic Domains Across Cancer Types. Nature Genetics 43(8):768-775 (2011).
Haque, Imran S. et al. Challenges in using ctDNA to achieve early detection of cancer. BioRxiv:237578, 1-20 (2017).
Hastie, Trevor. et al. The Elements of Statistical Learning, Springer, New York 2001.
Innis et al. PCR Protocols: A Guide to Methods and Applications. Eds. Academic Press. 1990:v-x (Table of Contents).
Joseph, Djenaba A. et al. Use of Colorectal Cancer Screening Tests by State. Prev Chronic Dis 15:E80, 1-3 (2018).
JP2020-556286 Office action dated Apr. 25, 2023, and an English Translation.
Kallioniemi, O P. et al. ERBB2 amplification in breast cancer analyzed by fluorescence in situ hybridization. Proc Natl Acad Sci U S A 89(12):5321-5325 (1992).
Kwoh, D Y. et al. Transcription-based amplification system and detection of amplified human immunodeficiency virus type 1 with a bead-based sandwich hybridization format. Proc Natl Acad Sci 86(4):1173-1177 (1989).
Landegren, U. et al. A Ligase-mediated Gene Detection Technique. Science 241(4869):1077-1080 (1988).

(56) References Cited

OTHER PUBLICATIONS

Lim, S Y. et al. Liquid biomarkers in melanoma: detection and discovery. Molecular cancer 17(8):1-14 (2018).
Liu, L. et al. Targeted methylation sequencing of plasma cell-free DNA for cancer detection and classification. Annals of oncology 29(6):1445-1453 (2018).
Locke, Warwick J. et al. DNA Methylation Cancer Biomarkers: Translation to the Clinic. Frontiers in genetics 10:1150, 1-22 (2019).
Merker, Jason D. et al. Circulating Tumor DNA Analysis in Patients With Cancer: American Society of Clinical Oncology and College of American Pathologists Joint Review. J Clin Oncol 36(16):1631-1641 (2018).
Mostafavi, Sara. et al. Normalizing RNA-sequencing data by modeling hidden covariates with prior knowledge. PLoS One 8(7):e68141, 1-10 (2013).
Nguyen, Danh V, and David M Rocke. Tumor classification by partial least squares using microarray gene expression data. Bioinformatics 18(1):39-50 (2002).
O'Reilly, Julie-Ann, et al. Diagnostic potential of zinc finger protein-specific autoantibodies and associated linear B-cell epitopes in colorectal cancer. PloS one 10.4: e0123469. (2015).
Pauli, Chantal. et al. Personalized In Vitro and In Vivo Cancer Models to Guide Precision Medicine. Cancer Discov 7(5):462-477 (2017).
Phallen, Jillian. et al. Direct Detection of Early-stage Cancers Using Circulating Tumor DNA. Science Translational Medicine 9(403):eaan2415, 1-13 (2017).
Pinkel, D. et al. Fluorescence in situ hybridization with human chromosome-specific libraries: detection of trisomy 21 and translocations of chromosome 4. Proc Natl Acad Sci U S A 85(23):9138-9142 (1988).
Pinkel, D. et al. High resolution analysis of DNA copy number variation using comparative genomic hybridization to microarrays. Nat Genet 20:207-211 (1998).
Sabatino, Susan A. et al. Cancer screening test use—United States, 2013. MMWR Morb Mortal Wkly Rep 64(17):464-468 (2015).
Scholkopf, Bernhard, et al. Learning with Kernels, MIT Press, Cambridge. (2002).
SG11202009696W written opinion dated Aug. 4, 2022.
Somiari, Richard. et al. A Low-density Antigen Array for Detection of Disease-associated Autoantibodies in Human Plasma. Cancer Genomics Proteomics 13(1):13-19 (2016).
StÅhle, Lars, et al. Partial least squares analysis with cross-validation for the two-class problem: a Monte Carlo study. Journal of chemometrics, 1.3: 185-196. (1987).
Tibshirani, Robert. et al. Diagnosis of multiple cancer types by shrunken centroids of gene expression. Proc Natl Acad Sci U S A 99(10):6567-6572 (2002).
U.S. Appl. No. 18/163,138 Office Action dated Jan. 10, 2025.
Vandeginste, et al., Handbook of Chemometrics and Qualimetrics, Part B, Elsevier, Amsterdam 1998.
Wold, Svante. Pattern recognition by means of disjoint principal components models. Pattern recognition 8.3: 127-139. (1976).
Wu, Dan Y, and R. Bruce Wallace. The Ligation Amplification Reaction (LAR)—amplification of Specific DNA Sequences Using Sequential Rounds of Template-dependent Ligation. Genomics 4(4):560-569 (1989).
CN202180039398.8 Office Action dated May 10, 2025, and an English translation.
EP22776625 Extended European Search Report dated Apr. 17, 2025.
JP Serial No. 2022-559477 Office Action dated May 8, 2025.
U.S. Appl. No. 18/163,138 Notice of Allowance dated May 21, 2025.
CN202180039398.8 Office Action dated Jul. 14, 2025, and an English translation.
Guinney, Justin. et al. The consensus molecular subtypes of colorectal cancer. Nature medicine 21(11):1350-1356 (2015).
JP2022-559477 Office Action dated Nov. 17, 2025, and an English translation.
JP2023-559736 Office Action dated Jan. 13, 2026, and an English translation.
Toronen, Petri. et al. Analysis of gene expression data using self-organizing maps. FEBS Letters 451(2):142-146 (1991).
U.S. Appl. No. 17/954,576 Office Action dated Jun. 23, 2025.
Friedland et al.: Development and Clinical Validation of a blood test for early detection of colorectal adenomas and cancer. Abstract 32305, Poster Asco Gi Meeting [1-1] (2021).
SG11202253666G Search Report and Written Opinion dated Feb. 10, 2026.
Wide Coverage by Humanmethylation450 Beadchip Using Two Types of Infinium Chemistry, Illumina [online], 2013. Retrieved from https://jp.support.illumina.com/content/dam/illumina-marketing/apac/japan/documents/pdf/technote_hm450_data_analysis_optimization-J.pdf.

* cited by examiner

Heatmap showing clustering of beta values from the regions identified from the analysis. COAD and READ cluster together. LUSC (lung squamous carcinoma) and LUAD (lung adenocarcinoma) form largely two independent groups with a few samples that overlap.

Total region size: ~2.2 Mb

METHODS AND SYSTEMS FOR DETECTING CANCER VIA NUCLEIC ACID METHYLATION ANALYSIS

CROSS-REFERENCE

This application is a continuation of International Patent Application No. PCT/US2022/021662, filed Mar. 24, 2022, which claims the benefit of U.S. Provisional Patent Application No. 63/166,641, filed on Mar. 26, 2021, the contents of each of which are incorporated by reference herein.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BACKGROUND

The present disclosure relates generally to cancer detection and disease monitoring. More particularly, the field relates to cancer-related DNA methylation detection and disease monitoring in early-stage cancer. Cancer screening and monitoring may help to improve outcomes over the past few decades because early detection leads to a better outcome as the cancer may be eliminated before having the opportunity to spread.

A primary issue for any screening tool may be the compromise between false positive and false negative results (or specificity and sensitivity) which lead to unnecessary investigations in the former case, and ineffectiveness in the latter case. An ideal test may be one that has a high Positive Predictive Value (PPV), minimizing unnecessary investigations but detecting the vast majority of cancers. Another key factor is "detection sensitivity". Distinct from test sensitivity, detection sensitivity is the lower limits of detection with respect to the size of the tumor. Unfortunately, waiting for a tumor to grow large enough to release circulating tumor markers at levels necessary for detection may contradict the goal of treating a tumor at the early stages where treatments are most effective. Hence, there is a need for effective blood-based screens for early-stage cancer based on circulating analytes.

SUMMARY

The present disclosure provides methods and systems directed to methylation profiling of genes associated with cell proliferative disorder and cancer detection, and disease progression. Further provided are methods and systems directed to methylation profiling of genes associated with lung, colon, liver, ovarian, pancreatic, prostate, rectal, and breast cell proliferative disorder detection and disease progression.

In an aspect, the present disclosure provides a methylation signature panel characteristic of at least two cell proliferative disorders comprising: six or more methylated genomic regions selected from the group consisting of Table 1, wherein the one or more regions are more methylated in a biological sample from an subject having a cell proliferative disorder or cell proliferative disorder subtype and are less methylated in normal tissues and normal blood cells in an subject not having a cell proliferative disorder.

In some embodiments, the biological sample comprises a nucleic acid, DNA, RNA, or cell-free nucleic acid (cfDNA or cfRNA).

In some embodiments, the genomic region is a non-coding region, a coding region, or a non-transcribed or regulator region.

In some embodiments, the signature panel comprises increased methylation in 6 or more, or 12 or more genomic regions in Table 1.

In some embodiments, the signature panel comprises increased methylation in six or more methylated genomic regions in Table 1 that are associated with a type of cancer.

In some embodiments, the biological sample obtained from the subject is selected from the group consisting of body fluids, stool, colonic effluent, urine, blood plasma, blood serum, whole blood, isolated blood cells, cells isolated from the blood, and combinations thereof.

In some embodiments, the cell proliferative disorder is selected from colorectal, prostate, lung, breast, pancreatic, ovarian, uterine, liver, esophagus, stomach, or thyroid cell proliferation.

In some embodiments, the cell proliferative disorder is selected from colon adenocarcinoma, liver hepatocellular carcinoma, lung adenocarcinoma, lung squamous cell carcinoma, ovarian serious cystadenocarcinoma, pancreatic adenocarcinoma, prostate adenocarcinoma, and rectum adenocarcinoma.

In some embodiments, the cell proliferative disorder is selected from stage 1 cancer, stage 2 cancer, stage 3 cancer, or stage 4 cancer.

In some embodiments, the signature panel comprises three or more methylated genomic regions in Table 1, four or more methylated genomic regions in Table 1, five or more methylated genomic regions in Table 1, six or more methylated genomic regions in Table 1, seven or more methylated genomic regions in Table 1, eight or more methylated genomic regions in Table 1, nine or more methylated genomic regions in Table 1, ten or more methylated genomic regions in Table 1, eleven or more methylated genomic regions in Table 1, twelve or more methylated genomic regions in Table 1, or thirteen or more methylated genomic regions in Table 1.

In an aspect, the present disclosure provides a methylation signature panel characteristic of a tissue of origin for at least two cell proliferative disorders comprising: two or more methylated genomic region signature panels selected from the group consisting of methylated genomic regions in Tables 2 to 17, wherein the genomic regions are more methylated in a biological sample from an subject having a cell proliferative disorder or cell proliferative disorder subtype, and are less methylated in normal tissues and normal blood cells in an subject not having a cell proliferative disorder.

In some embodiments, the biological sample is a nucleic acid, DNA, RNA, or cell-free nucleic acid (cfDNA or cfRNA).

In some embodiments, the genomic region is a non-coding region, a coding region, or a non-transcribed or regulator region.

In some embodiments, the signature panel comprises increased methylation in 6 or more, 12 or more genomic regions in Tables 2 to 17.

In some embodiments, the signature panel comprises increased methylation in six or more methylated genomic regions in Tables 2 to 17 that are associated with cancer type and tumor tissue of origin.

In some embodiments, the biological sample obtained from the subject is selected from the group consisting of body fluids, stool, colonic effluent, urine, blood plasma, blood serum, whole blood, isolated blood cells, cells isolated from the blood, and combinations thereof.

In some embodiments, the cell proliferative disorder is selected from colorectal, prostate, lung, breast, pancreatic, ovarian, uterine, liver, esophagus, stomach or thyroid cell proliferation. In some embodiments, the cell proliferative disorder is selected from colon adenocarcinoma, liver hepatocellular carcinoma, lung adenocarcinoma, lung squamous cell carcinoma, ovarian serious cystadenocarcinoma, pancreatic adenocarcinoma, prostate adenocarcinoma, and rectum adenocarcinoma.

In some embodiments, the cell proliferative disorder is selected from stage 1 cancer, stage 2 cancer, stage 3 cancer, or stage 4 cancer.

In some embodiments, the signature panel comprises three or more methylated genomic regions in Tables 2 to 17, four or more methylated genomic regions in Tables 2 to 17, five or more methylated genomic regions in Tables 2 to 17, six or more methylated genomic regions in Tables 2 to 17, seven or more methylated genomic regions in Tables 2 to 17, eight or more methylated genomic regions in Tables 2 to 17, nine or more methylated genomic regions in Tables 2 to 17, ten or more methylated genomic regions in Tables 2 to 17, eleven or more methylated genomic regions in Tables 2 to 17, twelve or more methylated genomic regions in Tables 2 to 17, or thirteen or more methylated genomic regions in Tables 2 to 17.

In one embodiment, the at least two cell proliferative disorders comprise a combination selected from: colorectal cancer and prostate cancer; colorectal cancer and lung cancer; colorectal cancer and breast cancer; colorectal cancer and liver cancer; colorectal cancer and ovarian cancer; colorectal cancer and pancreatic cancer; prostate cancer and lung cancer; prostate cancer and breast cancer; prostate cancer and liver cancer; prostate cancer and ovarian cancer; prostate cancer and pancreatic cancer; lung cancer and breast cancer; lung cancer and liver cancer; lung cancer and ovarian cancer; lung cancer and pancreatic cancer; breast cancer and liver cancer; breast cancer and ovarian cancer; breast cancer and pancreatic cancer; liver cancer and ovarian cancer; liver cancer and pancreatic cancer; ovarian cancer and pancreatic cancer; colorectal cancer, prostate cancer and lung cancer; colorectal cancer, prostate cancer and breast cancer; colorectal cancer, prostate cancer and liver cancer; colorectal cancer, prostate cancer and ovarian cancer; colorectal cancer, prostate cancer and pancreatic cancer; colorectal cancer, lung cancer and breast cancer; colorectal cancer, lung cancer and liver cancer; colorectal cancer, lung cancer and ovarian cancer; colorectal cancer, lung cancer and pancreatic cancer; colorectal cancer, breast cancer and liver cancer; colorectal cancer, breast cancer and ovarian cancer; colorectal cancer, breast cancer and pancreatic cancer; prostate cancer, liver cancer and ovarian cancer; prostate cancer, liver cancer and pancreatic cancer; prostate cancer, ovarian cancer and pancreatic cancer; and colorectal cancer, prostate cancer, lung cancer, and breast cancer.

In various embodiments, the panel of predetermined methylated genomic regions associated with colorectal cancer tissue of origin is selected from Tables 2, 3, or 4.

In various embodiments, the panel of predetermined methylated genomic regions associated with liver cancer tissue of origin is selected from Tables 5, 6, or 7.

In various embodiments, the panel of predetermined methylated genomic regions associated with lung cancer tissue of origin is selected from Tables 8 or 9.

In various embodiments, the panel of predetermined methylated genomic regions associated with ovarian cancer tissue of origin is selected from Tables 10, 11, or 12.

In various embodiments, the panel of predetermined methylated genomic regions associated with pancreatic cancer tissue of origin is selected from Tables 13 or 14

In various embodiments, the panel of predetermined methylated genomic regions associated with prostate cancer tissue of origin is selected from Tables 15, 16, or 17.

In an aspect, the present disclosure provides a machine learning classifier trained on a panel of predetermined methylated genomic regions associated with 2 or more cancer types wherein the methylated genomic regions are selected from a) Table 1 and/or b) Tables 2-17 and combinations thereof.

In another aspect, the present disclosure provides a machine learning classifier capable of distinguishing a population of healthy subjects from subjects with a cell proliferative disorders, comprising:

a) sets of measured values representative of differentially-methylated genomic regions of Tables 1-17 associated with 2 or more cell proliferative disorders, where the measured values are obtained from methylation sequencing data from healthy subjects and subjects having a cell proliferative disorder,
b) wherein the measured values are used to generate a set of features corresponding to properties of the differentially-methylated genomic regions and where the features are analyzed using a machine learning or statistical model,
c) wherein the model provides a feature vector useful as a classifier capable of distinguishing a population of healthy subjects from subjects having a cell proliferative disorder.

In one embodiment, the sets of measured values describe characteristics of the methylated regions selected from the group consisting of: base wise methylation percent for CpG, CHG, CHH, conversion efficiency (100−mean methylation percent for CHH), hypomethylated blocks, methylation levels (global mean methylation for CPG, CHH, CHG, fragment length, fragment midpoint, and methylation levels in one or more genomic regions such as chrM, LINE1, or ALU), number of methylated CpGs per fragment, fraction of CpG methylation to total CpG per fragment, fraction of CpG methylation to total CpG per region, fraction of CpG methylation to total CpG in panel, dinucleotide coverage (normalized coverage of dinucleotide), evenness of coverage (unique CpG sites at 1× and 10× mean genomic coverage (for S4 runs), mean CpG coverage (depth) globally, and mean coverage at CpG islands (CGI), CGI shelves, CGI shores.

In some embodiments, the panel comprises part of a trained machine learning classifier to classify a subject as having cancer and/or localizing tissue of origin of a tumor in the subject.

In some embodiments, a machine learning model comprising the classifier is loaded into a memory of a computer system, the machine learning model trained using training vectors obtained from training biological samples, a first subset of the training biological samples identified as having a cell proliferative disorder and a second subset of the training biological samples identified as not having a cell proliferative disorder.

In an aspect, the present disclosure provides a machine learning classifier trained on a panel of predetermined methylated genomic regions associated with 2 or more types of cell proliferative disorder, and having pre-selected sensitivity and specificity for the different types of cell proliferative disorder to be detected using the panel.

In various embodiments, the different types of cell proliferative disorders are selected from colorectal cancer, breast cancer, ovarian cancer, prostate cancer, lung cancer, pancreatic cancer, uterine cancer, liver cancer, esophagus cancer, stomach cancer, thyroid cancer, or bladder cancer.

In one embodiment, the machine learning classifier is tailored to provide pre-selected sensitivity and specificity for the different types of cell proliferative disorder to be detected depending on needs of cancer diagnosis and confirmatory diagnosis for two or more cancers selected from colorectal cancer, breast cancer, ovarian cancer, prostate cancer, lung cancer, pancreatic cancer, uterine cancer, liver cancer, esophagus cancer, stomach cancer, thyroid cancer, or bladder cancer, or combinations thereof, wherein the pre-selected sensitivity for a colorectal cancer associated classification panel is at least 70% sensitivity; the pre-selected specificity for a breast cancer associated classification panel is at least 70% specificity; the pre-selected specificity for an ovarian cancer associated classification panel is at least 90% specificity; the pre-selected specificity for a prostate cancer associated classification panel is at least 70% specificity; the pre-selected specificity for a lung cancer associated classification panel is at least 70% specificity; the pre-selected specificity for a pancreatic cancer associated classification panel is at least 90% specificity; the pre-selected specificity for a uterine cancer associated classification panel is at least 90% specificity; the pre-selected sensitivity for a liver cancer associated classification panel is at least 70% sensitivity; the pre-selected sensitivity for an esophagus cancer associated classification panel is at least 70% sensitivity; the pre-selected sensitivity for a stomach cancer associated classification panel is at least 70% sensitivity; the pre-selected specificity for a thyroid cancer associated classification panel is at least 70% specificity; and the pre-selected sensitivity for a bladder cancer associated classification panel is at least 70% sensitivity selected based on which cancer types are detected by the classification model.

In an aspect, the present disclosure provides a method for determining a methylation profile of a cfDNA sample by obtaining, converting, sequencing cfDNA in a sample with a preselected panel of genomic regions associated with the presence of 2 or more cancer types and calculating a methylation profile of cfDNA corresponding to the preselected panel of genomic regions.

In an aspect, the present disclosure provides a method for determining a methylation profile of a cell-free deoxyribonucleic acid (cfDNA) sample from a subject, comprising:

a) providing conditions capable of converting unmethylated cytosines to uracils in nucleic acid molecules of the cfDNA sample to produce a plurality of converted nucleic acids;
b) contacting the plurality of converted nucleic acids with nucleic acid probes complementary to a pre-identified methylation signature panel of at least two differentially methylated regions selected from the group consisting of differentially methylated regions in Tables 1-17 to enrich for sequences corresponding to the signature panel;
c) determining nucleic acid sequences of the plurality of converted nucleic acid molecules; and
d) aligning the nucleic acid sequences of the plurality of converted nucleic acid molecules to a reference nucleic acid sequence, thereby determining the methylation profile of the subject.

In another aspect, the present disclosure provides a method for determining a methylation profile of a cfDNA sample from a subject comprising:

a) providing conditions capable of converting unmethylated cytosines to uracils in nucleic acid molecules of a cfDNA sample to produce a plurality of converted nucleic acids;
b) amplifying converted nucleic acids with polymerase chain reaction;
c) probing the converted nucleic acids with nucleic acid probes complementary to a pre-identified methylation signature panel of at least two differentially methylated regions selected from Tables 1-17 to enrich for sequences corresponding to the signature panel;
d) determining the nucleic acid sequence of the converted nucleic acid molecules at a depth of greater than 5000×, and
e) aligning the nucleic acid sequence of the converted nucleic acid molecules to a reference nucleic acid sequence for the pre-identified panel of CpG loci, to determine the methylation profile of the subject.

In some embodiments, a nucleic acid sequencing library is prepared before the amplification.

In some embodiments, the methylation profile is associated with a cell proliferative disorder and provides classification of a subject as having a cell proliferative disorder.

In some embodiments, a nucleic acid adapter comprising a unique molecular identifier is ligated to unconverted nucleic acids in a cfDNA sample before a).

In some embodiments, the nucleic acid molecules are subjected to cytosine-to-uracil conversion conditions using chemical methods, enzymatic methods or a combination thereof.

In some embodiments, the cfDNA in a biological sample is treated with a reagent selected from the group consisting of bisulfite, hydrogen sulfite, disulfite, and combinations thereof.

In some embodiments, the biological sample obtained from the subject is selected from the group consisting of body fluids, stool, colonic effluent, urine, blood plasma, blood serum, whole blood, isolated blood cells, cells isolated from the blood, and combinations thereof.

In some embodiments, the method comprises applying the measured methylation signature panel from the subject against a database of measured methylation signature panels from normal subjects, wherein the database is stored on a computer system; determining that the subject has an increased risk of having a cell proliferative disorder by measuring a change of at least 15% in the methylation status of the methyl signature panel relative to methylation status from normal subjects.

In some embodiments, the cell proliferative disorder is selected from stage 1 cancer, stage 2 cancer, stage 3 cancer, and stage 4 cancer.

In another aspect, the present disclosure provides a method for detecting a cell proliferative disorder in a biological subject comprising:

a) obtaining methylation sequencing information for a preselected panel of genomic regions associated with the presence of 2 or more different cell proliferative disorder tissue types from a nucleic acid sample from the subject, b) applying the sequence information from the subject to a classification model trained on a preselected panel of genomic regions associated with the presence of 2 or more cell proliferative disorder types, to identify the presence of a cell proliferative disorder, and if a cell proliferative disorder is detected, and c) applying sequence information from the subject to a classification model trained on a preselected panel of genomic regions associated with associated with the presence of cell proliferative disorders in different tissue types to determine tissue of origin of the cell proliferative disorder in the subject.

In an aspect, the present disclosure provides a method for detecting a cell proliferative disorder in a subject comprising a) obtaining methylation sequencing information disorders from a nucleic acid sample from the subject for a preselected panel of genomic regions associated with two or more different cell proliferative disorders, b) calculating a methylation profile of cfDNA in the sample corresponding to the preselected panel of predetermined methylated genomic regions associated with two or more types of cell proliferative disorders, and c) applying a machine learning classifier trained on a panel of predetermined methylated genomic regions associated with two or more types of cell proliferative disorder, and having pre-selected sensitivity and specificity for the different types of cell proliferative disorder to be detected using the panel.

In various embodiments, the different types of cell proliferative disorders are selected from colorectal cancer, breast cancer, ovarian cancer, prostate cancer, lung cancer, pancreatic cancer, uterine cancer, liver cancer, esophagus cancer, stomach cancer, thyroid cancer, or bladder cancer, In one embodiment, the machine learning classifier is tailored to provide pre-selected sensitivity and specificity for the different types of cell proliferative disorder to be detected depending on needs of cancer diagnosis and confirmatory diagnosis for two or more cancers selected from colorectal cancer, breast cancer, ovarian cancer, prostate cancer, lung cancer, pancreatic cancer, uterine cancer, liver cancer, esophagus cancer, stomach cancer, thyroid cancer, or bladder cancer, or combinations thereof.

In one embodiment, the pre-selected sensitivity for a colorectal cancer associated classification panel is at least 70% sensitivity; the pre-selected specificity for a breast cancer associated classification panel is at least 70% specificity; the pre-selected specificity for an ovarian cancer associated classification panel is at least 90% specificity; the pre-selected specificity for a prostate cancer associated classification panel is at least 70% specificity; the pre-selected specificity for a lung cancer associated classification panel is at least 70% specificity; the pre-selected specificity for a pancreatic cancer associated classification panel is at least 90% specificity; the pre-selected specificity for a uterine cancer associated classification panel is at least 90% specificity; the pre-selected sensitivity for a liver cancer associated classification panel is at least 70% sensitivity; the pre-selected sensitivity for an esophagus cancer associated classification panel is at least 70% sensitivity; the pre-selected sensitivity for a stomach cancer associated classification panel is at least 70% sensitivity; the pre-selected specificity for a thyroid cancer associated classification panel is at least 70% specificity; or the pre-selected sensitivity for a bladder cancer associated classification panel is at least 70% sensitivity selected based on which cancer types are detected by the classification model.

In an aspect, the present disclosure provides a method for detecting a presence or an absence of a cell proliferative disorder in a subject, comprising:

a) providing conditions capable of converting unmethylated cytosines to uracils in nucleic acid molecules of a biological sample obtained or derived from the subject to produce a plurality of converted nucleic acids;

b) contacting the plurality of converted nucleic acids with nucleic acid probes complementary to a pre-identified methylation signature panel of at least two differentially methylated regions selected from the group consisting of differentially methylated regions in Tables 1-17 to enrich for sequences corresponding to the signature panel;

c) determining nucleic acid sequences of the converted nucleic acid molecules;

d) aligning the nucleic acid sequences of the plurality of converted nucleic acid molecules to a reference nucleic acid sequence, thereby determining a methylation profile of the subject; and e) applying a trained machine learning classifier to the methylation profile, wherein the trained machine learning classifier is trained to be capable of distinguishing between healthy subjects and subjects with a cell proliferative disorder to provide an output value associated with presence of a cell proliferative disorder, thereby detecting the presence or the absence of the cell proliferative disorder in the subject.

In another aspect, the present disclosure provides a method for detecting a cell proliferative disorder in a subject, comprising:

a) providing conditions capable of converting unmethylated cytosines to uracils in nucleic acid molecules of a cfDNA sample to produce a plurality of converted nucleic acids;

b) amplifying converted nucleic acids with polymerase chain reaction;

c) probing the converted nucleic acids with nucleic acid probes complementary to a pre-identified methylation signature panel of at least two differentially methylated regions selected from Tables 1-17 to enrich for sequences corresponding to the signature panel;

d) determining the nucleic acid sequence of the converted nucleic acid molecules at a depth of greater than 5000×, and e) aligning the nucleic acid sequence of the converted nucleic acid molecules to a reference nucleic acid sequence for the pre-identified panel of CpG loci, to determine the methylation profile of the subject, and f) analyzing the methylation profile using a machine learning model trained to be capable of distinguishing between healthy subjects and subjects with a cell proliferative disorder to provide an output value associated with presence of a cell proliferative disorder, thereby indicating the presence of a cell proliferative disorder in the subject.

In some embodiments, the biological sample obtained from the subject is selected from the group consisting of body fluids, stool, colonic effluent, urine, blood plasma, blood serum, whole blood, isolated blood cells, cells isolated from the blood, and combinations thereof.

In some embodiments, the method comprises applying the measured methylation signature panel from the subject against a database of measured methylation signature panels from normal subjects, wherein the database is stored on a computer system; determining that the subject has an increased risk of having a cell proliferative disorder by measuring a change of at least 15% in the methylation status of the methyl signature panel relative to methylation status from normal subjects.

In some embodiments, the cell proliferative disorder is selected from stage 1 cancer, stage 2 cancer, stage 3 cancer, and stage 4 cancer.

In some embodiments, the method detects pancreatic cancer and is performed in combination with detecting the presence or amount of CA19-9 protein in the biological sample.

In some embodiments, the method detects prostate cancer and is performed in combination with detecting the presence or amount of PSA protein in the biological sample.

In an aspect, the present disclosure provides a system comprising a machine learning model classifier for detecting a cell proliferative disorder, comprising:

a) a computer-readable medium comprising a classifier operable to classify subjects as having the cell proliferative disorder or not having the cell proliferative disorder based on a methylation signature panel of Tables 1-17 or combinations thereof; and b) one or more processors for executing instructions stored on the computer-readable medium.

In one embodiment, the system comprises the classifier loaded into a memory of a computer system, the machine learning model trained using training vectors obtained from training biological samples, a first subset of the training biological samples identified as having a cell proliferative disorder and a second subset of the training biological samples identified as not having a cell proliferative disorder.

In some embodiments, the classifier is provided in a system for detecting a cell proliferative disorder comprising:

a) a computer-readable medium comprising a classifier operable to classify the subjects based on a methylation signature panel described herein; and b) one or more processors for executing instructions stored on the computer-readable medium.

In some embodiments, the system comprises a classification circuit that is configured as a machine learning classifier selected from a deep learning classifier, a neural network classifier, a linear discriminant analysis (LDA) classifier, a quadratic discriminant analysis (QDA) classifier, a support vector machine (SVM) classifier, a random forest (RF) classifier, a linear kernel support vector machine classifier, a first or second order polynomial kernel support vector machine classifier, a ridge regression classifier, an elastic net algorithm classifier, a sequential minimal optimization algorithm classifier, a naive Bayes algorithm classifier, and principal component analysis classifier.

In some embodiments, the computer-readable medium is a non-transitory computer-readable medium comprising machine-executable code that, upon execution by one or more computer processors, implements any of the methods above or elsewhere herein.

In some embodiments, the system comprises one or more computer processors and computer memory coupled thereto. The computer memory comprises machine-executable code that, upon execution by the one or more computer processors, implements any of the methods described herein.

In another aspect, the present disclosure provides a method for monitoring minimal residual disease in a subject previously treated for disease comprising: determining a methylation profile as described herein as a baseline methylation state and repeating an analysis to determine the methylation profile at one or more predetermined time points, wherein a change from baseline indicates a change in the minimal residual disease status at baseline in the subject.

In some embodiments, the minimal residual disease is selected from response to treatment, tumor load, residual tumor post-surgery, relapse, secondary screen, primary screen, and cancer progression.

In another aspect, a method is provided for determining response to treatment.

In another aspect, a method is provided for monitoring tumor load.

In another aspect, a method is provided for detecting residual tumor post-surgery.

In another aspect, a method is provided for detecting relapse.

In another aspect, a method is provided for use as a secondary screen.

In another aspect, a method is provided for use as a primary screen.

In another aspect, a method is provided for monitoring cancer progression.

In some embodiments, the dataset is indicative of the presence or susceptibility of the cancer at a sensitivity of at least about 80%. In some embodiments, the dataset is indicative of the presence or susceptibility of the cancer at a sensitivity of at least about 90%. In some embodiments, the dataset is indicative of the presence or susceptibility of the cancer at a sensitivity of at least about 95%. In some embodiments, the dataset is indicative of the presence or susceptibility of the cancer at a positive predictive value (PPV) of at least about 70%. In some embodiments, the dataset is indicative of the presence or susceptibility of the cancer at a positive predictive value (PPV) of at least about 80%. In some embodiments, the dataset is indicative of the presence or susceptibility of the cancer at a positive predictive value (PPV) of at least about 90%. In some embodiments, the dataset is indicative of the presence or susceptibility of the cancer at a positive predictive value (PPV) of at least about 95%. In some embodiments, the dataset is indicative of the presence or susceptibility of the cancer at a positive predictive value (PPV) of at least about 99%. In some embodiments, the dataset is indicative of the presence or susceptibility of the cancer at a negative predictive value (NPV) of at least about 80%. In some embodiments, the dataset is indicative of the presence or susceptibility of the cancer at a negative predictive value (NPV) of at least about 90%. In some embodiments, the dataset is indicative of the presence or susceptibility of the cancer at a negative predictive value (NPV) of at least about 95%. In some embodiments, the dataset is indicative of the presence or susceptibility of the cancer at a negative predictive value (NPV) of at least about 99%. In some embodiments, the trained algorithm determines the presence or susceptibility of the cancer of the subject with an Area Under Curve (AUC) of at least about 0.90. In some embodiments, the trained algorithm determines the presence or susceptibility of the cancer of the subject with an Area Under Curve (AUC) of at least about 0.95. In some embodiments, the trained algorithm determines the presence or susceptibility of the cancer of the subject with an Area Under Curve (AUC) of at least about 0.99.

In some embodiments, the method further comprises presenting a report a graphical user interface of an electronic device of a user. In some embodiments, the user is the subject, individual, or patient.

In some embodiments, the method further comprises determining a likelihood of the determination of a presence or susceptibility of cancer in the subject, individual, or patient.

In some embodiments, the trained algorithm (e.g., machine learning model or classifier) comprises a supervised machine learning algorithm. In some embodiments, the supervised machine learning algorithm comprises a deep learning algorithm, a support vector machine (SVM), a neural network, or a Random Forest.

In some embodiments, the method further comprises providing said subject with a therapeutic intervention based at least in part on the methylation profile or analysis, such as a therapeutic intervention to treat a patient with cancer (e.g., chemotherapy, radiotherapy, immunotherapy, or surgery).

In some embodiments, the method further comprises monitoring the presence or susceptibility of the cancer, wherein said monitoring comprises assessing the presence or susceptibility of the cancer of said subject at a plurality of time points, wherein the assessing is based at least on the presence or susceptibility of the cancer determined each of the plurality of time points.

In some embodiments, a difference in the assessment of the presence or susceptibility of the cancer of the subject among the plurality of time points is indicative of one or more clinical indications selected from the group consisting of: (i) a diagnosis of the presence or susceptibility of the cancer of the subject; (ii) a prognosis of the presence or susceptibility of the cancer of the subject; and (iii) an efficacy or non-efficacy of a course of treatment for treating the presence or susceptibility of the cancer of the subject.

In some embodiments, the method further comprises stratifying the cancer of the subject by using the trained algorithm to determine a sub-type of the cancer of the subject from among a plurality of distinct subtypes or stages of cancer.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

Examples of the present disclosure will now be described, by way of example only, with reference to the attached Figures. The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
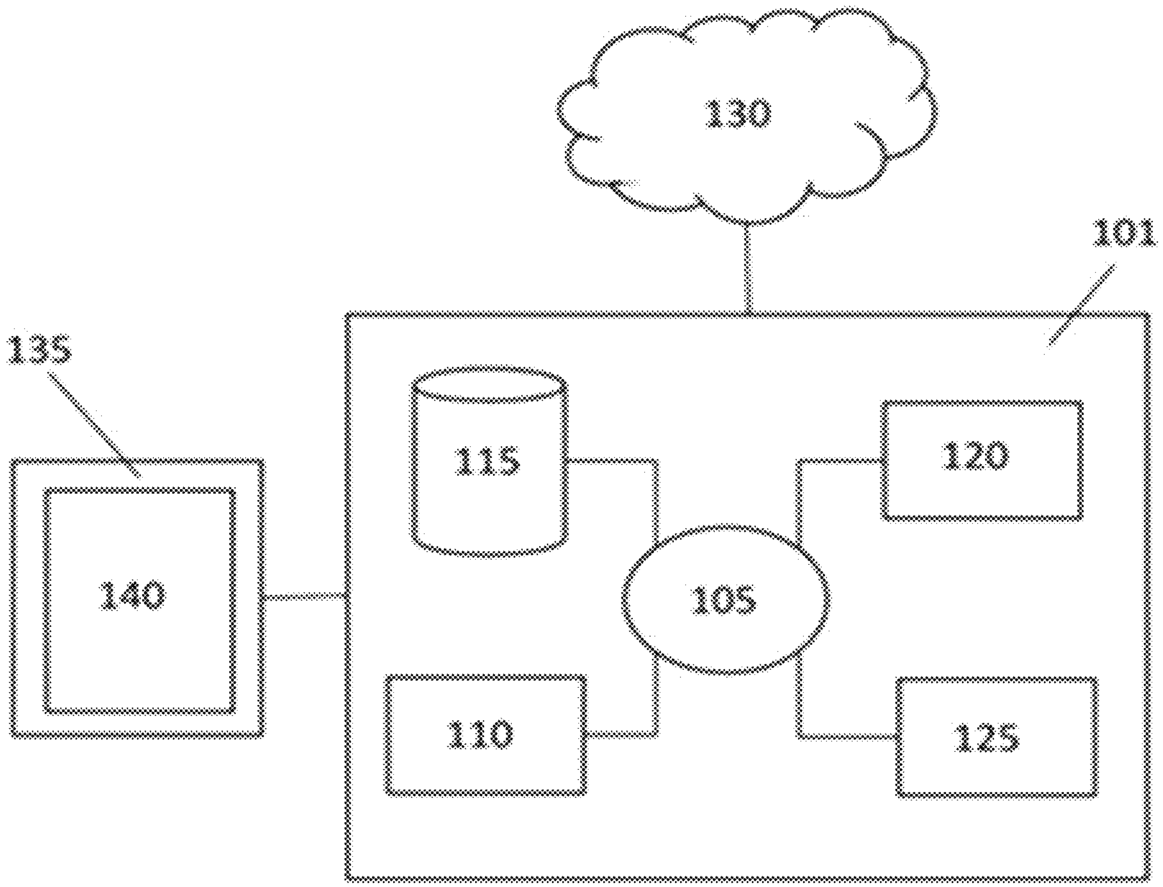
FIG. 1 provides a schematic of a computer system that is programmed or otherwise configured with machine learning models and classifiers to implement methods provided herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure relates generally to cancer detection and disease monitoring. More particularly, the field relates to cancer-related DNA methylation detection and disease monitoring in early-stage cancer. Cancer screening and monitoring may help to improve outcomes because early detection leads to a better outcome as the cancer may be eliminated before having the opportunity to spread. In the case of colorectal cancer, for instance, the use of colonoscopy may play a role in improving early diagnosis. Unfortunately, challenges arise with colonoscopies particularly due to low patient compliance with regular screening.

A primary issue for any screening tool may be the compromise between false positive and false negative results (or specificity and sensitivity), which lead to unnecessary investigations in the former case, and ineffectiveness in the latter case. An ideal test may be one that has a high Positive Predictive Value (PPV), minimizing unnecessary investigations but detecting the vast majority of cancers. Another key factor is "detection sensitivity". Distinct from test sensitivity, detection sensitivity is the lower limits of detection with respect to the size of the tumor. Unfortunately, waiting for a tumor to grow large enough to release circulating tumor markers at levels necessary for detection may contradict the goal of treating a tumor at the early stages where treatments are most effective. Hence, there is a need for effective blood-based screens for early-stage cancer based on circulating analytes.

Circulating tumor DNA may be a viable "liquid biopsy" for the detection and informative investigation of tumors in a non-invasive manner. The identification of tumor specific mutations in circulating tumor DNA may be applied to diagnosis of colon, breast, and prostate cancers. However, due to the high background of normal (e.g., non-tumor-derived) DNA present in the circulation, these techniques may be limited in sensitivity.

The detection of tumor-specific methylation in the blood may offer distinct advantages over the detection of mutations. A number of single or multiple methylation biomarkers may be assessed in cancers including colorectal, prostate, lung, breast, pancreatic, ovarian, uterine, liver, esophagus, stomach, or thyroid cancer. These biomarkers may suffer from low sensitivities as the biomarkers may be insufficiently prevalent in the tumors. There remains a need for more sensitive and specific screening tools for detecting early-stage or low tumor-burden cancer tumor signals in relapse and primary screening in at risk populations.

The present disclosure provides methods and systems directed to methylation-profiling of genes associated with cancer detection and disease progression.

In an aspect, the present disclosure provides methods that use a panel of methylated regions useful for the analysis of methylation within a region or gene. Other aspects provide novel uses of the region, gene, and the gene product as well as methods, assays, and kits directed to detecting, differentiating, and distinguishing cell proliferative disorders. The method and nucleic acids provided herein may be used for the analysis of cell proliferative disorders such as adenocarcinomas, adenomas, polyps, squamous cell cancers, carcinoid tumors, sarcomas, and lymphomas.

In some embodiments, the method comprises the use of one or more genes of methylated regions as markers for the differentiation, detection, and distinguishing of cell proliferative disorders. In some embodiments, the method comprises analysis of the methylation status of one or more genes selected from methylated regions described herein and their promoter or regulatory elements.

Methods and systems of the present disclosure may comprise analysis of the methylation state of the CpG dinucleotides within one or more of the genomic sequences according to methylated regions described here and sequences complementary thereto.

I. Definitions

As used in the specification and claims, the singular form "a", "an", and "the" include plural references unless the context clearly dictates otherwise. For example, the term "a nucleic acid" includes a plurality of nucleic acids, including mixtures thereof.

As used herein, the term "subject" generally refers to an entity or a medium that has testable or detectable genetic information. A subject can be a person, individual, or patient. A subject can be a vertebrate, such as, for example, a mammal. Non-limiting examples of mammals include humans, simians, farm animals, sport animals, rodents, and pets. The subject can be a person that has cancer or is suspected of having cancer. The subject may be displaying a symptom(s) indicative of a health or physiological state or condition of the subject, such as a cancer or other disease, disorder, or condition of the subject. As an alternative, the subject can be asymptomatic with respect to such health or physiological state or condition.

As used herein, the term "sample" generally refers to a biological sample obtained from or derived from one or more subjects. Biological samples may be cell-free biological samples or substantially cell-free biological samples, or may be processed or fractionated to produce cell-free biological samples. For example, cell-free biological samples may include cell-free ribonucleic acid (cfRNA), cell-free deoxyribonucleic acid (cfDNA), cell-free fetal DNA (cffDNA), plasma, serum, urine, saliva, amniotic fluid, and derivatives thereof. Cell-free biological samples may be obtained or derived from subjects using an ethylenediaminetetraacetic acid (EDTA) collection tube, a cell-free RNA collection tube (e.g., Streck®), or a cell-free DNA collection tube (e.g., Streck®). Cell-free biological samples may be derived from whole blood samples by fractionation. Biological samples or derivatives thereof may contain cells. For example, a biological sample may be a blood sample or a derivative thereof (e.g., blood collected by a collection tube or blood drops).

As used herein, the term "nucleic acid" generally refers to a polymeric form of nucleotides of any length, either deoxyribonucleotides (dNTPs) or ribonucleotides (rNTPs), or analogs thereof. Nucleic acids may have any three-dimensional structure, and may perform any function, known or unknown. Non-limiting examples of nucleic acids include deoxyribonucleic (DNA), ribonucleic acid (RNA), coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation or binding with a reporter agent As used herein, the term "target nucleic acid" generally refers to a nucleic acid molecule in a starting population of nucleic acid molecules having a nucleotide sequence whose presence, amount, and/or sequence, or changes in one or more of these, are desired to be determined. A target nucleic acid may be any type of nucleic acid, including DNA, RNA, and analogs thereof. As used herein, a "target ribonucleic acid (RNA)" generally refers to a target nucleic acid that is RNA. As used herein, a "target deoxyribonucleic acid (DNA)" generally refers to a target nucleic acid that is DNA.

As used herein, the terms "amplifying" and "amplification" generally refer to increasing the size or quantity of a nucleic acid molecule. The nucleic acid molecule may be single-stranded or double-stranded. Amplification may include generating one or more copies or "amplified product" of the nucleic acid molecule. Amplification may be performed, for example, by extension (e.g., primer extension) or ligation. Amplification may include performing a primer extension reaction to generate a strand complementary to a single-stranded nucleic acid molecule, and in some cases generate one or more copies of the strand and/or the single-stranded nucleic acid molecule. The term "DNA amplification" generally refers to generating one or more copies of a DNA molecule or "amplified DNA product." The term "reverse transcription amplification" generally refers to the generation of deoxyribonucleic acid (DNA) from a ribonucleic acid (RNA) template via the action of a reverse transcriptase The term "cell-free nucleic acid (cfNA)", as used herein, generally refers to nucleic acids (such as cell-free RNA ("cfRNA") or cell-free DNA ("cfDNA")) in a biological sample that are not contained in a cell. cfDNA may circulate freely in in a bodily fluid, such as in the bloodstream.

The term "cell-free sample", as used herein, generally refers to a biological sample that is substantially devoid of intact cells. This may be derived from a biological sample that is itself substantially devoid of cells or may be derived from a sample from which cells have been removed. Examples of cell-free samples include those derived from blood, such as serum or plasma; urine; or samples derived from other sources, such as semen, sputum, feces, ductal exudate, lymph, or recovered lavage.

The term "circulating tumor DNA", as used herein, generally refers to cfDNA originating from a tumor.

The term "genomic region", as used herein, generally refers to identified regions of nucleic acid that are identified by their location in the chromosome. In some examples, the genomic regions are referred to by a gene name and encompass coding and non-coding regions associated with that physical region of nucleic acid. As used herein, a gene comprises coding regions (exons), non-coding regions (introns), transcriptional control or other regulatory regions, and promoters. In another example, the genomic region may incorporate an intron or exon or an intron/exon boundary within a named gene.

The term "CpG islands" or "CGI", as used herein, generally refers to a contiguous region of genomic DNA that satisfies the criteria of (1) having a frequency of CpG dinucleotides corresponding to an "Observed/Expected Ratio" greater than about 0.6, and (2) having a "GC Content" greater than about 0.5. CpG islands may be between about 0.2 to about 3 kilobases (kb) in length having a high frequency of CpG sites. CpG islands may be found at or near promoters of about 40% of mammalian genes. CpG islands may also be found outside of mammalian genes. In some examples, CpG islands are found in exons, introns, promoters, enhancers, inhibitors, and transcriptional regulatory elements. CpG islands may tend to occur upstream of so-called "housekeeping genes". CpG islands may have a CpG dinucleotide content of at least about 60% of what would be statistically expected. The occurrence of CpG islands at or upstream of the 5' end of genes may reflect a role in the regulation of transcription. Methylation of CpG sites within the promoters of genes may lead to silencing. Silencing of tumor suppressors by methylation may be, in turn, a hallmark of a number of human cancers.

The term "CpG shores" or "CGI shores", as used herein, generally refers to regions extending short distances from CpG islands in which methylation may also occur. CpG shores may be found in the region about 0 to 2 kb upstream and downstream of a CpG island.

The term "CpG shelves" or "CGI shelves", as used herein, generally refers to regions extending short distances from CpG shores in which methylation may also occur. CpG shelves may generally be found in the region between about 2 kb and 4 kb upstream and downstream of a CpG island (e.g., extending a further 2 kb out from a CpG shore).

The term "cell proliferative disorder", as used herein, generally refers to a disorder or disease that comprises disordered or aberrant proliferation of cells. In some non-limiting examples, the disorder is colorectal cell proliferation, prostate cell proliferation, lung cell proliferation, breast cell proliferation, pancreatic cell proliferation, ovarian cell proliferation, uterine cell proliferation, liver cell proliferation, esophagus cell proliferation, stomach cell proliferation, or thyroid cell proliferation. In some embodiments, the cell proliferative disorder is colon adenocarcinoma, liver hepatocellular carcinoma, lung adenocarcinoma, lung squamous cell carcinoma, ovarian serous cystadenocarcinoma, pancreatic adenocarcinoma, prostate adenocarcinoma, or rectum adenocarcinoma.

The term "normal" or "healthy", as used herein, generally refers to a cell, tissue, plasma, blood, biological sample, or subject not having a cell proliferative disorder.

The term "epigenetic parameters", as used herein, generally refers to cytosine methylations. Further epigenetic parameters may include, for example, the acetylation of histones which may correlate with the DNA methylation.

The term "genetic parameters", as used herein, generally refers to mutations and polymorphisms of genes and sequences further required for gene regulation. Examples of mutations include insertions, deletions, point mutations, inversions, and polymorphisms such as SNPs (single nucleotide polymorphisms).

The term "hemi-methylation" or "hemimethylation", as used herein, generally refers to the methylation state of a palindromic CpG methylation site, where only a single cytosine in one of the two CpG dinucleotide sequences of the palindromic CpG methylation site is methylated (e.g., 5'-CC$^{M}$GG-3' (top strand): 3'-GGCC-5' (bottom strand)).

The term "hypermethylation", as used herein, generally refers to the average methylation state corresponding to an increased presence of 5-mC at one or a plurality of CpG dinucleotides within a DNA sequence of a test DNA sample, relative to the amount of 5-mC found at corresponding CpG dinucleotides within a normal control DNA sample. In some embodiments, the test DNA sample is from an individual having a cell proliferative disorder.

The term "hypomethylation", as used herein, generally refers to the average methylation state corresponding to a decreased presence of 5-mC at one or a plurality of CpG dinucleotides within a DNA sequence of a test DNA sample, relative to the amount of 5-mC found at corresponding CpG dinucleotides within a normal control DNA sample. In some embodiments, the test DNA sample is from an individual having a cell proliferative disorder.

The term "methylation state" or "methylation status", as used herein, generally refers to the presence or absence of 5-methylcytosine ("5-mC") at one or a plurality of CpG dinucleotides within a DNA sequence. Methylation states at one or more particular palindromic CpG methylation sites (each having two CpG dinucleotide sequences) within a DNA sequence include "unmethylated," "fully-methylated", and "hemi-methylated."

The term "methylated cytosine", as used herein, generally refers to any methylated forms of the nucleic acid base cytosine that contains a methyl or hydroxymethyl functional group at the 5' position. Methylated cytosines may be regulators of gene transcription in genomic DNA. This term may include 5-methylcytosine and 5-hydroxymethylcytosine.

The term "methylation assay" refers to any assay for determining the methylation state of one or more CpG dinucleotide sequences within a sequence of DNA.

The term "minimal residual disease" or "MRD" refers to the small number of cancer cells in the body after cancer treatment. MRD testing may be performed to determine whether the cancer treatment is working and to guide further treatment plans.

The term "MSP" (Methylation-specific PCR), as used herein, generally refers to a methylation assay, such as that described by Herman et al. Proc. Natl. Acad. Sci. USA 93:9821-9826, 1996, and by U.S. Pat. No. 5,786,146, the contents of each of which are incorporated herein by reference herein in its entirety.

The term "methylation converted" or "converted" nucleic acid, as used herein, generally refers to nucleic acid, such as for example DNA, that has undergone a process used to convert the DNA for methylation sequencing. Examples of conversion processes include reagent-based (such as bisulfite) conversion, enzymatic conversion, or combination conversion (such as TAPS conversion) where unmethylated cytosines are converted into uracil prior to PCR amplification or sequencing. The conversion process may be used in methyl sequencing methods to distinguish between methylated and unmethylated cytosine bases.

The term "region methylated in cancer", as used herein, generally refers to a segment of the genome containing methylation sites (CpG dinucleotides), methylation of which is associated with a malignant cellular state. Methylation of a region may be associated with more than one different type of cancer, or with one type of cancer specifically. Within this, methylation of a region may be associated with more than one cancer subtype, or with one cancer subtype specifically.

The terms cancer "type" and "subtype" generally are used relatively herein, such that one "type" of cancer, such as breast cancer, may be "subtypes" based on, e.g., stage, morphology, histology, gene expression, receptor profile, mutation profile, aggressiveness, prognosis, malignant characteristics, etc. Likewise, "type" and "subtype" may be applied at a finer level, e.g., to differentiate one histological "type" into "subtypes", e.g., defined according to mutation profile or gene expression. Cancer "stage" may also be used to refer to classification of cancer types based on histological and pathological characteristics relating to disease progression.

II. Assaying Samples

The cell-free biological samples may be obtained or derived from a human subject. The cell-free biological samples may be stored in a variety of storage conditions before processing, such as different temperatures (e.g., at room temperature, under refrigeration or freezer conditions, at 25° C., at 4° C., at −18° C., −20° C., or at −80° C.) or different suspensions (e.g., EDTA collection tubes, cell-free RNA collection tubes, or cell-free DNA collection tubes).

The cell-free biological sample may be obtained from a subject with a cancer, from a subject that is suspected of having a cancer, or from a subject that does not have or is not suspected of having the cancer.

The cell-free biological sample may be taken before and/or after treatment of a subject with the cancer. Cell-free biological samples may be obtained from a subject during a treatment or a treatment regime. Multiple cell-free biological samples may be obtained from a subject to monitor the effects of the treatment over time. The cell-free biological sample may be taken from a subject known or suspected of having a cancer for which a definitive positive or negative diagnosis is not available via clinical tests. The sample may be taken from a subject suspected of having a cancer. The cell-free biological sample may be taken from a subject experiencing unexplained symptoms, such as fatigue, nausea, weight loss, aches and pains, weakness, or bleeding. The cell-free biological sample may be taken from a subject having explained symptoms. The cell-free biological sample may be taken from a subject at risk of developing a cancer due to factors such as familial history, age, hypertension or pre-hypertension, diabetes or pre-diabetes, overweight or obesity, environmental exposure, lifestyle risk factors (e.g., smoking, alcohol consumption, or drug use), or presence of other risk factors.

The cell-free biological sample may contain one or more analytes capable of being assayed, such as cell-free ribonucleic acid (cfRNA) molecules suitable for assaying to generate transcriptomic data, cell-free deoxyribonucleic acid (cfDNA) molecules suitable for assaying to generate genomic data, or a mixture or combination thereof. One or more such analytes (e.g., cfRNA molecules and/or cfDNA molecules) may be isolated or extracted from one or more cell-free biological samples of a subject for downstream assaying using one or more suitable assays.

After obtaining a cell-free biological sample from the subject, the cell-free biological sample may be processed to generate datasets indicative of a cancer of the subject. For example, a presence, absence, or quantitative assessment of nucleic acid molecules of the cell-free biological sample at a panel of cancer-associated genomic loci (e.g., quantitative measures of RNA transcripts or DNA at the cancer-associated genomic loci). Processing the cell-free biological sample obtained from the subject may comprise (i) subjecting the cell-free biological sample to conditions that are sufficient to isolate, enrich, or extract a plurality of nucleic acid molecules, and (ii) assaying the plurality of nucleic acid molecules to generate the dataset.

In some embodiments, a plurality of nucleic acid molecules is extracted from the cell-free biological sample and subjected to sequencing to generate a plurality of sequencing reads. The nucleic acid molecules may comprise ribonucleic acid (RNA) or deoxyribonucleic acid (DNA). The nucleic acid molecules (e.g., RNA or DNA) may be extracted from the cell-free biological sample by a variety of methods, such as a FastDNA Kit® protocol from MP Biomedicals, a QIAamp® DNA cell-free biological mini kit from Qiagen, or a cell-free biological DNA isolation kit protocol from Norgen Biotek. The extraction method may extract all RNA or DNA molecules from a sample. Alternatively, the extraction method may selectively extract a portion of RNA or DNA molecules from a sample. Extracted RNA molecules from a sample may be converted to DNA molecules by reverse transcription (RT).

The sequencing may be performed by any suitable sequencing methods, such as massively parallel sequencing (MPS), paired-end sequencing, high-throughput sequencing, next-generation sequencing (NGS), shotgun sequencing, single-molecule sequencing, nanopore sequencing, semiconductor sequencing, pyrosequencing, sequencing-by-synthesis (SBS), sequencing-by-ligation, sequencing-by-hybridization, and RNA-Seq (Illumina).

The sequencing may comprise nucleic acid amplification (e.g., of RNA or DNA molecules). In some embodiments, the nucleic acid amplification is polymerase chain reaction (PCR). A suitable number of rounds of PCR (e.g., PCR, qPCR, reverse-transcriptase PCR, digital PCR, etc.) may be performed to sufficiently amplify an initial amount of nucleic acid (e.g., RNA or DNA) to a desired input quantity for subsequent sequencing. In some cases, the PCR may be used for global amplification of target nucleic acids. This may comprise using adapter sequences that may be first ligated to different molecules followed by PCR amplification using universal primers. PCR may be performed using any of a number of commercial kits, e.g., provided by Life Technologies, Affymetrix, Promega, Qiagen, etc. In other cases, only certain target nucleic acids within a population of nucleic acids may be amplified. Specific primers, possibly in conjunction with adapter ligation, may be used to selectively amplify certain targets for downstream sequencing. The PCR may comprise targeted amplification of one or more genomic loci, such as genomic loci associated with cancers. The sequencing may comprise use of simultaneous reverse transcription (RT) and polymerase chain reaction (PCR), such as a OneStep RT-PCR kit protocol by Qiagen, NEB, Thermo Fisher Scientific, or Bio-Rad.

RNA or DNA molecules isolated or extracted from a cell-free biological sample may be tagged, e.g., with identifiable tags, to allow for multiplexing of a plurality of samples. Any number of RNA or DNA samples may be multiplexed. For example, a multiplexed reaction may contain RNA or DNA from at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more than 100 initial cell-free biological samples. For example, a plurality of cell-free biological samples may be tagged with sample barcodes such that each DNA molecule may be traced back to the sample (and the subject) from which the DNA molecule originated. Such tags may be attached to RNA or DNA molecules by ligation or by PCR amplification with primers.

After subjecting the nucleic acid molecules to sequencing, suitable bioinformatics processes may be performed on the sequence reads to generate the data indicative of the presence, absence, or relative assessment of the cancer. For example, the sequence reads may be aligned to one or more reference genomes (e.g., a genome of one or more species such as a human genome). The aligned sequence reads may be quantified at one or more genomic loci to generate the datasets indicative of the cancer. For example, quantification of sequences corresponding to a plurality of genomic loci associated with cancers may generate the datasets indicative of the cancer.

The cell-free biological sample may be processed without any nucleic acid extraction. For example, the cancer may be identified or monitored in the subject by using probes configured to selectively enrich nucleic acid (e.g., RNA or DNA) molecules corresponding to the plurality of cancer-associated genomic loci. The probes may be nucleic acid primers. The probes may have sequence complementarity with nucleic acid sequences from one or more of the plurality of cancer-associated genomic loci or genomic regions. The plurality of cancer-associated genomic loci or genomic regions may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, or more distinct cancer-associated genomic loci or genomic regions. The plurality of cancer-associated genomic loci or genomic regions may comprise one or more members (e.g., 1, 2, 3, 4, 5, 6, 7, 8, 9, 10, 11, 12, 13, 14, 15, 16, 17, 18, 19, 20, about 25, about 30, about 35, about 40, about 45, about 50, about 55, about 60, about 65, about 70, about 75, about 80, or more) selected from the group listed in Tables 1-11. The cancer-associated genomic loci or genomic regions may be associated with various stages or sub-types of cancer (e.g., colorectal cancer).

The probes may be nucleic acid molecules (e.g., RNA or DNA) having sequence complementarity with nucleic acid sequences (e.g., RNA or DNA) of the one or more genomic loci (e.g., cancer-associated genomic loci). These nucleic acid molecules may be primers or enrichment sequences. The assaying of the cell-free biological sample using probes that are selective for the one or more genomic loci (e.g., cancer-associated genomic loci) may comprise use of array hybridization (e.g., microarray-based), polymerase chain reaction (PCR), or nucleic acid sequencing (e.g., RNA sequencing or DNA sequencing). In some embodiments, DNA or RNA may be assayed by one or more of: isothermal DNA/RNA amplification methods (e.g., loop-mediated isothermal amplification (LAMP), helicase dependent amplification (HDA), rolling circle amplification (RCA), recombinase polymerase amplification (RPA)), immunoassays, electrochemical assays, surface-enhanced Raman spectroscopy (SERS), quantum dot (QD)-based assays, molecular inversion probes, droplet digital PCR (ddPCR), CRISPR/Cas-based detection (e.g., CRISPR-typing PCR (ctPCR), specific high-sensitivity enzymatic reporter un-locking (SHERLOCK), DNA endonuclease targeted CRISPR trans reporter (DETECTR), and CRISPR-mediated analog multi-event recording apparatus (CAMERA)), and laser transmission spectroscopy (LTS).

The assay readouts may be quantified at one or more genomic loci (e.g., cancer-associated genomic loci) to generate the data indicative of the cancer. For example, quantification of array hybridization or polymerase chain reaction (PCR) corresponding to a plurality of genomic loci (e.g., cancer-associated genomic loci) may generate data indicative of the cancer. Assay readouts may comprise quantitative PCR (qPCR) values, digital PCR (dPCR) values, digital droplet PCR (ddPCR) values, fluorescence values, etc., or normalized values thereof. The assay may be a home use test configured to be performed in a home setting.

In some embodiments, multiple assays may be used to simultaneously process cell-free biological samples of a subject. For example, a first assay may be used to process a first cell-free biological sample obtained or derived from the subject to generate a first dataset indicative of the cancer; and a second assay different from the first assay may be used to process a second cell-free biological sample obtained or derived from the subject to generate a second dataset indicative of the cancer. Any or all of the first dataset and the second dataset may then be analyzed to assess the cancer of the subject. For example, a single diagnostic index or diagnosis score can be generated based on a combination of the first dataset and the second dataset. As another example, separate diagnostic indexes or diagnosis scores can be generated based on the first dataset and the second dataset.

The cell-free biological samples may be processed using a methylation-specific assay. For example, a methylation-specific assay can be used to identify a quantitative measure (e.g., indicative of a presence, absence, or relative amount) of methylation each of a plurality of cancer-associated genomic loci in a cell-free biological sample of the subject. The methylation-specific assay may be configured to process cell-free biological samples such as a blood sample or a urine sample (or derivatives thereof) of the subject. A quantitative measure (e.g., indicative of a presence, absence, or relative amount) of methylation of cancer-associated genomic loci in the cell-free biological sample may be indicative of one or more cancers. The methylation-specific assay may be used to generate datasets indicative of the quantitative measure (e.g., indicative of a presence, absence, or relative amount) of methylation of each of a plurality of cancer-associated genomic loci in the cell-free biological sample of the subject.

The methylation-specific assay may comprise, for example, one or more of: a methylation-aware sequencing (e.g., using bisulfate treatment), pyrosequencing, methylation-sensitive single-strand conformation analysis (MS-SSCA), high-resolution melting analysis (HRM), methylation-sensitive single-nucleotide primer extension (MS-SnuPE), base-specific cleavage/MALDI-TOF, microarray-based methylation assay, methylation-specific PCR, targeted bisulfite sequencing, oxidative bisulfite sequencing, mass spectroscopy-based bisulfite sequencing, or reduced representation bisulfite sequence (RRBS).

III. Signature Panels

The present disclosure provides methods and systems to analyze biological samples to obtain measurable features from a combination of hypermethylated regions in DNA in the sample that are associated with the development of cell proliferative disorders to identify a signature panel of regions. The features from the signature panel may be processed using a trained algorithm (e.g., a machine learning model) to create a classifier configured to stratify a population of individuals with a cell proliferative disorder. The methods are characterized by using one or more nucleic acids having methylated regions described in the signature panels which are contacted with a reagent or series of reagents capable of distinguishing between methylated and non-methylated CpG dinucleotides within the identified regions prior to sequencing.

The signature panels described herein generally refer to a collection of targeted regions of genomic DNA that are identified in a cell-free nucleic acid sample and display an increased methylation at cytosine bases in samples associated with a cell proliferative disorder. The formation of signature panels may allow for a quick and specific analysis of specific methylated regions associated with cell proliferative disorders. The signature panel(s) as described and employed in the methods herein may be used for the improved diagnosis, prognosis, treatment selection, and monitoring (e.g., treatment monitoring) of cell proliferative disorders such as cancers.

The signature panels and methods may provide significant improvements over current approaches to detect early-stage cell proliferative disorders from body fluid samples such as whole blood, plasma, or serum.

In some embodiments, the regions methylated in cancer comprise CpG islands. In some embodiments, the regions methylated in cancer comprise CpG shores. In some embodiments, the regions methylated in cancer comprise CpG shelves. In some embodiments, the regions methylated in cancer comprise CpG islands and CpG shores. In some embodiments, the regions methylated in cancer comprise CpG islands, CpG shores, and CpG shelves.

In some embodiments, the regions methylated in cancer comprise CpG islands and sequences about 0 to 4 kb upstream and downstream of the CpG islands. The regions methylated in cancer may also comprise CpG islands and sequences about 0 to 3 kb upstream and downstream, about 0 to 2 kb upstream and downstream, about 0 to 1 kb upstream and downstream, about 0 to 500 base pairs (bp) upstream and downstream, about 0 to 400 bp upstream and downstream, about 0 to 300 bp upstream and downstream, about 0 to 200 bp upstream and downstream, or about 0 to 100 bp upstream and downstream of the CpG islands.

A number of design parameters may be considered in the selection of regions hypermethylated in cancer, according to some examples. In certain examples, the methylation region is about 200 bp, about 300 bp, about 400 bp, or about 500 bp in length. Data for this selection process may be obtained from a variety of sources, such as, e.g., The Cancer Genome Atlas (TCGA), derived by the use of, e.g., Illumina Infinium HumanMethylation450 BeadChip for a wide range of cancers, or from other sources based on, e.g., bisulfite whole genome sequencing, or other methodologies. In some embodiments, "methylation value" (which may be derived from TCGA level 3 methylation data, which is in turn derived from the beta-value, which ranges from about −0.5 to 0.5) may be used to select regions. In some embodiments, the amplification is carried out with primer sets designed to amplify at least one methylation site having a methylation value of below about −0.3 in normal issue. A methylation value may be established in a plurality of normal tissue samples, such as about 4. The methylation value may be at or below about −0.1, about −0.2, about −0.3, about −0.4, about −0.5, about −0.6, about −0.7, about −0.8, about −0.9, or about −1.0.

In some embodiments, the primer sets are designed to amplify at least one methylation site having a difference between the average methylation value in the cancer and the normal tissue of greater than a predefined threshold, such as about 0.3. In some embodiments, the difference may be greater than about 0.1, about 0.2, about 0.3, about 0.4, about 0.5, about 0.6, about 0.7, about 0.8, about 0.9, or about 1.0. Proximity of other methylation sites that meet this requirement may also play a role in selecting regions, in some examples. In some embodiments, the primer sets include primer pairs amplifying at least one methylation site having at least one methylation site within about 200 bp that also has a methylation value of below about −0.3 in normal issue, and a difference between the average methylation value in the cancer and the normal tissue of greater than about 0.3.

In some examples, target regions may be selected if the methylation in a region is greater than methylation in the same region in samples obtained or derived from one or more healthy individuals (e.g., individuals without cancer). Such selection may be performed manually or computationally. In certain examples, a region may be selected if the region has at least about 5%, about 10%, about 15%, about 20%, about 30%, about 40%, about 50%, about 55%, about 60%, about 65%, about 70%, about 75%, about 80%, about 85%, about 90%, about 95%, about 100%, or more than about 100% more methylation than a region in a sample from a healthy individual. In another example, a region may be selected if the number of reads mapped to the region in a disease sample at a predefined threshold methylated CpG count exceeds the same predefined threshold methylated CpG count for the same region in healthy individual samples. The methylated CpG count used as a baseline threshold in healthy samples may change for a given region, but the number of reads mapping to that region that exceeds the baseline threshold of methylated CpG count for that region in a healthy sample may indicate an important region regardless of the fluctuating threshold CpG count.

In some examples, target regions may be selected for amplification based on the number of samples in the validation set having methylation at that site. For example, a region may be selected if the region is more methylated in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99% of samples tested from disease individuals compared to samples from healthy individuals. For example, regions may be selected if the region is methylated in at least about 75% of tumors tested, including within specific subtypes. For some validations, tumor-derived cell lines may be used for the testing.

The present disclosure further provides a method for conducting an assay to ascertain genetic and/or epigenetic parameters of one or more genes selected from the group consisting of the signature panels described herein, and promoter and regulatory elements of the one or more genes. In some embodiments, the assays according to the following method are used to detect methylation within one or more genes selected from the group consisting of signature panels described herein, wherein said methylated nucleic acids are present in a solution further comprising an excess of background DNA, wherein the background DNA is present in between about 100 to 1,000 times, about 100 to 10,000 times, about 100 to 100,000 times, about 1,000 to 10,000 times, about 1,000 to 100,000 times, or about 10,000 to 100,000 times the concentration of the DNA to be detected. In some embodiments, the concentration of DNA to be detected is greater than about 100,000 times the background DNA concentration. In some embodiments, the method comprises contacting a nucleic acid sample obtained from a subject with at least one reagent or a series of reagents (e.g., that distinguishes between methylated and non-methylated CpG dinucleotides within the target nucleic acid).

A tumor or colon cell proliferative disorder, as described herein, may be selected from colorectal, prostate, lung, breast, pancreatic, ovarian, uterine, liver, esophagus, stomach, or thyroid cell proliferation. In some embodiments, the cell proliferative disorder is selected from colon adenocarcinoma, liver hepatocellular carcinoma, lung adenocarcinoma, lung squamous cell carcinoma, ovarian serious cystadenocarcinoma, pancreatic adenocarcinoma, prostate adenocarcinoma, and rectum adenocarcinoma.

A. Multi Tissue Type Cancer Marker Detection Panel

A signature panel comprising informative methylated regions may be selected according to the purpose of the intended assay. For targeted methods, primer pairs may be designed based on the set of intended target regions. Table 1 shows genomic methylation regions indicative of cancer. The methylation regions described herein are annotated to the human reference genome, e.g., from the Genome Reference Consortium Human Build 38 (GRCh38) (The Cancer Genome Atlas (TCGA)). In some embodiments, the set of regions comprises at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty five, at least thirty, at least thirty five, at least forty, at least forty five, at least fifty, at least fifty five, or more of the regions listed in Table 1. In some embodiments, the set of regions comprise all the regions listed in Table 1.

In some embodiments, the set of methyl regions associated with detection of different cancer types is selected from Table 1.

In some embodiments, the cancer panel comprises regions selected from at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty five, at least thirty, at least thirty five, at least forty, at least forty five, at least fifty, at least fifty five, or more of the regions listed in Table 1. In some embodiments, the cancer panel comprises all the regions listed in Table 1.

TABLE 1

| Closest Gene | Chromosome Number | Region Start | Region Stop |
|---|---|---|---|
| CRIPAK, UVSSA | chr4 | 1410251 | 1411075 |
| MEOX2 | chr7 | 15685300 | 15688105 |
| LRRN2 | chr1 | 204684180 | 204685942 |
| ZNF177 | chr19 | 9362913 | 9363600 |
| DPYSL2 | chr8 | 26578930 | 26579269 |
| CPNE5 | chr6 | 36839707 | 36841032 |
| PHOX2B | chr4 | 41744645 | 41745232 |
| GLB1L3 | chr11 | 134275700 | 134278165 |
| GRIN2A | chr16 | 10181849 | 10183617 |
| SERPINE2 | chr2 | 224038504 | 224040310 |
| LRRC41 | chr1 | 46302590 | 46304060 |
| TMEM101 | chr17 | 44014457 | 44015264 |
| LRRC41 | chr1 | 46301753 | 46301753 |
| TFAP2E | chr1 | 35576535 | 35578237 |
| ZNF154 | chr19 | 57708612 | 57709440 |
| IRF2BP1 | chr19 | 45876550 | 45877420 |
| LYPLAL1-DT | chr1 | 219173767 | 219174230 |
| SCRG1 | chr4 | 173508370 | 173510040 |
| PDXK | chr21 | 43728573 | 43729711 |
| LOC100286906 | chr7 | 155371315 | 155374020 |
| HOPX | chr4 | 56655120 | 56656970 |
| ITGA4 | chr2 | 181456459 | 181458643 |
| PPP1R16B | chr20 | 38804789 | 38807565 |
| HOXA1 | chr7 | 27095185 | 27097167 |
| TCF24 | chr8 | 66961153 | 66963484 |
| LOC100130992 | chr10 | 22252193 | 22254000 |
| LOC100286906 | chr7 | 155371315 | 155374020 |
| EMILIN2 | chr18 | 2847184 | 2848342 |
| IRF4 | chr6 | 391101 | 392638 |
| OR1F2P | chr16 | 3187792 | 3189855 |
| MOB3B | chr9 | 27528978 | 27529887 |
| IRF2BP1 | chr19 | 45876550 | 45877420 |
| AKR1B1 | chr7 | 134458200 | 134459533 |
| KLK10 | chr19 | 51018748 | 51020133 |
| ZSCAN12 | chr6 | 28399347 | 28400210 |
| RNVU1-8 | chr1 | 147083835 | 147085351 |
| PPP1R16B | chr20 | 38804789 | 38807565 |
| LOC100130298 | chr8 | 60909799 | 60910469 |
| LOC100507557 | chr6 | 145814298 | 145815785 |
| UBXN10 | chr1 | 20185867 | 20186730 |
| ZNF625 | chr19 | 12155907 | 12156871 |
| LOC392232 | chr8 | 72251140 | 72251956 |
| BASP1-AS1 | chr5 | 17217516 | 17219975 |
| LINC01264 | chr10 | 42932936 | 42933788 |
| KIF7 | chr15 | 89654755 | 89655920 |
| TWIST1 | chr7 | 19112343 | 19112657 |
| SNORD12 | chr20 | 49318252 | 49319561 |
| ARHGEF16 | chr1 | 3393377 | 3394370 |
| SLCO3A1 | chr15 | 91852783 | 91854800 |
| TBX18 | chr6 | 84762839 | 84765672 |
| GTDC1 | chr2 | 143936690 | 143937919 |
| SHISA3 | chr4 | 42397040 | 42398745 |
| AKR1B1 | chr7 | 134458200 | 134459533 |
| HOXA1 | chr7 | 27095185 | 27097167 |
| SPAG6 | chr10 | 22334421 | 22337305 |
| IRF4 | chr6 | 391101 | 392638 |
| PRKCB | chr16 | 23835195 | 23837445 |
| PFKP | chr10 | 3066025 | 3067776 |
| FLT3 | chr13 | 28099335 | 28101240 |

In some embodiments, the method further comprises quantifying the methylation signals, wherein a number in excess of a predetermined threshold is indicative of a cell proliferative disorder such as cancer. In some embodiments, the quantifying and comparing are carried out independently for each of the sites methylated in a cell proliferative disorder. Accordingly, a count of positive tumor signals may be established for each site. In some embodiments, the method further comprises determining a proportion of the sequencing reads containing tumor signals, wherein the proportion in excess of a threshold is indicative of a cell proliferative disorder. In some embodiments, the determining is carried out independently for each of the sites methylated in a cell proliferative disorder.

The term "threshold", as used herein, generally refers to a value that is selected to discriminate, separate, or distinguish between two populations of subjects. In some embodiments, the threshold discriminates methylation status between a disease (e.g., malignant) state, and a non-disease (e.g., healthy) state. In some embodiments, the threshold discriminates between stages of disease (e.g., stage 1, stage 2, stage 3, or stage 4). Thresholds may be set according to the disease in question, and may be based on earlier analysis, e.g., of a training set or determined computationally on a set of inputs having known characteristic (e.g., healthy, disease, or stage of disease). Thresholds may also be set for a gene region according to the predictive value of methylation at a particular site. Thresholds may be different for each methylation site, and data from multiple sites may be combined in the end analysis.

B. Tissue of Origin Cancer Marker Detection Panel

In some embodiments, of the foregoing methods, the cancer panel comprises methylated genomic regions associated with tissue of origin (TOO) for a type of cancer. The following panels may be incorporated into machine learning classifiers, methods, and systems to determine tissue of origin of tumor-associated methylation signals in a biological sample.

i. Colorectal Cancer

Table 2 shows colorectal tissue of origin TCGA analysis methylation regions. In some embodiments, a cancer panel comprises one or more of the regions listed in Table 2. For example, a cancer panel comprises at least one, at least two, at least three, at least four, at least five, at least six, at least seven, at least eight, at least nine, or all of the genomic regions listed in Table 2. In some embodiments, a set of probes are directed to sequences selected from at least one, at least two, at least three, at least four, at least five, at least six, at least seven, at least eight, at least nine, or all of the genomic regions listed in Table 2.

TABLE 2

| Closest Gene | Chromosome Number | Region Start | Region Stop |
|---|---|---|---|
| GPC6 | chr13 | 93226527 | 93229026 |
| PLCB1 | chr20 | 8131515 | 8134057 |
| PNPLA5 | chr22 | 43890585 | 43892865 |
| NDUFA5P12 | chr8 | 47188540 | 47189584 |
| GRAMD1B | chr11 | 123357785 | 123358764 |
| RNU4-5P | chr10 | 109456465 | 109457325 |
| LRFN3 | chr19 | 35958969 | 35960233 |
| ABHD17AP6 | chr17 | 20852130 | 20853135 |
| GAMT | chr19 | 1400250 | 1401892 |
| WNT2 | chr7 | 117322020 | 117324934 |

Table 3 shows colorectal tissue of origin tissue methylation sequencing methylation regions. In some embodiments, a cancer panel comprises one or more of the regions listed in Table 3. For example, a cancer panel comprises at least one, at least two, at least three, at least four, at least five, at least six, at least seven, at least eight, at least nine, or all of the genomic regions listed in Table 3. In some embodiments, a set of probes are directed to sequences selected from at least one, at least two, at least three, at least four, at least five, at least six, at least seven, at least eight, at least nine, or all of the genomic regions listed in Table 3.

TABLE 3

| Closest Gene | Chromosome Number | Region Start | Region Stop |
|---|---|---|---|
| SLC9A3-AS1 | chr5 | 474858 | 475204 |
| DKK2 | chr4 | 107034039 | 107034696 |
| LOX | chr5 | 122076761 | 122077388 |
| C1QL3 | chr10 | 16521666 | 16521939 |
| CSPG5 | chr3 | 47578577 | 47579390 |
| CCT6B | chr17 | 34961183 | 34962104 |
| ISL2 | chr15 | 76336381 | 76336866 |
| ZSWIM2 | chr2 | 186849081 | 186849342 |
| LINC00599 | chr8 | 9904982 | 9906090 |
| LINC01517 | chr10 | 28722124 | 28722695 |

Table 4 shows colorectal methylation regions overlapping in tissue data and TCGA analysis. In some embodiments, a cancer panel comprises one or more of the regions listed in Table 4. For example, a cancer panel comprises at least one, at least two, at least three, at least four, at least five, at least six, at least seven, at least eight, at least nine, or all of the genomic regions listed in Table 4. In some embodiments, a set of probes are directed to sequences selected from at least one, at least two, at least three, at least four, at least five, at least six, at least seven, at least eight, at least nine, or all of the genomic regions listed in Table 4. These regions are associated with presence of cancer and are associated with colorectal tissue, and when combined with the regions in Table 2 and/or Table 3, are supportive of colorectal cancer detection.

TABLE 4

| Closest Gene | Chromosome Number | Region Start | Region Stop |
|---|---|---|---|
| CRIPAK, UVSSA | chr4 | 1410251 | 1411075 |
| MEOX2 | chr7 | 15685300 | 15688105 |
| LRRN2 | chr1 | 204684180 | 204685942 |
| ZNF177 | chr19 | 9362913 | 9363600 |
| DPYSL2 | chr8 | 26578930 | 26579269 |
| CPNE5 | chr6 | 36839707 | 36841032 |
| PHOX2B | chr4 | 41744645 | 41745232 |
| GLB1L3 | chr11 | 134275700 | 134278165 |
| GRIN2A | chr16 | 10181849 | 10183617 |
| SERPINE2 | chr2 | 224038504 | 224040310 |

ii. Liver Cancer

Table 5 shows liver tissue of origin TCGA analysis methylation regions. In some embodiments, a cancer panel comprises one or more of the regions listed in Table 5. For example, a cancer panel comprises at least one, at least two, at least three, at least four, at least five, at least six, at least seven, at least eight, at least nine, or all of the genomic regions listed in Table 5. In some embodiments, a set of probes are directed to sequences selected from at least one, at least two, at least three, at least four, at least five, at least six, at least seven, at least eight, at least nine, or all of the genomic regions listed in Table 5.

TABLE 5

| Closest Gene | Chromosome Number | Region Start | Region Stop |
|---|---|---|---|
| PAK1 | chr11 | 77411719 | 77412043 |
| SLC2A1 | chr1 | 42924164 | 42925230 |
| ECE1 | chr1 | 21289565 | 21291415 |
| MREG | chr2 | 216013030 | 216013935 |
| PPM1N | chr19 | 45497996 | 45499985 |
| MYADM | chr19 | 53867498 | 53868212 |
| MEF2C | chr5 | 88883708 | 88884660 |
| ZNF827 | chr4 | 145938434 | 145939260 |

TABLE 5-continued

| Closest Gene | Chromosome Number | Region Start | Region Stop |
|---|---|---|---|
| ZNF510 | chr9 | 96777400 | 96778505 |
| TRAPPC11 | chr4 | 183722761 | 183723261 |

Table 6 shows liver tissue of origin tissue methylation sequencing methylation regions. In some embodiments, a cancer panel comprises one or more of the regions listed in Table 6. For example, a cancer panel comprises at least one, at least two, at least three, at least four, at least five, at least six, at least seven, at least eight, at least nine, or all of the genomic regions listed in Table 6. In some embodiments, a set of probes are directed to sequences selected from at least one, at least two, at least three, at least four, at least five, at least six, at least seven, at least eight, at least nine, or all of the genomic regions listed in Table 6.

TABLE 6

| Closest Gene | Chromosome Number | Region Start | Region Stop |
|---|---|---|---|
| SLC25A36 | chr3 | 140942215 | 140942681 |
| NXPE3 | chr3 | 101778817 | 101779493 |
| SMG1P3 | chr16 | 21519806 | 21520585 |
| KANK1 | chr9 | 503975 | 504835 |
| NANOS1 | chr10 | 119029236 | 119030177 |
| RBM4 | chr11 | 66638405 | 66639220 |
| EFNB2 | chr13 | 106535692 | 106536388 |
| GPR180 | chr13 | 94601865 | 94602451 |
| SPINT2 | chr19 | 38264214 | 38264616 |
| SLC2A1 | chr1 | 42924235 | 42924973 |

Table 7 shows liver methylation regions overlapping in tissue data and TCGA analysis. In some embodiments, a cancer panel comprises one or more of the regions listed in Table 7. For example, a cancer panel comprises at least one, at least two, at least three, at least four, at least five, at least six, at least seven, at least eight, at least nine, or all of the genomic regions listed in Table 7. In some embodiments, a set of probes are directed to sequences selected from at least one, at least two, at least three, at least four, at least five, at least six, at least seven, at least eight, at least nine, or all of the genomic regions listed in Table 7. These regions are associated with presence of cancer and are associated with liver tissue, and when combined with the regions in Table 5 and/or Table 6, are supportive of liver cancer detection.

TABLE 7

| Closest Gene | Chromosome Number | Region Start | Region Stop |
|---|---|---|---|
| GTDC1 | chr2 | 143936690 | 143937919 |
| TCF24 | chr8 | 66961153 | 66963484 |
| SHISA3 | chr4 | 42397040 | 42398745 |
| AKR1B1 | chr7 | 134458200 | 134459533 |
| HOXA1 | chr7 | 27095185 | 27097167 |
| SPAG6 | chr10 | 22334421 | 22337305 |
| IRF4 | chr6 | 391101 | 392638 |
| PRKCB | chr16 | 23835195 | 23837445 |
| PFKP | chr10 | 3066025 | 3067776 |
| FLT3 | chr13 | 28099335 | 28101240 |

iii. Lung Cancer

Table 8 shows lung tissue of origin TCGA analysis methylation regions. In some embodiments, a cancer panel comprises one or more of the regions listed in Table 8. For example, a cancer panel comprises at least one, at least two, at least three, at least four, at least five, at least six, at least seven, at least eight, at least nine, or all of the genomic regions listed in Table 8. In some embodiments, a set of probes are directed to sequences selected from at least one, at least two, at least three, at least four, at least five, at least six, at least seven, at least eight, at least nine, or all of the genomic regions listed in Table 8.

TABLE 8

| Closest Gene | Chromosome Number | Region Start | Region Stop |
|---|---|---|---|
| CLUAP1 | chr16 | 3500621 | 3501549 |
| PPARGC1B | chr5 | 149730215 | 149731334 |
| GCLC | chr6 | 53544322 | 53545301 |
| ZNF648 | chr1 | 182029665 | 182030206 |
| ITGA6 | chr2 | 172427222 | 172428455 |
| ARHGAP40 | chr20 | 38646114 | 38646491 |
| MARCKS | chr6 | 113858558 | 113859304 |
| PKIG | chr20 | 44531603 | 44532176 |
| G6PC3 | chr17 | 44070557 | 44071133 |
| PPFIBP2 | chr11 | 7513893 | 7514352 |

Table 9 shows lung methylation regions overlapping in tissue data and TCGA analysis. In some embodiments, a cancer panel comprises one or more of the regions listed in Table 9. For example, a cancer panel comprises at least one, at least two, at least three, at least four, at least five, at least six, at least seven, at least eight, at least nine, or all of the genomic regions listed in Table 9. In some embodiments, a set of probes are directed to sequences selected from at least one, at least two, at least three, at least four, at least five, at least six, at least seven, at least eight, at least nine, or all of the genomic regions listed in Table 9. These regions may be associated with presence of cancer and are associated with lung tissue, and when combined with the regions in Table 8, may be supportive of lung cancer detection.

TABLE 9

| Closest Gene | Chromosome Number | Region Start | Region Stop |
|---|---|---|---|
| HOPX | chr4 | 56655120 | 56656970 |
| ITGA4 | chr2 | 181456459 | 181458643 |
| PPP1R16B | chr20 | 38804789 | 38807565 |
| HOXA1 | chr7 | 27095185 | 27097167 |
| TCF24 | chr8 | 66961153 | 66963484 |
| LOC100130992 | chr10 | 22252193 | 22254000 |
| LOC100286906 | chr7 | 155371315 | 155374020 |
| EMILIN2 | chr18 | 2847184 | 2848342 |
| IRF4 | chr6 | 391101 | 392638 |
| OR1F2P | chr16 | 3187792 | 3189855 |

iv. Ovarian Cancer

Table 10 shows ovarian tissue of origin TCGA analysis methylation regions. In some embodiments, a cancer panel comprises one or more of the regions listed in Table 10. For example, a cancer panel comprises at least one, at least two, at least three, at least four, or all of the genomic regions listed in Table 10. In some embodiments, a set of probes are directed to sequences selected from at least one, at least two, at least three, at least four, or all of the genomic regions listed in Table 10.

TABLE 10

| Closest Gene | Chromosome Number | Region Start | Region Stop |
|---|---|---|---|
| UBB | chr17 | 16380613 | 16381454 |
| LYPLAL1-DT | chr1 | 219173767 | 219174230 |
| LEMD1 | chr1 | 205430602 | 205431255 |
| SHF | chr15 | 45200050 | 45201385 |
| RSRP1 | chr1 | 25239575 | 25240220 |

Table 11 shows ovarian tissue of origin tissue methylation sequencing methylation regions. In some embodiments, a cancer panel comprises one or more of the regions listed in Table 11. For example, a cancer panel comprises at least one, at least two, at least three, at least four, at least five, at least six, at least seven, at least eight, at least nine, or all of the genomic regions listed in Table 11. In some embodiments, a set of probes are directed to sequences selected from at least one, at least two, at least three, at least four, at least five, at least six, at least seven, at least eight, at least nine, or all of the genomic regions listed in Table 11.

TABLE 11

| Closest Gene | Chromosome Number | Region Start | Region Stop |
|---|---|---|---|
| LRRC41 | chr1 | 46302590 | 46304060 |
| LRRC41 | chr1 | 46301753 | 46302464 |
| TMEM101 | chr17 | 44014457 | 44015264 |
| ZNF330 | chr4 | 141220899 | 141221572 |
| RAB35 | chr12 | 120086882 | 120087572 |
| SLC25A29 | chr14 | 100285092 | 100285755 |
| TNK2 | chr3 | 195895389 | 195896162 |
| WBP1 | chr2 | 74457263 | 74457800 |
| NUDT19 | chr19 | 32691703 | 32692417 |
| PALLD | chr4 | 168831678 | 168832743 |

Table 12 shows ovarian methylation regions overlapping in tissue data and TCGA analysis. In some embodiments, a cancer panel comprises one or more of the regions listed in Table 12. For example, a cancer panel comprises at least one, at least two, at least three, at least four, at least five, at least six, at least seven, at least eight, at least nine, or all of the genomic regions listed in Table 12. In some embodiments, a set of probes are directed to sequences selected from at least one, at least two, at least three, at least four, at least five, at least six, at least seven, at least eight, at least nine, or all of the genomic regions listed in Table 12. These regions may be associated with presence of cancer and may be associated with ovarian tissue, and when combined with the regions in Table 10 and/or Table 11, may be supportive of ovarian cancer detection.

TABLE 12

| Closest Gene | Chromosome Number | Region Start | Region Stop |
|---|---|---|---|
| LRRC41 | chr1 | 46302590 | 46304060 |
| TMEM101 | chr17 | 44014457 | 44015264 |
| LRRC41 | chr1 | 46301753 | 46302464 |
| TFAP2E | chr1 | 35576535 | 35578237 |
| ZNF154 | chr19 | 57708612 | 57709440 |
| IRF2BP1 | chr19 | 45876550 | 45877420 |
| LYPLAL1-DT | chr1 | 219173767 | 219174230 |
| SCRG1 | chr4 | 173508370 | 173510040 |
| PDXK | chr21 | 43728573 | 43729711 |
| LOC100286906 | chr7 | 155371315 | 155374020 |

v. Pancreatic Cancer

Table 13 shows pancreas tissue of origin tissue methylation sequencing methylation regions. In some embodiments, a cancer panel comprises one or more of the regions listed in Table 13. For example, a cancer panel comprises at least one, at least two, at least three, at least four, at least five, at least six, at least seven, at least eight, at least nine, or all of the genomic regions listed in Table 13. In some embodiments, a set of probes are directed to sequences selected from at least one, at least two, at least three, at least four, at least five, at least six, at least seven, at least eight, at least nine, or all of the genomic regions listed in Table 13.

TABLE 13

| Closest Gene | Chromosome Number | Region Start | Region Stop |
|---|---|---|---|
| ZEB2 | chr2 | 144515729 | 144516316 |
| DISP3 | chr1 | 11478576 | 11479792 |
| EMILIN2 | chr18 | 2847184 | 2848342 |
| CBX8 | chr17 | 79812503 | 79812934 |
| RBFOX3 | chr17 | 79183164 | 79184108 |
| AP3B2 | chr15 | 82680393 | 82680976 |
| KCNA2 | chr1 | 110555424 | 110555713 |
| CTNND2 | chr5 | 11904341 | 11904571 |
| LINC01264 | chr10 | 42932936 | 42933788 |
| HIST1H2BJ | chr6 | 27096849 | 27097190 |

Table 14 shows pancreas methylation regions overlapping in tissue data and TCGA analysis. In some embodiments, a cancer panel comprises one or more of the regions listed in Table 14. For example, a cancer panel comprises at least one, at least two, at least three, at least four, at least five, at least six, at least seven, at least eight, at least nine, or all of the genomic regions listed in Table 14. In some embodiments, a set of probes are directed to sequences selected from at least one, at least two, at least three, at least four, at least five, at least six, at least seven, at least eight, at least nine, or all of the genomic regions listed in Table 14. These regions are associated with presence of cancer and are associated with pancreatic tissue, and when combined with the regions in Table 13, are supportive of pancreatic cancer detection.

TABLE 14

| Closest Gene | Chromosome Number | Region Start | Region Stop |
|---|---|---|---|
| ZNF625 | chr19 | 12155907 | 12156871 |
| LOC392232 | chr8 | 72251140 | 72251956 |
| BASP1-AS1 | chr5 | 17217516 | 17219975 |
| LINC01264 | chr10 | 42932936 | 42933788 |
| KIF7 | chr15 | 89654755 | 89655920 |
| TWIST1 | chr7 | 19112343 | 19112657 |
| SNORD12 | chr20 | 49318252 | 49319561 |
| ARHGEF16 | chr1 | 3393377 | 3394370 |
| SLCO3A1 | chr15 | 91852783 | 91854800 |
| TBX18 | chr6 | 84762839 | 84765672 |

vi. Prostate Cancer

Table 15 lists prostate tissue of origin TCGA analysis methylation regions. In some embodiments, a cancer panel comprises one or more of the regions listed in Table 15. For example, a cancer panel comprises at least one, at least two, at least three, at least four, at least five, at least six, at least seven, at least eight, at least nine, or all of the genomic regions listed in Table 15. In some embodiments, a set of probes are directed to sequences selected from at least one, at least two, at least three, at least four, at least five, at least six, at least seven, at least eight, at least nine, or all of the genomic regions listed in Table 15.

TABLE 15

| Closest Gene | Chromosome Number | Region Start | Region Stop |
|---|---|---|---|
| SERPINB1 | chr6 | 2841095 | 2842039 |
| FBXO30 | chr6 | 145814298 | 145815785 |
| C2orf88 | chr2 | 190180040 | 190181405 |
| FLOT1 | chr6 | 30742095 | 30744911 |
| KLK10 | chr19 | 51018748 | 51020133 |
| SERPINB9 | chr6 | 2902941 | 2903654 |
| TRIP6 | chr7 | 100866785 | 100867795 |
| ARHGAP40 | chr20 | 38601420 | 38602099 |
| ACSF2 | chr17 | 50425455 | 50426576 |
| KLK13 | chr19 | 51064546 | 51065995 |

Table 16 lists prostate tissue of origin tissue methylation sequencing methylation regions. In some embodiments, a cancer panel comprises one or more of the regions listed in Table 16. For example, a cancer panel comprises at least one, at least two, at least three, at least four, at least five, at least six, at least seven, at least eight, at least nine, or all of the genomic regions listed in Table 16. In some embodiments, a set of probes are directed to sequences selected from at least one, at least two, at least three, at least four, at least five, at least six, at least seven, at least eight, at least nine, or all of the genomic regions listed in Table 16.

TABLE 16

| Closest Gene | Chromosome Number | Region Start | Region Stop |
|---|---|---|---|
| MOB3B | chr9 | 27528978 | 27529887 |
| NAV2 | chr11 | 19712785 | 19713147 |
| TSPAN12 | chr7 | 120856772 | 120857377 |
| ABCA1 | chr9 | 104991063 | 104991456 |
| RCCD1 | chr15 | 90954764 | 90955485 |
| C2orf88 | chr2 | 190180174 | 190181293 |
| BMP8B | chr1 | 39789212 | 39789595 |
| KLF12 | chr13 | 74133823 | 74134156 |
| DMBX1 | chr1 | 46488954 | 46489566 |
| RP9P | chr7 | 32942394 | 32942861 |

Table 17 lists prostate methylation regions overlapping in tissue data and TCGA analysis. In some embodiments, a cancer panel comprises one or more of the regions listed in Table 17. For example, a cancer panel comprises at least one, at least two, at least three, at least four, at least five, at least six, at least seven, at least eight, at least nine, or all of the genomic regions listed in Table 17. In some embodiments, a set of probes are directed to sequences selected from at least one, at least two, at least three, at least four, at least five, at least six, at least seven, at least eight, at least nine, or all of the genomic regions listed in Table 17. These regions are associated with presence of cancer and are associated with prostate tissue, and when combined with the regions in Table 15 and/or Table 16, are supportive of prostate cancer detection.

TABLE 17

| Closest Gene | Chromosome Number | Region Start | Region Stop |
|---|---|---|---|
| MOB3B | chr9 | 27528978 | 27529887 |
| IRF2BP1 | chr19 | 45876550 | 45877420 |
| AKR1B1 | chr7 | 134458200 | 134459533 |
| KLK10 | chr19 | 51018748 | 51020133 |
| ZSCAN12 | chr6 | 28399347 | 28400210 |
| RNVU1-8 | chr1 | 147083835 | 147085351 |
| PPP1R16B | chr20 | 38804789 | 38807565 |
| LOC100130298 | chr8 | 60909799 | 60910469 |
| LOC100507557 | chr6 | 145814298 | 145815785 |
| UBXN10 | chr1 | 20185867 | 20186730 |

In an aspect, the present disclosure provides a method for identifying a methylation signature indicative of a biological characteristic, the method comprising: obtaining data for a population comprising a plurality of genomic methylation data sets associated with cell proliferative disorder status, wherein each of said genomic methylation data sets are associated with biological information for a corresponding sample; segregating the methylation data sets into a first group corresponding to one tissue or cell type possessing the biological characteristic and a second group corresponding to a plurality of tissue or cell types not possessing the biological characteristic; matching methylation data from the first group to methylation data from the second group on a site-by-site basis across the genome; identifying a set of CpG sites on a site-by-site basis across the genome that meet a predetermined threshold for establishing differential methylation between the first and second groups; identifying, using the set of CpG sites, target genomic regions comprising at least one, at least two, at least three, or more than three differentially methylated CpGs within about 30 to 300 bp that meet said predetermined criteria, to identify differentially methylated genomic regions that provide the methylation signature indicative of the biological characteristic associated with the presence of a cell proliferative disorder.

In some examples, the target genomic region comprises at least one, at least two, at least three, or more than three differentially methylated CpG sites within a region having a length of about 30 to 150 bp, about 40 to 150 bp, about 50 to 150 bp, about 75 to 150 bp, about 100 to 150 bp, about 150 to 300 bp, about 150 to 250 bp, about 150 to 200 bp, about 200 to 300 bp, or about 250 to 300 bp.

In some examples, the target genomic region comprises at least four differentially methylated CpG sites, at least five differentially methylated CpG sites, at least six differentially methylated CpG sites, at least seven differentially methylated CpG sites, at least eight differentially methylated CpG sites, at least nine differentially methylated CpG sites, at least ten differentially methylated CpG sites, at least 12 differentially methylated CpG sites, or at least 15 differentially methylated CpG sites.

In some embodiments, the method further comprises validating the extended target genomic regions by testing for differential methylation within the extended target genomic regions using DNA from at least one independent sample possessing the biological trait and DNA from at least one independent sample not possessing the biological sample.

In some embodiments, the identifying further comprises limiting the set of CpG sites to CpG sites that further exhibit differential methylation with peripheral blood mononuclear cells from a control sample.

In some embodiments, the predetermined threshold is at least about 50% methylation in the first group.

In some embodiments, the predetermined threshold is a difference in average methylation between the first and second groups of at least about 0.3.

In some embodiments, the biological trait comprises malignancy.

In some embodiments, the biological trait comprises a cancer type.

In some embodiments, the biological trait comprises a cancer stage.

In some embodiments, the biological trait comprises a cancer classification.

In some embodiments, the cancer classification comprises a cancer grade.

In some embodiments, the cancer classification comprises a histological classification.

In some embodiments, the biological trait comprises a metabolic profile.

In some embodiments, the biological trait comprises a mutation.

In some embodiments, the mutation is a disease-associated mutation.

In some embodiments, the biological trait comprises a clinical outcome.

In some embodiments, the biological trait comprises a drug response.

In some embodiments, the method further comprises designing a plurality of PCR primers pairs to amplify portions of the extended target genomic regions, each of the portions comprising at least one differentially methylated CpG site.

In some embodiments, the designing of the plurality of primer pairs comprising converting non-methylated cytosines uracil, to simulate cytosine to uracil conversion, and designing the primer pairs using the converted sequence.

In some embodiments, the primer pairs are designed to have a methylation bias.

In some embodiments, the primer pairs are methylation-specific.

In some embodiments, the primer pairs have no CpG residues within them having no preference for methylation status.

In an aspect, the present disclosure provides a method for synthesizing primer pairs specific to a methylation signature, the method comprising: carrying out a method of the present disclosure, and synthesizing the designed primer pairs.

IV. Nucleic Acid Conversion and Methylation Sequencing

A. Nucleic Acid Treatment

Various methods are available for methylation sequencing that include chemical-based and enzymatic-based conversion of nucleic acid bases to distinguish methylated from unmethylated cytosines in a nucleic acid sequence. These assays allow for determination of the methylation state of one or a plurality of CpG dinucleotides (e.g., CpG islands) within a DNA sequence. Such assays may comprise, among other techniques, DNA sequencing of bisulfite-treated DNA, or enzymatic-treated DNA, polymerase chain reaction (PCR) (for sequence-specific amplification), quantitative PCR (qPCR), or digital droplet PCR (ddPCR), Southern blot analysis. In various examples, DNA in a biological sample is treated in such a manner that cytosine bases which are unmethylated at the 5'-position are converted to uracil, thymine, or another base which is dissimilar to cytosine in terms of hybridization behavior. This process may be referred to as "conversion".

In some embodiments, a reagent converts cytosine bases which are unmethylated at the 5'-position to uracil, thymine, or another base which is dissimilar to cytosine in terms of hybridization behavior.

Bisulfite modification of DNA generally refers to a tool used to assess CpG methylation status. A method for analyzing DNA for the presence of 5-methylcytosine may be based upon the reaction of bisulfite with cytosine whereby, upon subsequent alkaline desulfonation, cytosine is converted to uracil which corresponds to thymine with respect to base pairing behavior. For example, genomic sequencing may be adapted for analysis of DNA methylation patterns and 5-methylcytosine distribution by using bisulfite treatment (e.g., as described by Frommer et al., Proc. Natl. Acad. Sci. USA 89:1827-1831, 1992, the contents of which are incorporated herein by reference). Significantly, however, 5-methylcytosine may remain unmodified under these conditions. Consequently, the original DNA may be converted in such a manner that methylcytosine, which originally could not be distinguished from cytosine by hybridization behavior, can now be detected as the only remaining cytosine using various molecular biological techniques, for example, by amplification and hybridization, or by sequencing. In various examples, other reagents may affect the same result as bisulfite modification useful for methylation sequencing.

A direct sequencing method may employ bisulfite-treated DNA amplified with PCR useful with whole-genome bisulfite sequencing (WGBS) or targeted bisulfite sequencing.

Targeted Bisulfite Sequencing is a commercially available NGS method used to evaluate site-specific DNA methylation changes. Probes may be designed to be strand-specific as well as bisulfite-specific. Both methylated and unmethylated sequences may be amplified. The process may be similar to pyrosequencing, but may offer a much higher throughput overall. In some embodiments, next-generation sequencing platforms are used to deliver large amounts of useful DNA methylation information (e.g., EPIGENTEK, Farmingdale, N.Y. and ZYMO RESEARCH, Irvine, Calif.). The methylation analysis at single-base resolution of individual cytosine in DNA may be facilitated by bisulfite treatment of DNA followed by PCR amplification of targeted region, library construction, and sequencing of the amplicon regions. Specific primers may be designed for the region of interest and cytosine methylation changes may be evaluated within that region. Each DNA methylation site of interest may be assessed at high-sequencing depth of coverage for accurate, quantitative, and single-base resolution data output.

Enzymatic methyl sequencing (EM-seq) may rely on enzymatic conversion of nucleic acids for methylome analysis. The process of generating EM-seq libraries may not damage DNA in the same way as bisulfite sequencing. EM-seq libraries may give higher PCR yields despite using fewer PCR cycles for all DNA input amounts, indicating that less DNA is lost during enzymatic treatment and library preparation, as compared to whole genome bisulfite sequencing (WGBS). Reduced PCR cycles, in turn, may translate into more complex libraries and fewer PCR duplicates during sequencing. EM-seq libraries also may have larger average insert sizes than WGBS which further supports the fact that DNA remains intact. In the EM-seq workflow, TET2 oxidizes 5-mC and 5-hmC, providing protection from deamination by APOBEC in the next operation. In contrast, unmodified cytosines may be deaminated to uracils. In some embodiments, the targeted method comprises enzymatic conversion of nucleic acid (TEM-seq). In some embodiments, the methylation sequencing methods may be accomplished with the NEBNEXT Enzymatic Methyl-seq (New England Biolabs, Ipswich, Mass.) which may be useful for identification of 5-mC and 5-hmC.

In another example, 5-hmC may be also detected using TET-assisted bisulfite sequencing (TAB-seq) (e.g., as described by Yu, M., et al. (2012). Nat. Protoc. 7, 2159-2170, the contents of which are incorporated herein by reference) (WiseGene; Illumina). Fragmented DNA may be enzymatically modified using sequential T4 Phage β-glucosyltransferase (T4-BGT), and then Ten-eleven translocation (TET) dioxygenase treatments before the addition of sodium bisulfite. T4-BGT is used to glucosylate 5-hmC to form β-glucosyl-5-hydroxymethylcytosine (5-ghmC) and TET is then used to oxidize 5-mC to 5-caC. Only 5-ghmC is protected from subsequent deamination by sodium bisulfite and this enables 5-hmC to be distinguished from 5-mC by sequencing.

Oxidative bisulfite sequencing (oxBS) provides another method to distinguish between 5-mC and 5-hmC (e.g., as described by Booth, M. J., et al., 2012 Science 336: 934-937, the contents of which are incorporated herein by reference). The oxidation reagent potassium perruthenate converts 5-hmC to 5-formylcytosine (5-fC) and subsequent sodium bisulfite treatment deaminates 5-fC to uracil. 5-mC remains unchanged and can therefore be identified using this method.

APOBEC-coupled epigenetic sequencing (ACE-seq) excludes bisulfite conversion altogether and relies on enzymatic conversion to detect 5-hmC (e.g., as described by Schutsky, E. K., et al., Nat. Biotechnol., 2018 Oct. 8, the contents of which are incorporated herein by reference). With this method, T4-BGT glucosylates 5-hmC to 5-ghmC, which protects 5-hmC from deamination by Apolipoprotein B mRNA editing enzyme subunit 3A (APOBEC3A). Cytosine. 5-mC is deaminated by APOBEC3A and sequenced as thymine.

In another example, a bisulfite-free and base-level-resolution sequencing method, TET-assisted pyridine borane sequencing (TAPS), may be used for detection of 5-mC and 5-hmC. TAPS combines ten-eleven translocation (TET) oxidation of 5-mC and 5-hmC to 5-carboxylcytosine (5-caC) with pyridine borane reduction of 5-caC to dihydrouracil (DHU). Subsequent PCR converts DHU to thymine, enabling a C-to-T transition of 5-mC and 5-hmC. TAPS detects modifications directly with high sensitivity and specificity, without affecting unmodified cytosines (e.g., as described by Liu, Y., et al. Nat Biotechnol. 2019 April; 37(4):424-429, the contents of which are incorporated herein by reference).

TET-assisted 5-methylcytosine sequencing (TAmC-seq) enriches for 5-mC loci and utilizes two sequential enzymatic reactions followed by an affinity pull-down (Zhang, L. 2013, Nat Commun 4: 1517). Fragmented DNA is treated with T4-BGT which protects 5-hmC by glucosylation. The enzyme mTET1 is then used to oxidize 5-mC to 5-hmC, and T4-BGT labels the newly formed 5-hmC using a modified glucose moiety (6-N3-glucose). Click chemistry may be used to introduce a biotin tag which enables enrichment of 5-mC-containing DNA fragments for detection and genome wide profiling.

B. Next-Generation Sequencing

In some embodiments, the generating of sequencing reads is carried out by next-generation sequencing (NGS). NGS may permit a high depth of reads to be achieved for a given region. Such high-throughput methods include, for example, Illumina (Solexa) sequencing, DNB-Sequencer T7 or G400 (MGI Tech Co., Ltd), GenapSys sequencing (GenapSys, Inc.), Roche 454 sequencing (Roche Sequencing Solutions, Inc.), Ion Torrent sequencing (Thermo Fisher Scientific), and SOLiD sequencing (Thermo Fisher Scientific). The number of sequencing reads may be adjusted depending on DNA input amount and depth of data required for analysis.

In some embodiments, the generating of sequencing reads is carried out simultaneously for samples obtained from multiple patients, wherein the cell-free nucleic acid fragments are barcoded for each patient. Simultaneous generation of sequencing reads permits parallel analysis of a plurality of patients in one sequencing run.

In another aspect, the present disclosure provides a kit for detecting a tumor comprising reagents for carrying out the aforementioned method and instructions for detecting the tumor signals. Reagents may include, for example, primer sets, PCR reaction components, and/or sequencing reagents.

C. Targeted Sequencing

In targeted methylation sequencing approaches, targeted regions in a biological sample such as cfDNA may be analyzed to determine the methylation state of the target gene sequences. In some embodiments, the target region comprises, or hybridizes under stringent conditions to, contiguous nucleotides of target regions of interest, such as at least about 16 contiguous nucleotides of a target region of interest. In different examples, targeted sequencing may be accomplished using hybridization capture and amplicon sequencing approaches.

D. Hybridization Capture

The hybridization method provided herein may be used in various formats of nucleic acid hybridizations, such as in-solution hybridization and such as hybridization on a solid support (e.g., Northern, Southern, and in situ hybridization on membranes, microarrays, and cell/tissue slides). In particular, the method is suitable for in-solution hybrid capture for target enrichment of certain types of genomic DNA sequences (e.g., exons) employed in targeted next-generation sequencing. For hybrid capture approaches, a cell-free nucleic acid sample may be subjected to library preparation. As used herein, "library preparation" comprises end-repair, A-tailing, adapter ligation, or any other preparation performed on the cell-free DNA to permit subsequent sequencing of DNA. In certain examples, a prepared cell-free nucleic acid library sequence contains adapters, sequence tags, or index barcodes that are ligated onto cell-free nucleic acid sample molecules. Various commercially available kits may be used to facilitate library preparation for next-generation sequencing approaches. Next-generation sequencing library construction may comprise preparing nucleic acids targets using a coordinated series of enzymatic reactions to produce a random collection of DNA fragments of specific size for high throughput sequencing. Advances and the development of various library preparation technologies have expanded the application of next-generation sequencing to fields such as transcriptomics and epigenetics.

Improvements in sequencing technologies have resulted in changes and improvements to library preparation. Next-generation sequencing library preparation kits, developed by companies such as Agilent, Bioo Scientific, Kapa Biosystems, New England Biolabs, Illumina, Life Technologies, Pacific Biosciences, and Roche may provide consistency and reproducibility to various molecular biology reactions that ensure compatibility with the latest NGS instrument technology.

In various examples for targeted capture gene panels, various library preparation kits may be selected from Nextera Flex (Illumina), IonAmpliseq (Thermo Fisher Scientific), Genexus (Thermo Fisher Scientific), Agilent ClearSeq (Illumina), Agilent SureSelect Capture (Illumina), Archer FusionPlex (Illumina), BiooScientific NEXTflex (Illumina), IDT xGen (Illumina), Illumina TruSight (Illumina), Nimblegene SeqCap (Illumina), and Qiagen GeneRead (Illumina).

In some embodiments, the hybrid capture method is carried out on the prepared library sequences using specific probes. In some embodiments, the term "specific probe", as used herein, generally refers to a probe that is specific for known methylation sites. In some embodiments, the specific probes are designed based on using human genome as a reference sequence and using specified genomic regions known to have methylation sites as target sequences. Specifically, genomic regions known to have methylation sites may comprise at least one of the following: a promoter region, a CpG island region, a CGI shore region, and an imprinted gene region. Therefore, when carrying out the hybrid capture by using the specific probes of some embodiments, the sequences in the sample genome which are complimentary to the target sequences, e.g., regions in the sample genome known to have methylation sites (which are also referred to as "specified genomic regions" herein) may be captured efficiently.

In some embodiments, the methylated regions described herein are used for designing the specific probes. In some embodiments, the specific probes are designed using commercially available methods such as for example an eArray system. The length of the probes may be sufficient to hybridize with sufficient specificity to the methylated region of interest. In various examples, the probe is a 10-mer, 11-mer, 12-mer, 13-mer, 14-mer 15-mer, 16-mer, 17-mer, 18-mer, 19-mer, or 20-mer.

The regions listed in Tables 1-17 may be screened using database resources (such as gene ontology). According to the principle of complementary base pairing, a single-stranded capture probe may be combined with a single-stranded target sequence complementarily, so as to capture the target region successfully. In some embodiments, the designed probes may be designed as a solid capture chip (wherein the probes are immobilized on a solid support) or be designed as a liquid capture chip (wherein the probes are free in the liquid), however, limited by various factors, such as probe length, probe density, and high cost etc. The solid capture chip is rarely used, while the liquid capture chip is used more frequently.

In some embodiments, compared with normal sequences (where the average content of A, T, C, and G base is 25% each, respectively), GC-rich sequences (where the content of GC bases is higher than 60%) in nucleic acid may lead to the reduction of capture efficiency because of the molecular structure of C and G bases. For the key research regions, for example, CGI regions (CpG islands), designing an increased amount of the probes to obtain sufficient and accurate CGI data may be recommended.

E. Amplicon-Based Sequencing

Fragments of the converted DNA may be amplified. In some embodiments, the amplifying is carried out with primers designed to anneal to methylation converted target sequences having at least one methylated site therein. Methylation sequencing conversion results in unmethylated cytosines being converted to uracil, while 5-methylcytosine is unaffected. "Converted target sequences" may thus be understood as sequences in which cytosines known to be methylation sites are fixed as "C" (cytosine), while cytosines known to be unmethylated may be fixed as "U" (uracil; which may be treated as "T" (thymine) for primer design purposes).

In various examples, the source of the DNA may be cell-free DNA from whole blood, plasma, serum, or genomic DNA extracted from cells or tissue. In some embodiments, the size of the amplified fragment is between about 100 and 200 base pairs in length. In some embodiments, the DNA source is extracted from cellular sources (e.g., tissues, biopsies, or cell lines), and the amplified fragment is between about 100 and 350 base pairs in length. In some embodiments, the amplified fragment comprises at least one 20 base pair sequence comprising at least one, at least two, at least three, or more than three CpG dinucleotides. The amplification may be carried out using sets of primer oligonucleotides according to the present disclosure, and may use a heat-stable polymerase. The amplification of several DNA segments may be carried out simultaneously in one and the same reaction vessel. In some embodiments of the method, two or more fragments are amplified simultaneously. For example, the amplification may be carried out using a polymerase chain reaction (PCR).

Primers designed to target such sequences may exhibit a degree of bias towards converted methylated sequences. In some embodiments, the PCR primers are designed to be methylation specific for targeted methylation-sequencing applications, which may allow for greater sensitivity in some applications. For instance, primers may be designed to include a discriminatory nucleotide (specific to a methylated sequence following bisulfite conversion) positioned to achieve optimal discrimination, e.g., in PCR applications. The discriminatory may be positioned at the 3' ultimate or penultimate position.

Primers may be designed to amplify DNA fragments based on the general size range for circulating DNA. Optimizing primer design to take into account target size may increase the sensitivity of the method according to this example. In some embodiments, the primers are designed to amplify DNA fragments 75 to 350 bp in length. The primers may be designed to amplify regions that are about 50 to 200, about 75 to 150, or about 100 or 125 bp in length.

In some embodiments of the method, the methylation status of preselected CpG positions within the nucleic acid sequences may be detected by the amplicon-based approach using of methylation-specific primer oligonucleotides. The use of methylation status specific primers for the amplification of bisulfite treated DNA may allow the differentiation between methylated and unmethylated nucleic acids. MSP primers pairs may contain at least one primer which hybridizes to a converted CpG dinucleotide. Therefore, the sequence of said primers may comprises at least one CpG, TpG, or CpA dinucleotide. MSP primers specific for non-methylated DNA may contain a "T" at the 3' position of the C position in the CpG. Therefore, the base sequence of said primers may be required to comprise a sequence having a length of at least 18 nucleotides which hybridizes to a pretreated nucleic acid sequence and sequences complementary thereto, wherein the base sequence of said oligomers comprises at least one CpG, TpG, or CpA dinucleotide. In some embodiments of the method, the MSP primers comprise between 2 and 5 CpG, TpG, or CpA dinucleotides. In some embodiments, the dinucleotides are located within the 3' half of the primer, e.g., wherein a primer is 18 bases in length the specified dinucleotides are located within the first 9 bases form the 3' end of the molecule. In addition to the CpG, TpG, or CpA dinucleotides, the primers may further comprise several methyl converted bases (e.g., cytosine converted to thymine, or on the hybridizing strand, guanine converted to adenosine). In some embodiments, the primers are designed so as to comprise no more than 2 cytosine or guanine bases.

In some embodiments, each of the regions is amplified in sections using multiple primer pairs. In some embodiments, these sections are non-overlapping. The sections may be immediately adjacent or spaced apart (e.g., spaced apart up to 10, 20, 30, 40, or 50 bp). Since target regions (including CpG islands, CpG shores, and/or CpG shelves) are usually longer than 75 to 150 bp, this example may permit the methylation status of sites across more (or all) of a given target region to be assessed.

Primers may be designed for target regions using suitable tools such as Primer3, Primer3Plus, Primer-BLAST, etc. As discussed, bisulfite conversion results in cytosine converting to uracil and 5'-methyl-cytosine converting to thymine. Thus, primer positioning or targeting may make use of bisulfite converted methylated sequences, depending on the degree of methylation specificity required.

Target regions for amplification may be designed to have at least 10 CpG dinucleotide methylation sites. In some examples, however, amplification of regions having more than 10 CpG methylation site may be advantageous. For instance, a sequence read 300 bp long may have about 10, 20, 30, 40, or 50 CpG methylation sites that are methylated in a nucleic acid sample associated with a cell proliferative disorder. In various examples, the methylation regions identified in Tables 1-17 may have 25, 50, 100, 200, 300, 400, or 500 CpG methylation sites that are methylated in a nucleic acid sample associated with a cell proliferative disorder. In some embodiments, the primers are designed to amplify DNA fragments comprising 3 to 20 CpG methylation sites in a targeted region. Overall, this approach may permit a larger number of methylation sites to be queried within a single sequencing read and may provide additional certainty (exclusion of false positives) because multiple concordant methylations may be detected within a single sequencing read. In some embodiments, the tumor signals comprise more than two methylated regions selected from Tables 1-17. Detection of multiple tumor signals, in this example, may increase confidence in tumor detection. Such signals may be at the same or at different sites. In some embodiments, the detection of more than one of the tumor signals at the same region is indicative of a tumor.

In some embodiments, the number of CpG sites in an identified methylated region may be modeled between two populations having a different characteristic of a cell proliferative disorder to identify a methylation threshold where the number of CpG sites in a region that exceeds the threshold is indicative of a cell proliferative disorder.

In various examples, the number of CpG sites in an identified methylated region that indicates cancer is 4, 5, 6, 7, 8, 9, 10, 11, 12, 13, 14, 15, 16, 17, or 18, where the presence of methylated CpGs that exceeds this identified number is indicative of cancer and may be used as an input feature into a machine learning model used as a classifier to stratify a population into healthy individuals and those having cancer.

Detection of multiple tumor signals indicative of methylation at the same site in the genome, in this example, may increase confidence in tumor detection. Detection of methylation at adjacent sites in the genome may also increase confidence in tumor detection, even if the signals are derived from different sequencing reads. Detection of methylation at adjacent sites in the genome reflects another type of signal concordance. In some embodiments, the detection of adjacent or overlapping tumor signals across at least two different sequencing reads is indicative of a tumor. In some embodiments, the adjacent or overlapping tumor signals are within the same CpG island. In some embodiments, the detection of 3 to 34 proximal methylated sites in a cell-free DNA fragment is indicative of a tumor. In some embodiments, the detection of 3 to 34 methylated CpG sites in a fragment is used to identify a threshold to distinguish between a population of individuals having a characteristic (e.g., healthy, disease, or stage of disease). In some embodiments, the detection of about 4 to 10, about 4 to 15, about 10 to 20, about 15 to 20, about 15 to 25, about 20 to 25, about 20 to 34, about 25 to 34, or about 30 to 34 methylated proximal CpG sites in a read fragment is used to identify a threshold to distinguish between a population of individuals having a characteristic (e.g., healthy, disease, or stage of disease). As used herein, the term "proximal CpG site" refers to CpG sites that are adjacent or within about 2 to 10 CpG sites of each other and where the CpG sites on the same nucleic acid fragment in a cell-free nucleic acid sample.

In some embodiments, the amplification is carried out with more than 100 primer pairs. The amplification may be carried out with about 10, about 20, about 30, about 40, about 50, about 60, about 70, about 80, about 90, about 100, about 110, about 120, about 130, about 140, about 150, or more primer pairs. In some embodiments, the amplification is a multiplex amplification. Multiplex amplification permits large amount of methylation information to be gathered from many target regions in the genome in parallel, even from cfDNA samples in which DNA is generally not plentiful. The multiplexing may be scaled up to a platform such as ION AmpliSeq, in which, e.g., up to about 24,000 amplicons may be queried simultaneously. In some embodiments, the amplification is nested amplification. A nested amplification may improve sensitivity and specificity.

Further, another rapid and robust protocol for the parallel examination of multiple methylated sequences termed simultaneous targeted methylation sequencing (sTM-Seq). Key features of this technique include the elimination of the need for large amounts of high-molecular weight DNA and the nucleotide specific distinction of both 5-methylcytosine (5-mC) and 5-hydroxymethylcytosine (5-hmC). Moreover, sTM-Seq may be scalable and may be used to investigate multiple loci in dozens of samples within a single sequencing run. Freely available web-based software and universal primers for multipurpose barcoding, library preparation, and customized sequencing make sTM-Seq affordable, efficient, and widely applicable. (as described by Asmus, N. et al., Curr Protoc Hum Genet. 2019 April; 101(1), the contents of which are incorporated herein by reference).

Generally, the methods and systems provided herein may be useful for preparation of cell-free polynucleotide sequences to a downstream application sequencing reaction. In some embodiments, a sequencing method is classic Sanger sequencing. Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next-generation sequencing, Single Molecule Sequencing by Synthesis (SMSS)(Helicos), massively-parallel sequencing, Clonal Single Molecule Array (Solexa), shotgun sequencing, Maxim-Gilbert sequencing, primer walking, and any other sequencing methods.

Pyrosequencing is a real-time sequencing technology based on luminometric detection of pyrophosphate release upon nucleotide incorporation which is suitable for simultaneous analysis and quantification of the methylation degree of several CpG positions. After conversion of genomic DNA, a region of interest may be amplified by polymerase chain reaction (PCR) with one of the two primers being biotinylated. The PCR-generated template may be rendered single stranded and a Pyrosequencing primer is annealed to analyze quantitatively CpG positions. After bisulfite treatment and PCR, the degree of each methylation at each CpG position in a sequence may be determined from the ratio of T and C signals reflecting the proportion of unmethylated and methylated cytosines at each CpG site in the original sequence.

V. Classifiers, Machine Learning Models & Systems

In various examples, methylation sequencing features may be used as input datasets into trained algorithms (e.g., machine learning models or classifiers) to identify correlations between sequence composition and patient groups. Examples of such patient groups include presence of diseases or conditions, stages, subtypes, responders vs. non-responders, and progressors vs. non-progressors. In various examples, feature matrices may be generated to compare samples obtained from individuals with known conditions or characteristics. In some embodiments, samples may be obtained from healthy individuals, or individuals who do not have any of the known indications and samples from patients known to have cancer.

As used herein, relating to machine learning and pattern recognition, the term "feature" generally refers to an individual measurable property or characteristic of a phenomenon being observed. The concept of "feature" may be related to that of explanatory variable used in statistical techniques such as for example, but not limited to, linear regression and logistic regression. Features may numeric, but structural features such as strings and graphs may be used in syntactic pattern recognition.

The term "input features" (or "features"), as used herein, generally refers to variables that are used by the trained algorithm (e.g., model or classifier) to predict an output classification (label) of a sample, e.g., a condition, sequence content (e.g., mutations), suggested data collection operations, or suggested treatments. Values of the variables may be determined for a sample and used to determine a classification.

In various examples, input features of genetic data may include: aligned variables that relate to alignment of sequence data (e.g., sequence reads) to a genome and non-aligned variables, e.g., that relate to the sequence content of a sequence read, a measurement of protein or autoantibody, or the mean methylation level at a genomic region. Input features may be genetic features such as, chromatin accessibility (for example transcription factor binding features), nucleosome positioning features (for example V-plot measures and cfDNA measurement over a transcription start site), or cell type deconvolution (for example FREE-C deconvolution). Metrics that may be used in methylation analysis include, but are not limited to, base wise methylation percent for CpG, CHG, CHH, conversion efficiency (100−Mean methylation percent for CHH), hypomethylated blocks, methylation levels (global mean methylation for CPG, CHH, CHG, fragment length, fragment midpoint, number of methylated CpGs per fragment, fraction of CpG methylation to total CpG per fragment, fraction of CpG methylation to total CpG per region, fraction of CpG methylation to total CpG in panel, dinucleotide coverage (normalized coverage of di-nucleotide), evenness of coverage (unique CpG sites at 1× and 10× mean genomic coverage (for S4 runs), mean CpG coverage (depth) globally, and mean coverage at CpG islands, CGI shelves, or CGI shores. These metrics may be used as feature inputs for machine learning methods and models.

For a plurality of assays, the system may identify feature sets to be analyzed using a trained algorithm (e.g., machine learning model or classifier). The system may perform an assay on each molecule class and forms a feature vector from the measured values. The system may analyze the feature vector using the machine learning model and obtain an output classification of whether the biological sample has a specified property.

In some embodiments, the machine learning model outputs a classifier capable of distinguishing between two or more groups or classes of individuals or features in a population of individuals or features of the population. In some embodiments, the classifier is a trained machine learning classifier.

In some embodiments, the informative loci or features of biomarkers in a cancer tissue are assayed to form a profile. Receiver-operating characteristic (ROC) curves may be generated by plotting the performance of a particular feature (e.g., any of the biomarkers described herein and/or any item of additional biomedical information) in distinguishing between two populations (e.g., individuals responding and not responding to a therapeutic agent). In some embodiments, the feature data across the entire population (e.g., the cases and controls) are sorted in ascending order based on the value of a single feature.

In various examples, the specified property is selected from healthy vs. cancer, disease subtype, disease stage, progressor vs. non-progressor, and responder vs. non-responder.

A. Data Analysis

In some examples, the present disclosure provides a system, method, or kit having data analysis realized in software application, computing hardware, or both. In various examples, the analysis application or system comprises at least a data receiving module, a data pre-processing module, a data analysis module (which can operate on one or more types of genomic data), a data interpretation module, or a data visualization module. In some embodiments, the data receiving module can comprise computer systems that connect laboratory hardware or instrumentation with computer systems that process laboratory data. In some embodiments, the data pre-processing module comprise hardware systems or computer software that performs operations on the data in preparation for analysis. Examples of operations that may be applied to the data in the pre-processing module include affine transformations, denoising operations, data cleaning, reformatting, or subsampling. A data analysis module, which may be specialized for analyzing genomic data from one or more genomic materials, may, for example, perform probabilistic and statistical analysis on assembled genomic sequences to identify abnormal patterns related to a disease, pathology, state, risk, condition, or phenotype. A data interpretation module may use analysis methods, for example, drawn from statistics, mathematics, or biology, to support understanding of the relation between the identified abnormal patterns and health conditions, functional states, prognoses, or risks. A data visualization module may use methods of mathematical modeling, computer graphics, or rendering to create visual representations of data that can facilitate the understanding or interpretation of results.

In various examples, machine learning methods may be applied to distinguish samples in a population of samples. In some embodiments, machine learning methods are applied to distinguish samples between healthy and advanced disease (e.g., adenoma) samples.

In some embodiments, the one or more machine learning operations used to train the prediction engine are selected from the group consisting of: a generalized linear model, a generalized additive model, a non-parametric regression operation, a random forest classifier, a spatial regression operation, a Bayesian regression model, a time series analysis, a Bayesian network, a Gaussian network, a decision tree learning operation, an artificial neural network, a recurrent neural network, a convolutional neural network, a reinforcement learning operation, linear or non-linear regression operations, a support vector machine, a clustering operation, and a genetic algorithm operation.

In various examples, computer processing methods are selected from the group consisting of logistic regression, multiple linear regression (MLR), dimension reduction, partial least squares (PLS) regression, principal component regression, autoencoders, variational autoencoders, singular value decomposition, Fourier bases, wavelets, discriminant analysis, support vector machine, decision tree, classification and regression trees (CART), tree-based methods, random forest, gradient boost tree, logistic regression, matrix factorization, multidimensional scaling (MDS), dimensionality reduction methods, t-distributed stochastic neighbor embedding (t-SNE), multilayer perceptron (MLP), network clustering, neuro-fuzzy, and artificial neural networks.

In some examples, the methods disclosed herein can include computational analysis on nucleic acid sequencing data of samples from an individual or from a plurality of individuals.

B. Classifier Generation

In an aspect, the disclosed systems and methods provide a classifier generated based on feature information derived from methylation sequence analysis from biological samples of cfDNA. The classifier may form part of a predictive engine for distinguishing groups in a population based on sequence features identified in biological samples such as cfDNA.

In some embodiments, a classifier is created by normalizing the sequence information by formatting similar portions of the sequence information into a unified format and a unified scale; storing the normalized sequence information in a columnar database; training a prediction engine by applying one or more one machine learning operations to the stored normalized sequence information, the prediction engine mapping, for a particular population, a combination of one or more features; applying the prediction engine to the accessed field information to identify an individual associated with a group; and classifying the individual into a group.

In some embodiments, a hierarchy is created by normalizing the sequence information by formatting similar portions of the sequence information into a unified format and a unified scale; storing the normalized sequence information in a columnar database; training a prediction engine by applying one or more one machine learning operations to the stored normalized sequence information, the prediction engine mapping, for a particular population, a combination of one or more features; applying the prediction engine to the accessed field information to identify an individual associated with a group; and classifying the individual into a group.

Specificity, as used herein, generally refers to "the probability of a negative test among those who are free from the disease". Specificity may be calculated by the number of disease-free persons who tested negative divided by the total number of disease-free individuals.

In various examples, the model, classifier, or predictive test has a specificity of at least 40%, at least 45%, at least 50%, at least 55%, at least 60%, at least 65%, at least 70%, at least 75%, at least 80%, at least 85%, at least 90%, at least 95%, or at least 99%.

Sensitivity, as used herein, generally refers to "the probability of a positive test among those who have the disease". Sensitivity may be calculated by the number of diseased individuals who tested positive divided by the total number of diseased individuals.

In various examples, the model, classifier, or predictive test has a sensitivity of at least 40%, at least 45%, at least 50%, at least 55%, at least 60%, at least 65%, at least 70%, at least 75%, at least 80%, at least 85%, at least 90%, at least 95%, or at least 99%.

C. Digital Processing Device

In some examples, the subject matter described herein may include a digital processing device or use of the same. In some examples, the digital processing device may include one or more hardware central processing units (CPU), graphics processing units (GPU), or tensor processing units (TPU) that carry out the device's functions. In some examples, the digital processing device may include an operating system configured to perform executable instructions.

In some examples, the digital processing device may optionally be connected a computer network. In some examples, the digital processing device may be optionally connected to the Internet. In some examples, the digital processing device may be optionally connected to a cloud computing infrastructure. In some examples, the digital processing device may be optionally connected to an intranet. In some examples, the digital processing device may be optionally connected to a data storage device.

Non-limiting examples of suitable digital processing devices include server computers, desktop computers, laptop computers, notebook computers, sub-notebook computers, netbook computers, netpad computers, set-top computers, handheld computers, Internet appliances, mobile smartphones, and tablet computers. Suitable tablet computers may include, for example, those with booklet, slate, and convertible configurations.

In some examples, the digital processing device may include an operating system configured to perform executable instructions. For example, the operating system may include software, including programs and data, which manages the device's hardware and provides services for execution of applications. Non-limiting examples of operating systems include Ubuntu, FreeBSD, OpenBSD, NetBSD®, Linux, Apple® Mac OS X Server®, Oracle® Solaris®, Windows Server®, and Novell® NetWare®. Non-limiting examples of suitable personal computer operating systems include Microsoft® Windows®, Apple® Mac OS X®, UNIX®, and UNIX-like operating systems such as GNU/Linux®. In some examples, the operating system may be provided by cloud computing, and cloud computing resources may be provided by one or more service providers.

In some examples, the device can include a storage and/or memory device. The storage and/or memory device may be one or more physical apparatuses used to store data or programs on a temporary or permanent basis. In some examples, the device may be volatile memory and require power to maintain stored information. In some examples, the device may be non-volatile memory and retain stored information when the digital processing device is not powered. In some examples, the non-volatile memory may include flash memory. In some examples, the non-volatile memory may include dynamic random-access memory (DRAM). In some examples, the non-volatile memory may include ferroelectric random access memory (FRAM). In some examples, the non-volatile memory may include phase-change random access memory (PRAM).

In some examples, the device may be a storage device including, for example, CD-ROMs, DVDs, flash memory devices, magnetic disk drives, magnetic tapes drives, optical disk drives, and cloud computing-based storage. In some examples, the storage and/or memory device may be a combination of devices such as those disclosed herein. In some examples, the digital processing device may include a display to send visual information to a user. In some examples, the display may be a cathode ray tube (CRT). In some examples, the display may be a liquid crystal display (LCD). In some examples, the display may be a thin film transistor liquid crystal display (TFT-LCD). In some examples, the display may be an organic light emitting diode (OLED) display. In some examples, on OLED display may be a passive-matrix OLED (PMOLED) or active-matrix OLED (AMOLED) display. In some examples, the display may be a plasma display. In some examples, the display may be a video projector. In some examples, the display may be a combination of devices such as those disclosed herein.

In some examples, the digital processing device may include an input device to receive information from a user. In some examples, the input device may be a keyboard. In some examples, the input device may be a pointing device including, for example, a mouse, trackball, track pad, joystick, game controller, or stylus. In some examples, the input device may be a touch screen or a multi-touch screen. In some examples, the input device may be a microphone to capture voice or other sound input. In some examples, the input device may be a video camera to capture motion or visual input. In some examples, the input device may be a combination of devices such as those disclosed herein.

D. Non-Transitory Computer-Readable Storage Medium

In some examples, the subject matter disclosed herein may include one or more non-transitory computer-readable storage media encoded with a program including instructions executable by the operating system of an optionally networked digital processing device. In some examples, a computer-readable storage medium may be a tangible component of a digital processing device. In some examples, a computer-readable storage medium may be optionally removable from a digital processing device. In some examples, a computer-readable storage medium may include, for example, CD-ROMs, DVDs, flash memory devices, solid state memory, magnetic disk drives, magnetic tape drives, optical disk drives, cloud computing systems and services, and the like. In some examples, the program and instructions may be permanently, substantially permanently, semi-permanently, or non-transitorily encoded on the media.

E. Computer Systems

The present disclosure provides computer systems that are programmed to implement methods described herein. FIG. 1 shows a computer system 101 that may be programmed or otherwise configured to store, process, identify, or interpret patient data, biological data, biological sequences, and reference sequences. The computer system 101 may process various aspects of patient data, biological data, biological sequences, or reference sequences of the present disclosure (FIG. 1). The computer system 101 may be an electronic device of a user or a computer system that is remotely located with respect to the electronic device. The electronic device may be a mobile electronic device.

The computer system 101 may comprise a central processing unit (CPU, also "processor" and "computer processor" herein) 105, which may be a single core or multi core processor, or a plurality of processors for parallel processing. The computer system 101 may also comprises memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120, and peripheral devices 125 may be in communication with the CPU 105 through a communication bus (solid lines), such as a motherboard. The storage unit 115 may be a data storage unit (or data repository) for storing data. The computer system 101 may be operatively coupled to a computer network ("network") 130 with the aid of the communication interface 120. The network 130 may be the Internet, an internet and/or extranet, or an intranet and/or extranet that is in communication with the Internet. The network 130, in some examples, may be a telecommunication and/or data network. The network 130 may include one or more computer servers, which may enable distributed computing, such as cloud computing. The network 130, in some examples with the aid of the computer system 101, may implement a peer-to-peer network, which may enable devices coupled to the computer system 101 to behave as a client or a server.

The CPU 105 may execute a sequence of machine-readable instructions, which may be embodied in a program or software. The instructions may be stored in a memory location, such as the memory 110. The instructions may be directed to the CPU 105, which may subsequently program or otherwise configure the CPU 105 to implement methods of the present disclosure. Examples of operations performed by the CPU 105 may include fetch, decode, execute, and writeback.

The CPU 105 may be part of a circuit, such as an integrated circuit. One or more other components of the system 101 may be included in the circuit. In some examples, the circuit may be an application specific integrated circuit (ASIC).

The storage unit 115 may store files, such as drivers, libraries, and saved programs. The storage unit 115 may store user data, e.g., user preferences and user programs. The computer system 101, in some examples, may include one or more additional data storage units that may be external to the computer system 101, such as located on a remote server that is in communication with the computer system 101 through an intranet or the Internet.

The computer system 101 may communicate with one or more remote computer systems through the network 130. For instance, the computer system 101 may communicate with a remote computer system of a user. Examples of remote computer systems may include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user may access the computer system 101 via the network 130.

Methods as described herein may be implemented by way of machine (e.g., computer processor) executable code stored on an electronic storage location of the computer system 101, such as, for example, on the memory 110 or electronic storage unit 115. The machine-executable or machine-readable code may be provided in the form of software. During use, the code may be executed by the processor 105. In some examples, the code may be retrieved from the storage unit 115 and stored on the memory 110 for ready access by the processor 105. In some examples, the electronic storage unit 115 may be precluded, and machine-executable instructions are stored on memory 110.

The code may be pre-compiled and configured for use with a machine having a processer adapted to execute the code or may be interpreted or compiled during runtime. The code may be supplied in a programming language that may be selected to enable the code to execute in a pre-compiled, interpreted, or as-compiled fashion.

Aspects of the systems and methods provided herein, such as the computer system 101, may be embodied in programming. Various aspects of the technology may be thought of as "products" or "articles of manufacture", for example, in the form of machine (or processor) executable code and/or associated data that is carried on or embodied in a type of machine readable medium. Machine-executable code may be stored on an electronic storage unit, such as memory (e.g., read-only memory, random-access memory, flash memory) or a hard disk. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements comprises optical, electrical, and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" may refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media may include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 101 may include or be in communication with an electronic display 135 that comprises a user interface (UI) 140 for providing, for example, a nucleic acid sequence, an enriched nucleic acid sample, a methylation profile, an expression profile, and an analysis of a methylation or expression profile. Examples of UI's may include, without limitation, a graphical user interface (GUI) and web-based user interface.

Methods and systems of the present disclosure may be implemented by way of one or more algorithms. An algorithm may be implemented by way of software upon execution by the central processing unit 105. The algorithm can, for example, store, process, identify, or interpret patient data, biological data, biological sequences, and reference sequences.

While certain examples of methods and systems have been shown and described herein, one of skill in the art will realize that these are provided by way of example only and not intended to be limiting within the specification. Numerous variations, changes, and substitutions will now occur to those skilled in the art without departing from the scope described herein. Furthermore, it shall be understood that all aspects of the described methods and systems are not limited to the specific depictions, configurations or relative proportions set forth herein which depend upon a variety of conditions and variables and the description is intended to include such alternatives, modifications, variations, or equivalents.

In some examples, the subject matter disclosed herein can include at least one computer program or use of the same. A computer program can a sequence of instructions, executable in the digital processing device's CPU, GPU, or TPU, written to perform a specified task. Computer-readable instructions may be implemented as program modules, such as functions, objects, Application Programming Interfaces (APIs), data structures, and the like, that perform particular tasks or implement particular abstract data types. In light of the disclosure provided herein, a computer program may be written in various versions of various languages.

The functionality of the computer-readable instructions may be combined or distributed as desired in various environments. In some examples, a computer program can include one sequence of instructions. In some examples, a computer program can include a plurality of sequences of instructions. In some examples, a computer program may be provided from one location. In some examples, a computer program may be provided from a plurality of locations. In some examples, a computer program can include one or more software modules. In some examples, a computer program can include, in part or in whole, one or more web applications, one or more mobile applications, one or more standalone applications, one or more web browser plug-ins, extensions, add-ins, or add-ons, or combinations thereof.

In some examples, the computer processing may be a method of statistics, mathematics, biology, or any combination thereof. In some examples, the computer processing method comprises a dimension reduction method including, for example, logistic regression, dimension reduction, principal component analysis, autoencoders, singular value decomposition, Fourier bases, singular value decomposition, wavelets, discriminant analysis, support vector machine, tree-based methods, random forest, gradient boost tree, logistic regression, matrix factorization, network clustering, and neural network such as convolutional neural networks.

In some examples, the computer processing method may be a supervised machine learning method including, for example, a regression, support vector machine, tree-based method, and network.

In some examples, the computer processing method may be an unsupervised machine learning method including, for example, clustering, network, principal component analysis, and matrix factorization.

F. Databases

In some examples, the subject matter disclosed herein may include one or more databases, or use of the same to store patient data, biological data, biological sequences, or reference sequences. Reference sequences may be derived from a database. In view of the disclosure provided herein, many databases may be suitable for storage and retrieval of the sequence information. In some examples, suitable databases can include, for example, relational databases, non-relational databases, object-oriented databases, object databases, entity-relationship model databases, associative databases, and XML, databases. In some examples, a database may be internet-based. In some examples, a database may be web-based. In some examples, a database may be cloud computing-based. In some examples, a database may be based on one or more local computer storage devices.

In an aspect, the present disclosure provides a non-transitory computer-readable medium comprising instructions that direct a processor to carry out a method disclosed herein.

In an aspect, the present disclosure provides a computing device comprising the computer-readable medium.

In another aspect, the present disclosure provides a system for performing classifications of biological samples comprising:

a) a receiver to receive a plurality of training samples, each of the plurality of training samples having a plurality of classes of molecules, wherein each of the plurality of training samples comprises one or more known labels;

b) a feature module to identify a set of features corresponding to an assay that are operable to be analyzed using the machine learning model for each of the plurality of training samples, wherein the set of features corresponds to properties of molecules in the plurality of training samples, wherein for each of the plurality of training samples, the system is operable to subject a plurality of classes of molecules in the training samples to a plurality of different assays to obtain sets of measured values, wherein each set of measured values is from one assay applied to a class of molecules in the training samples, wherein a plurality of sets of measured values are obtained for the plurality of training samples;

c) an analysis module to analyze the sets of measured values to obtain a training vector for the training samples, wherein the training vector comprises feature values of an N set of features of the corresponding assay, each feature value corresponding to a feature and including one or more measured values, wherein the training vector is formed using at least one feature from at least two of the N sets of features corresponding to a first subset of the plurality of different assays;

d) a labeling module to inform the system on the training vectors using parameters of the machine learning model to obtain output labels for the plurality of training samples;

e) a comparator module to compare the output labels to the known labels of the training samples;

f) a training module to iteratively search for optimal values of the parameters as part of training the machine learning model based on the comparing the output labels to the known labels of the training samples; and g) an output module to provide the parameters of the machine learning model and the set of features for the machine learning model.

VI. Methods of Classifying Subjects in a Population

The disclosed methods are directed to ascertaining genetic and/or epigenetic parameters of genomic DNA associated with cell proliferative disorders via analysis of cfDNA in a subject. The method may be for use in the improved diagnosis, treatment, and monitoring of cell proliferative disorders, more specifically by enabling the improved identification of and differentiation between stages or subclasses of said disorder and the genetic predisposition to said disorders.

In some embodiments, the method comprises analyzing the methylation status of CpG islands, CpG shores, or CpG shelves.

In some embodiments, the method comprises analyzing the methylation state, hemimethylation status, hypermethylation state, or hypomethylation state of a cell-free nucleic acid in a biological sample.

Generally, the present disclosure provides a method for detecting a cell proliferative disorder that may be applied to cell-free samples, e.g., to detect cell-free circulating cell proliferative disorder DNA. The method may utilize detection of methylation signals within a single sequencing read as the basic "positive" cell proliferative disorder signal.

In an aspect, the present disclosure provides a method for detecting a cell proliferative disorder, comprising: extracting DNA from a cell-free sample obtained from a subject, converting at least a portion of the DNA for methyl sequencing, amplifying regions methylated in cancer from the converted DNA, generating sequencing reads from the amplified regions, and detecting cell proliferative disorder signals comprising at least one, at least two, at least three, or more than three methylated regions within a cancer panel, to obtain input features that may be analyzed using a machine learning model to obtain a classifier capable of discriminating between two groups of subjects (e.g., healthy vs. cancer, disease stage, advanced adenoma vs. cancer).

The trained machine learning methods, models, and discriminate classifiers described herein may be applied toward various medical applications including cancer detection, diagnosis, and treatment responsiveness. As models may be trained with individual metadata and analyte-derived features, the applications may be tailored to stratify individuals in a population and guide treatment decisions accordingly.

Diagnosis

Methods and systems provided herein may perform predictive analytics using artificial intelligence-based approaches to analyze acquired data from a subject (or patient) to generate an output of diagnosis of the subject having a cancer. For example, the application may apply a prediction algorithm to the acquired data to generate the diagnosis of the subject having the cancer. The prediction algorithm may comprise an artificial intelligence-based predictor, such as a machine learning-based predictor, configured to process the acquired data to generate the diagnosis of the subject having the cancer.

The machine learning predictor may be trained using datasets, e.g., datasets generated by performing methylation assays using the signature panels described herein on biological samples of individuals from one or more sets of cohorts of patients having cancer as inputs and known diagnosis (e.g., staging and/or tumor fraction) outcomes of the subjects as outputs to the machine learning predictor.

Training datasets (e.g., datasets generated by performing methylation assays using the signature panels described herein on biological samples of individuals) may be generated from, for example, one or more sets of subjects having common characteristics (features) and outcomes (labels). Training datasets may comprise a set of features and labels corresponding to the features relating to diagnosis. Features may comprise characteristics such as, for example, certain ranges or categories of cfDNA assay measurements, such as counts of cfDNA fragments in a biological sample obtained from a healthy and disease samples that overlap or fall within each of a set of bins (genomic windows) of a reference genome. For example, a set of features collected from a given subject at a given time point may collectively serve as a diagnostic signature, which may be indicative of an identified cancer of the subject at the given time point. Characteristics may also include labels indicating the subject's diagnostic outcome, such as for one or more cancers.

Labels may comprise outcomes such as, for example, a known diagnosis (e.g., staging and/or tumor fraction) outcomes of the subject. Outcomes may include a characteristic associated with the cancers in the subject. For example, characteristics may be indicative of the subject having one or more cancers.

Training sets (e.g., training datasets) may be selected by random sampling of a set of data corresponding to one or more sets of subjects (e.g., retrospective and/or prospective cohorts of patients having or not having one or more cancers). Alternatively, training sets (e.g., training datasets) may be selected by proportionate sampling of a set of data corresponding to one or more sets of subjects (e.g., retrospective and/or prospective cohorts of patients having or not having one or more cancers). Training sets may be balanced across sets of data corresponding to one or more sets of subjects (e.g., patients from different clinical sites or trials). The machine learning predictor may be trained until certain predetermined conditions for accuracy or performance are satisfied, such as having minimum desired values corresponding to diagnostic accuracy measures. For example, the diagnostic accuracy measure may correspond to prediction of a diagnosis, staging, or tumor fraction of one or more cancers in the subject.

Examples of diagnostic accuracy measures may include sensitivity, specificity, positive predictive value (PPV), negative predictive value (NPV), accuracy, and area under the curve (AUC) of a Receiver Operating Characteristic (ROC) curve corresponding to the diagnostic accuracy of detecting or predicting the cancer.

In an aspect, the disclosure provides a method of using a classifier capable of distinguishing a population of individuals, comprising:

a) assaying a plurality of classes of molecules in the biological sample, wherein the assaying provides a plurality of sets of measured values representative of the plurality of classes of molecules;
b) identifying a set of features corresponding to properties of each of the plurality of classes of molecules to be analyzed using a machine learning or statistical model;
c) preparing a feature vector of feature values from each of the plurality of sets of measured values, each feature value corresponding to a feature of the set of features and including one or more measured values, wherein the feature vector comprises at least one feature value obtained using each set of the plurality of sets of measured values;
d) loading, into a memory of a computer system, the machine learning model comprising the classifier, the machine learning model trained using training vectors obtained from training biological samples, a first subset of the training biological samples identified as having a specified property and a second subset of the training biological samples identified as not having the specified property; and
e) analyzing the feature vector using the machine learning model to obtain an output classification of whether the biological sample has the specified property, thereby distinguishing a population of individuals having the specified property.

In an aspect, the disclosure provides a method of using a hierarchy capable of distinguishing a population of individuals comprising:

a) assaying a plurality of classes of molecules in the biological sample, wherein the assaying provides a plurality of sets of measured values representative of the plurality of classes of molecules;
b) identifying a set of features corresponding to properties of each of the plurality of classes of molecules to be analyzed using a machine learning or statistical model;
c) preparing a feature vector of feature values from each of the plurality of sets of measured values, each feature value corresponding to a feature of the set of features and including one or more measured values, wherein the feature vector comprises at least one feature value obtained using each set of the plurality of sets of measured values;
d) loading, into a memory of a computer system, a trained machine learning model comprising the classifier, the trained machine learning model trained using training vectors obtained from training biological samples, a first subset of the training biological samples identified as having a specified property and a second subset of the training biological samples identified as not having the specified property; and
e) applying the trained machine learning model to the feature vector to obtain an output classification of whether the biological sample has the specified property, thereby distinguishing a population of individuals having the specified property.

In an aspect, the disclosure provides a method of using a hierarchy capable of distinguishing a population of individuals, comprising:

a) detecting of methylation signals within a single sequencing read of a pre-selected genomic region in one or more first patient samples;
b) the methylation signals affect a hierarchy of data outputs to affect a machine learning model; and
c) a second patient sample using the affected hierarchy to detect methylation signals.

In some embodiments, the signature panel comprises three or more methylated genomic regions in Tables 2-17, four or more methylated genomic regions in Tables 2-17, five or more methylated genomic regions in Tables 2-17, six or more methylated genomic regions in Tables 2-17, seven or more methylated genomic regions in Tables 2-17, eight or more methylated genomic regions in Tables 2-17, nine or more methylated genomic regions in Tables 2-17, ten or more methylated genomic regions in Tables 2-17, eleven or more methylated genomic regions in Tables 2-17, twelve or more methylated genomic regions in Tables 2-17, or thirteen or more methylated genomic regions in Tables 2-17.

In another aspect, the present disclosure provides a method for identifying two or more cancers in a subject, comprising:

(a) providing a biological sample comprising cell-free nucleic acid (cfNA) molecules from said subject;
(b) methyl converting and sequencing said cfNA molecules from said subject to generate a plurality of cfNA sequencing reads;
(c) aligning said plurality of cfNA sequencing reads to a reference genome;
(d) generating a quantitative measure of said plurality of cfNA sequencing reads at each of a first plurality of genomic regions of said reference genome to generate a first cfNA feature set, wherein said first plurality of genomic regions of said reference genome comprises at least about 10 distinct regions, each of said at least about 10 distinct regions comprising at least a portion of a gene selected from the group consisting of methylated regions in the signature panels described herein; and (e) applying a trained algorithm to said first cfNA feature set to generate a likelihood of said subject having said cancer.

In some examples, said at least about 10 distinct regions comprises at least about 20 distinct regions, each of said at least about 20 distinct regions comprising at least a portion of a methylated region identified in Tables 1-17. In some examples, said at least about 10 distinct regions comprises at least about 30 distinct regions, each of said at least about 30 distinct regions comprising at least a portion of a methylated region identified in Tables 1-17.

As another example, such a predetermined condition may be that the specificity of predicting the colon cell proliferative disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the positive predictive value (PPV) of predicting the colon cell proliferative disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the negative predictive value (NPV) of predicting the colon cell proliferative disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the area under the curve (AUC) of a Receiver Operating Characteristic (ROC) curve of predicting the colon cell proliferative disorder comprises a value of at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

Treatment Responsiveness

The predictive classifiers, systems, and methods described herein may be applied toward classifying populations of individuals for a number of clinical applications (e.g., based on performing methylation assays using the signature panels described herein on biological samples of individuals). Examples of such clinical applications include detecting early-stage cancer, diagnosing cancer, classifying cancer to a particular stage of disease, and determining responsiveness or resistance to a therapeutic agent for treating cancer.

The methods and systems described herein may be applied to characteristics of a colon cell proliferative disorder, such as grade and stage. Therefore, combinations of analytes and assays may be used in the present systems and methods to predict responsiveness of cancer therapeutics across different cancer types in different tissues and classifying individuals based on treatment responsiveness. In some embodiments, the classifiers described herein are capable of stratifying a group of individuals into treatment responders and non-responders.

The present disclosure also provides a method for determining a drug target of a condition or disease of interest (e.g., genes that are relevant or important for a particular class), comprising: assessing a sample obtained from an individual for the level of gene expression for at least one gene; and using a neighborhood analysis routine, determining genes that are relevant for classification of the sample, to thereby ascertain one or more drug targets relevant to the classification.

The present disclosure also provides a method for determining the efficacy of a drug designed to treat a disease class, comprising obtaining a sample from an individual having the disease class; subjecting the sample to the drug; assessing the drug-exposed sample for the level of gene expression for at least one gene; and using a computer model built with a weighted voting scheme, classifying the drug-exposed sample into a class of the disease as a function of relative gene expression level of the sample with respect to that of the model.

The present disclosure also provides a method for determining the efficacy of a drug designed to treat a disease class, wherein an individual has been subjected to the drug, comprising obtaining a sample from the individual subjected to the drug; assessing the sample for the level of gene expression for at least one gene; and using a model built with a weighted voting scheme, classifying the sample into a class of the disease including evaluating the gene expression level of the sample as compared to gene expression level of the model.

The present disclosure also provides a method of determining whether an individual belongs to a phenotypic class (e.g., intelligence, response to a treatment, length of life, likelihood of viral infection, or obesity), comprising obtaining a sample from the individual; assessing the sample for the level of gene expression for at least one gene; and using a model built with a weighted voting scheme, classifying the sample into a class of the disease including evaluating the gene expression level of the sample as compared to gene expression level of the model.

In an aspect, the systems and methods described herein that relate to classifying a population based on treatment responsiveness refer to cancers that are treated with chemotherapeutic agents of the classes DNA damaging agents, DNA repair target therapies, inhibitors of DNA damage signaling, inhibitors of DNA damage induced cell cycle arrest and inhibition of processes indirectly leading to DNA damage, but not limited to these classes. Each of these chemotherapeutic agents may be considered a "DNA-damage therapeutic agent" as the term is used herein.

Based on a patient's analyte data, the patient may be classified into high-risk and low-risk patient groups, such as patient with a high or low risk of clinical relapse, and the results may be used to determine a course of treatment. For example, a patient determined to be a high-risk patient may be treated with adjuvant chemotherapy after surgery. For a patient deemed to be a low-risk patient, adjuvant chemotherapy may be withheld after surgery. Accordingly, the present disclosure provides, in certain aspects, a method for preparing a gene expression profile of a colon cancer tumor that is indicative of risk of recurrence.

In various examples, the classifiers described herein are capable of stratifying a population of individuals between responders and non-responders to treatment.

In another aspect, methods disclosed herein may be applied to clinical applications involving the detection or monitoring of cancer.

In some embodiments, methods disclosed herein may be applied to determine and/or predict response to treatment.

In some embodiments, methods disclosed herein may be applied to monitor and/or predict tumor load.

In some embodiments, methods disclosed herein may be applied to detect and/or predict residual tumor post-surgery.

In some embodiments, methods disclosed herein may be applied to detect and/or predict minimal residual disease post-treatment.

In some embodiments, methods disclosed herein may be applied to detect and/or predict relapse.

In an aspect, methods disclosed herein may be applied as a secondary screen.

In an aspect, methods disclosed herein may be applied as a primary screen.

In an aspect, methods disclosed herein may be applied to monitor cancer development.

In an aspect, methods disclosed herein may be applied to monitor and/or predict cancer risk.

VII. Identifying or Monitoring Cancer

After using a trained algorithm to process the dataset, at least two cancer types may be identified or monitored in the subject. The identification may be based at least in part on quantitative measures of sequence reads of the dataset at a panel of cancer-associated genomic loci (e.g., quantitative measures of RNA transcripts or DNA at the cancer-associated genomic loci).

In one embodiment, 2 or more cancer types are identified or monitored in the subject, in another embodiment, 3 or more cancer types are identified or monitored in the subject, in another embodiment, 4 or more cancer types are identified or monitored in the subject, in another embodiment, 5 or more cancer types are identified or monitored in the subject, in another embodiment, 6 or more cancer types are identified or monitored in the subject, in another embodiment, 7 or more cancer types are identified or monitored in the subject, in another embodiment, 8 or more cancer types are identified or monitored in the subject, in another embodiment, 9 or more cancer types are identified or monitored in the subject, in another embodiment, 10 or more cancer types are identified or monitored in the subject.

The cancer may be identified in the subject at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The accuracy of identifying the cancer by the trained algorithm may be calculated as the percentage of independent test samples (e.g., subjects known to have the cancer or subjects with negative clinical test results for the cancer) that are correctly identified or classified as having or not having the cancer.

The cancer may be identified in the subject with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the cancer using the trained algorithm may be calculated as the percentage of cell-free biological samples identified or classified as having the cancer that correspond to subjects that truly have the cancer.

The cancer may be identified in the subject with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the cancer using the trained algorithm may be calculated as the percentage of cell-free biological samples identified or classified as not having the cancer that correspond to subjects that truly do not have the cancer.

The cancer may be identified in the subject with a clinical sensitivity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the cancer using the trained algorithm may be calculated as the percentage of independent test samples associated with presence of the cancer (e.g., subjects known to have the cancer) that are correctly identified or classified as having the cancer.

The cancer may be identified in the subject with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the cancer using the trained algorithm may be calculated as the percentage of independent test samples associated with absence of the cancer (e.g., subjects with negative clinical test results for the cancer) that are correctly identified or classified as not having the cancer.

In some embodiments, the trained algorithm may determine that the subject is at risk of cancer of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

The trained algorithm may determine that the subject is at risk of cancer at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more.

A. Tailored Multicancer Signature Panels

In some embodiments, a multicancer detection assay biomarker panel comprises test characteristics that are selected for the different cancer types assayed in the signature panel and in subsequent analysis. In certain embodiments, the test characteristics may be ascertained from screening goals and signature panel marker selection. For example, for a first line screening test, some cancers may require greater sensitivity at a clinically acceptable specificity, while others may require very high specificity at a clinically acceptable sensitivity due to the benefits and risks of the subsequent diagnostic workup. Furthermore, performance characteristics depend on whether the test precedes, complements, or follows an accepted method of screening, or represents a new frontline screen for an otherwise unscreened cancer, either in an asymptomatic, average-risk or symptomatic, high-risk individual. For example, the impact to the patient of a false positive screen for colorectal cancer (CRC) resulting in an "unnecessary" colonoscopy is meaningfully different from a false positive screen for pancreatic or ovarian cancer that results in the "unnecessary" major abdominal surgery to confirm diagnosis. When combined with signature panel marker selection, multicancer detection biomarker panels provide methods and systems that are tailored for the screening goals, confirmatory tests, and subsequent treatment available.

Table 18 summarizes screening test characteristics for multiple cancer detection tests. In an aspect, a method is provided where the multicancer panel is tailored to provide test characteristic sensitivity and specificity for the types of cancer to be detected based on needs of cancer diagnosis and confirmatory diagnosis for two or more of the cancer types shown in Table 18 or combinations thereof.

TABLE 18

| Cancer Type | Screening Goal | Conventional Diagnostic | Multicancer Test Characteristic |
|---|---|---|---|
| CRC | Minimize false negatives; avoid unnecessary screening colonoscopies | Colonoscopy | High NPV (high sensitivity) |
| Breast | Minimize false positives; avoid unnecessary biopsies and mastectomies | Fine needle aspirate or core biopsy | High PPV (high specificity) |
| Ovarian | Minimize false positives; avoid unnecessary major abdominal surgery | Abdominal Surgery | Very High PPV (very high specificity) |
| Prostate | Minimize false positives; avoid unnecessary biopsies | Biopsy | High PPV (high specificity) |
| Lung | Minimize false positives; avoid unnecessary and expensive imaging | Imaging (X-ray, CT scan); sputum cytology; tissue biopsy | High PPV (high specificity) |
| Pancreatic | Minimize false negatives | Abdominal Surgery | Very High PPV (very high specificity) |
| Uterine | Minimize false positives; avoid unnecessary major abdominal surgery | Abdominal Surgery | Very High PPV (very high specificity) |
| Liver | Minimize false negatives | Imaging and Biopsy | High NPV (high sensitivity) |
| Esophagus | Minimize false negatives; accurately stage cancer to select appropriate treatment | Biopsy | High NPV (high sensitivity) |
| Stomach | Minimize false negatives | Endoscopic biopsy | High NPV (high sensitivity) |
| Thyroid | Minimize false positives; avoid unnecessary biopsies | fine-needle aspiration | High PPV (high specificity) |
| Bladder | Minimize false negatives | cystoscopy | High NPV (high sensitivity) |

In one embodiment, the multicancer test comprises markers for detecting pancreatic, uterine, or ovarian cancer, and has a specificity at least 80%, at least 85%, at least 90%, at least 95%, at least 99%.

In one embodiment, the multicancer test comprises markers for detecting colorectal, liver, esophagus, or bladder cancer, and has a sensitivity of at least 50%, at least 60%, at least 70%, at least 80%, at least 90%, at least 95%.

In one embodiment, the multicancer test comprises markers for detecting breast, prostate, lung, or thyroid cancer, and has a specificity of at least 50%, at least 60%, at least 70%, at least 80%, at least 90%, at least 95%.

Upon identifying the subject as having a cancer type, the subject may be optionally provided with a therapeutic intervention (e.g., prescribing an appropriate course of treatment to treat the cancer of the subject). The therapeutic intervention may comprise a prescription of an effective dose of a drug, a further testing or evaluation of the cancer, a further monitoring of the cancer, or a combination thereof. If the subject is currently being treated for the cancer with a course of treatment, the therapeutic intervention may comprise a subsequent different course of treatment (e.g., to increase treatment efficacy due to non-efficacy of the current course of treatment).

The therapeutic intervention may comprise recommending the subject for a secondary clinical test to confirm a diagnosis of the cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

The quantitative measures of sequence reads of the dataset at the panel of cancer-associated genomic loci (e.g., quantitative measures of RNA transcripts or DNA at the colorectal cancer-associated genomic loci) may be assessed over a duration of time to monitor a patient (e.g., subject who has cancer or who is being treated for cancer). In such cases, the quantitative measures of the dataset of the patient may change during the course of treatment. For example, the quantitative measures of the dataset of a patient with decreasing risk of the cancer due to an effective treatment may shift toward the profile or distribution of a healthy subject (e.g., a subject without cancer). Conversely, for example, the quantitative measures of the dataset of a patient with increasing risk of the cancer due to an ineffective treatment may shift toward the profile or distribution of a subject with higher risk of the cancer or a more advanced cancer.

The cancer of the subject may be monitored by monitoring a course of treatment for treating the cancer of the subject. The monitoring may comprise assessing the cancer of the subject at two or more time points. The assessing may be based at least on the quantitative measures of sequence reads of the dataset at a panel of cancer-associated genomic loci (e.g., quantitative measures of RNA transcripts or DNA at the cancer-associated genomic loci) comprising quantitative measures of a panel of cancer-associated genomic loci determined at each of the two or more time points.

In some embodiments, a difference in the quantitative measures of sequence reads of the dataset at a panel of cancer-associated genomic loci (e.g., quantitative measures of RNA transcripts or DNA at the cancer-associated genomic loci) comprising quantitative measures of a panel of cancer-associated genomic loci determined between the two or more time points may be indicative of one or more clinical indications, such as (i) a diagnosis of the cancer of the subject; (ii) a prognosis of the cancer of the subject; (iii) an increased risk of the cancer of the subject; (iv) a decreased risk of the cancer of the subject; (v) an efficacy of the course of treatment for treating the cancer of the subject; and (vi) a non-efficacy of the course of treatment for treating the cancer of the subject.

In some embodiments, a difference in the quantitative measures of sequence reads of the dataset at a panel of cancer-associated genomic loci (e.g., quantitative measures of RNA transcripts or DNA at the cancer-associated genomic loci) comprising quantitative measures of a panel of cancer-associated genomic loci determined between the two or more time points may be indicative of a diagnosis of the cancer of the subject. For example, if the cancer was not detected in the subject at an earlier time point but was detected in the subject at a later time point, then the difference is indicative of a diagnosis of the cancer of the subject. A clinical action or decision may be made based on this indication of diagnosis of the cancer of the subject, such as, for example, prescribing a new therapeutic intervention for the subject. The clinical action or decision may comprise recommending the subject for a secondary clinical test to confirm the diagnosis of the cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

In some embodiments, a difference in the quantitative measures of sequence reads of the dataset at a panel of cancer-associated genomic loci (e.g., quantitative measures of RNA transcripts or DNA at the cancer-associated genomic loci) comprising quantitative measures of a panel of cancer-associated genomic loci determined between the two or more time points may be indicative of a prognosis of the cancer of the subject.

In some embodiments, a difference in the quantitative measures of sequence reads of the dataset at a panel of cancer-associated genomic loci (e.g., quantitative measures of RNA transcripts or DNA at the cancer-associated genomic loci) comprising quantitative measures of a panel of cancer-associated genomic loci determined between the two or more time points may be indicative of the subject having an increased risk of the cancer. For example, if the colorectal cancer was detected in the subject both at an earlier time point and at a later time point, and if the difference is a positive difference (e.g., the quantitative measures of sequence reads of the dataset at a panel of cancer-associated genomic loci (e.g., quantitative measures of RNA transcripts or DNA at the cancer-associated genomic loci) increased from the earlier time point to the later time point), then the difference may be indicative of the subject having an increased risk of the cancer. A clinical action or decision may be made based on this indication of the increased risk of the cancer, e.g., prescribing a new therapeutic intervention or switching therapeutic interventions (e.g., ending a current treatment and prescribing a new treatment) for the subject. The clinical action or decision may comprise recommending the subject for a secondary clinical test to confirm the increased risk of the cancer. This secondary clinical test may comprise an imaging test, a blood test, a computed tomography (CT) scan, a magnetic resonance imaging (MM) scan, an ultrasound scan, a chest X-ray, a positron emission tomography (PET) scan, a PET-CT scan, a cell-free biological cytology, a FIT test, an FOBT test, or any combination thereof.

In some embodiments, a difference in the quantitative measures of sequence reads of the dataset at a panel of cancer-associated genomic loci (e.g., quantitative measures of RNA transcripts or DNA at the colorectal cancer-associated genomic loci) comprising quantitative measures of a panel of cancer-associated genomic loci determined between the two or more time points may be indicative of the subject having a decreased risk of the cancer. For example, if the cancer was detected in the subject both at an earlier time point and at a later time point, and if the difference is a negative difference (e.g., the quantitative measures of sequence reads of the dataset at a panel of cancer-associated genomic loci (e.g., quantitative measures of RNA transcripts or DNA at the colorectal cancer-associated genomic loci) comprising quantitative measures of a panel of cancer-associated genomic loci decreased from the earlier time point to the later time point), then the difference may be indicative of the subject having a decreased risk of the colorectal cancer. A clinical action or decision may be made based on this indication of the decreased risk of the cancer (e.g., continuing or ending a current therapeutic intervention) for the subject. The clinical action or decision may comprise recommending the subject for a secondary clinical test to confirm the decreased risk of the colorectal cancer. This secondary clinical test may comprise an imaging test, a blood test, a computed tomography (CT) scan, a magnetic resonance imaging (MM) scan, an ultrasound scan, a chest X-ray, a positron emission tomography (PET) scan, a PET-CT scan, a cell-free biological cytology, a FIT test, an FOBT test, or any combination thereof.

In some embodiments, a difference in the quantitative measures of sequence reads of the dataset at a panel of cancer-associated genomic loci (e.g., quantitative measures of RNA transcripts or DNA at the cancer-associated genomic loci) comprising quantitative measures of a panel of cancer-associated genomic loci determined between the two or more time points may be indicative of an efficacy of the course of treatment for treating the cancer of the subject. For example, if the cancer was detected in the subject at an earlier time point but was not detected in the subject at a later time point, then the difference may be indicative of an efficacy of the course of treatment for treating the cancer of the subject. A clinical action or decision may be made based on this indication of the efficacy of the course of treatment for treating the cancer of the subject, e.g., continuing or ending a current therapeutic intervention for the subject. The clinical action or decision may comprise recommending the subject for a secondary clinical test to confirm the efficacy of the course of treatment for treating the cancer. This secondary clinical test may comprise an imaging test, a blood test, a computed tomography (CT) scan, a magnetic resonance imaging (MM) scan, an ultrasound scan, a chest X-ray, a positron emission tomography (PET) scan, a PET-CT scan, a cell-free biological cytology, a FIT test, an FOBT test, or any combination thereof.

In some embodiments, a difference in the quantitative measures of sequence reads of the dataset at a panel of cancer-associated genomic loci (e.g., quantitative measures of RNA transcripts or DNA at the cancer-associated genomic loci) comprising quantitative measures of a panel of cancer-associated genomic loci determined between the two or more time points may be indicative of a non-efficacy of the course of treatment for treating the cancer of the subject. For example, if the cancer was detected in the subject both at an earlier time point and at a later time point, and if the difference is a positive or zero difference (e.g., the quantitative measures of sequence reads of the dataset at a panel of cancer-associated genomic loci (e.g., quantitative measures of RNA transcripts or DNA at the cancer-associated genomic loci) comprising quantitative measures of a panel of cancer-associated genomic loci increased or remained at a constant level from the earlier time point to the later time point), and if an efficacious treatment was indicated at an earlier time point, then the difference may be indicative of a non-efficacy of the course of treatment for treating the cancer of the subject. A clinical action or decision may be made based on this indication of the non-efficacy of the course of treatment for treating the cancer of the subject, e.g., ending a current therapeutic intervention and/or switching to (e.g., prescribing) a different new therapeutic intervention for the subject. The clinical action or decision may comprise recommending the subject for a secondary clinical test to confirm the non-efficacy of the course of treatment for treating the cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

VIII. Kits

The present disclosure provides kits for identifying or monitoring two or more cancer types in a subject. A kit may comprise probes for identifying a quantitative measure (e.g., indicative of a presence, absence, or relative amount) of sequences at each of a plurality of cancer-associated genomic loci in a cell-free biological sample of the subject. A quantitative measure (e.g., indicative of a presence, absence, or relative amount) of sequences at each of a plurality of cancer-associated genomic loci in the cell-free biological sample may be indicative of one or more cancers. The probes may be selective for the sequences at the plurality of cancer-associated genomic loci in the cell-free biological sample. A kit may comprise instructions for using the probes to process the cell-free biological sample to generate datasets indicative of a quantitative measure (e.g., indicative of a presence, absence, or relative amount) of sequences at each of the plurality of cancer-associated genomic loci in a cell-free biological sample of the subject.

The probes in the kit may be selective for the sequences at the plurality of cancer-associated genomic loci in the cell-free biological sample. The probes in the kit may be configured to selectively enrich nucleic acid (e.g., RNA or DNA) molecules corresponding to the plurality of cancer-associated genomic loci. The probes in the kit may be nucleic acid primers. The probes in the kit may have sequence complementarity with nucleic acid sequences from one or more of the plurality of cancer-associated genomic loci or genomic regions. The plurality of cancer-associated genomic loci or genomic regions may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, or more distinct cancer-associated genomic loci or genomic regions. The plurality of cancer-associated genomic loci or genomic regions may comprise one or more members selected from the group consisting of regions listed in Tables 1-17.

The instructions in the kit may comprise instructions to assay the cell-free biological sample using the probes that are selective for the sequences at the plurality of cancer-associated genomic loci in the cell-free biological sample. These probes may be nucleic acid molecules (e.g., RNA or DNA) having sequence complementarity with nucleic acid sequences (e.g., RNA or DNA) from one or more of the plurality of cancer-associated genomic loci. These nucleic acid molecules may be primers or enrichment sequences. The instructions to assay the cell-free biological sample may comprise introductions to perform array hybridization, polymerase chain reaction (PCR), or nucleic acid sequencing (e.g., DNA sequencing or RNA sequencing) to process the cell-free biological sample to generate datasets indicative of a quantitative measure (e.g., indicative of a presence, absence, or relative amount) of sequences at each of the plurality of cancer-associated genomic loci in the cell-free biological sample. A quantitative measure (e.g., indicative of a presence, absence, or relative amount) of sequences at each of a plurality of cancer-associated genomic loci in the cell-free biological sample may be indicative of one or more cancers.

The instructions in the kit may comprise instructions to measure and interpret assay readouts, which may be quantified at one or more of the plurality of cancer-associated genomic loci to generate the datasets indicative of a quantitative measure (e.g., indicative of a presence, absence, or relative amount) of sequences at each of the plurality of cancer-associated genomic loci in the cell-free biological sample. For example, quantification of array hybridization or polymerase chain reaction (PCR) corresponding to the plurality of cancer-associated genomic loci may generate the datasets indicative of a quantitative measure (e.g., indicative of a presence, absence, or relative amount) of sequences at each of the plurality of cancer-associated genomic loci in the cell-free biological sample. Assay readouts may comprise quantitative PCR (qPCR) values, digital PCR (dPCR) values, digital droplet PCR (ddPCR) values, fluorescence values, or normalized values thereof.

EXAMPLES

Example 1: Selection of Methylated Regions for Detection of Multiple Cancer Types To design a signature panel capable of detecting and distinguishing multiple types of cancers, regions of cfDNA that are methylated in various types of cancers and capable of being used to determine tissue of origin of a cancer type (tumor or cancerous cells) were identified. Two principles were used for designing a multi-cancer signature panel of methylated regions of DNA:

(i) identification of regions useful for screening for different cancer types including regions that may considered "pan-cancer" and methylated in more than one type of cancer; and (ii) identification of regions useful for determining the tissue of origin of the tumor (TOO) including regions that are methylated or hypermethylated only in one cancer of interest and not in other cancer types or in subjects not having any cancer.

TCGA and EPIC Array Data Analysis

TCGA 450K array data were used for analysis. 450K methylation array raw idat files for 33 cancer types (including cancer and normal tissue data) were downloaded from the TCGA website. Beta values for each probe were calculated using the R package SeSAMe. Each region in the CpG dense light panel (CpGdv2) was assigned the average beta value of all probes overlapping the region. Table 19 shows the number of cancer and normal tissue data obtained.

TABLE 19

| Symbol | Cancer type | # Cancer | # Normal | # Total |
|---|---|---|---|---|
| COAD | Colon adenocarcinoma | 314 | 39 | 353 |
| LIHC | Liver hepatocellular carcinoma | 380 | 50 | 430 |
| LUAD | Lung adenocarcinoma | 475 | 32 | 507 |
| LUSC | Lung squamous cell carcinoma | 370 | 42 | 412 |
| OV | Ovarian serous cystadenocarcinoma | 10 | 0 | 10 |
| PAAD | Pancreatic adenocarcinoma | 185 | 10 | 195 |
| PRAD | Prostate adenocarcinoma | 503 | 50 | 553 |
| READ | Rectum adenocarcinoma | 99 | 7 | 106 |

Public blood EPIC array data used for analysis was downloaded from GEO (Blood, GSE110555, 67 samples). The public blood data was generated on the EPIC array, so only probes that overlapped the TCGA 450K array data were used. Each region in the CpG dense light panel was assigned a beta value similar to the procedure described above for the TCGA data.

Univariate Analysis

Univariate AUCs for each region in the CpG dense light panel were calculated for cancer vs. normal tissue (for all cancers that had normal tissue data), and cancer vs. blood (for all cancers). Regions that had univariate AUC≥0.9 for both the cancer vs. blood and cancer vs. normal tissue comparison were kept for downstream analyses. This resulted in a total of 3840 regions, adding up to 6349802 bp in size.

Metilene Analysis

Metilene analysis was performed on 450K methylation array tissue data from the TCGA, excluding data from non-cancer samples. Probe beta values that had been normalized using the OpenSesame R pipeline were used. Differentially methylated regions (DMRs) were retained that had a q-value of 0.05 or less. The overlap of these regions with the CpG Dense panel were examined. Each CpG Dense region was annotated as detected by Metilene or not detected in each tissue type. This information was used to identify regions that were detected in a single tissue and could be used for tissue of origin detection vs. multiple tissues. This resulted in a total of 3498 regions, adding up to 4276029 bp in size.

Overlap Between the Univariate Analysis and Metilene Analysis

~2.2 Mb (1681 regions) overlapped between the univariate and metilene analysis. These regions were further used for downstream analysis and filtered based on overlap with the regions from the HMFC analysis of tissue TEM-seq data described later.

Figure 2:
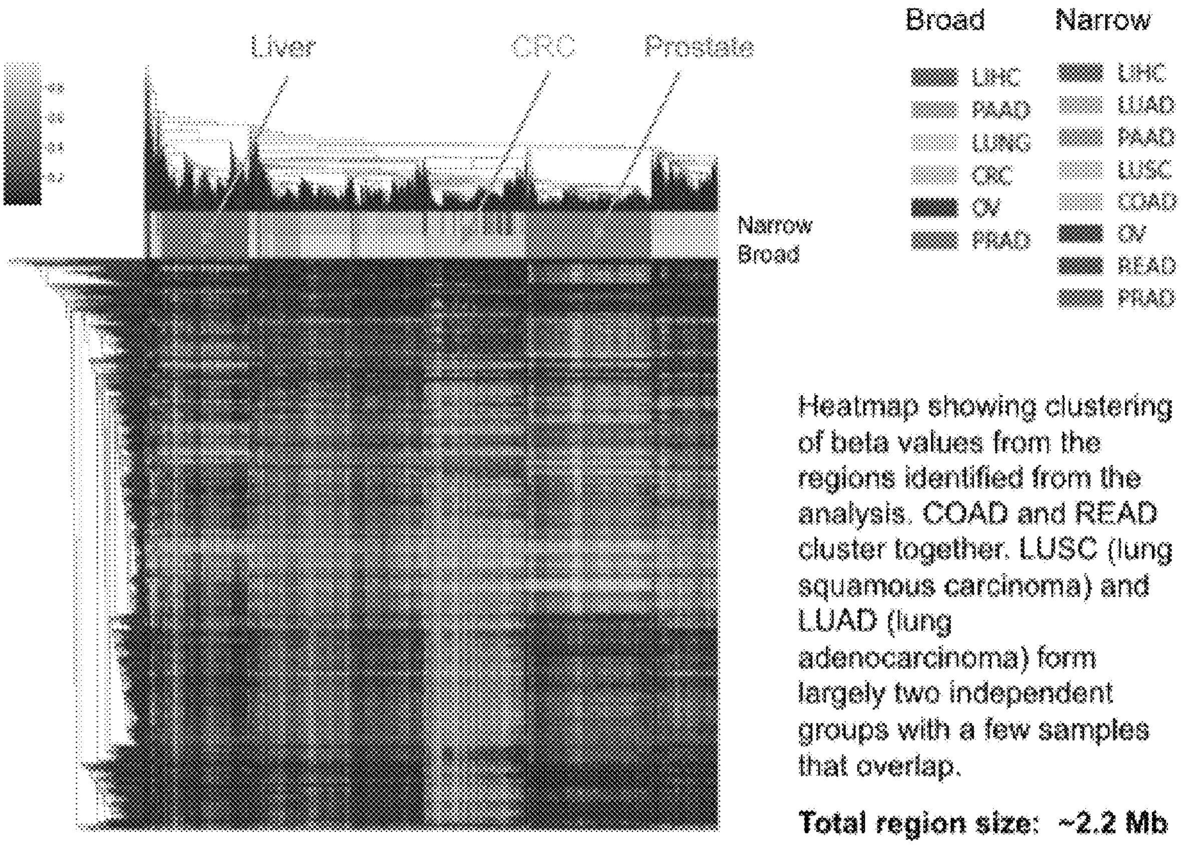
FIG. 2 provides a heatmap of beta values of these 1681 regions that indicates that these regions may contain useful signal for determining tumor of origin as well. Different tumor types cluster into largely distinct groups.

FIG. 2 provides a heatmap of beta values of these 1681 regions that indicates that these regions may contain useful signal for determining tumor of origin as well. Different tumor types cluster into largely distinct groups. The heatmap shows clustering of beta values from the regions identified from the analysis. Colon adenocarcinoma (COAD) and Rectal adenocarcinoma (READ) clustered together. Lung squamous carcinoma (LUSC) and Lung adenocarcinoma (LUAD) formed largely two independent groups with a few samples that overlap. Total region size in this analysis was ~2.2 Mb.

Identifying Tissue of Origin Regions from TCGA Analysis

For the 1681 regions from the TCGA analysis that overlapped the univariate and metilene analysis, a putative list of TOOs was defined having DMRs in only one cancer type. These regions were verified by performing univariate analysis for one vs. every other cancer type, and keeping regions that are concordant for tissue type between the metilene and univariate analysis. Regions which had a univariate AUC≥0.75 for the cancer were considered DMRs, whereas <0.65 AUC for every other cancer type were kept for the final putative TOO list from the TCGA analysis. This analysis resulted in 79 regions with a total size of 103,554 bp.

Analysis of Tissue Methyl-seq Data

Data

FF (flash frozen) tissue retrospective samples were obtained. DNA isolated therefrom was sequenced with methylation-sequence methods. Table 20 shows the number of samples for each tissue sample obtained.

TABLE 20

| Tissue | # Samples |
|---|---|
| CRC | 63 |
| Liver | 14 |
| Lung | 24 (in duplicate) |
| Ovarian | 22 |
| Pancreatic | 29 |
| Prostate | 29 |
| Healthy plasma | 96 |

Autosegmentation

A modified version of the auto-segmentation pipeline was used to define reasonable region boundaries for each cancer type. Filtered and unfiltered bam files were created for each cancer type. Pickle files were created and input into a modified autosegmentation pipeline to identify regions that have methylation in cancer samples but little to no methylation in the healthy plasma samples.

Hypermethylated Fragment Analysis in Cancer Vs. Plasma Models for Feature Selection Hypermethylated fragment analysis was used and summarized over the segmented regions for each cancer. To identify top features, hypermethylated fragment analysis was performed for cancer vs. plasma models using 5-fold CV with 5 reshuffles, keeping regions that were selected in at least 1-fold and have a mean effect size >$90^{th}$ percentile. This resulted in 845 regions with a total region size of 643185 bp.

Hypermethylated Fragment Analysis in Cancer Vs. Every Other Cancer Model for Putative TOO Feature Selection For each cancer type, regions that are hypermethylated in a cancer of interest but not in any other cancers were identified. To achieve this, hypermethylated fragment analysis was used, keeping regions selected in all 25-folds and a mean effect size the lesser of $100^{th}$ or the $99^{th}$ percentile value. This resulted in a total of 141 regions with a total size of 86,129 bp.

Final Multi-Cancer Panel Design Procedure

Regions from the TCGA univariate analysis that overlapped both the metilene differentially methylated region analysis and methylated fragment tissue methyl-seq analysis were combined with the putative TOO regions identified either from the TCGA or methyl-seq tissue data analysis to obtain a multi-cancer signature panel. This resulted in a total of 417 methylated regions with a total size of 512,123 bp.

Figure 3:
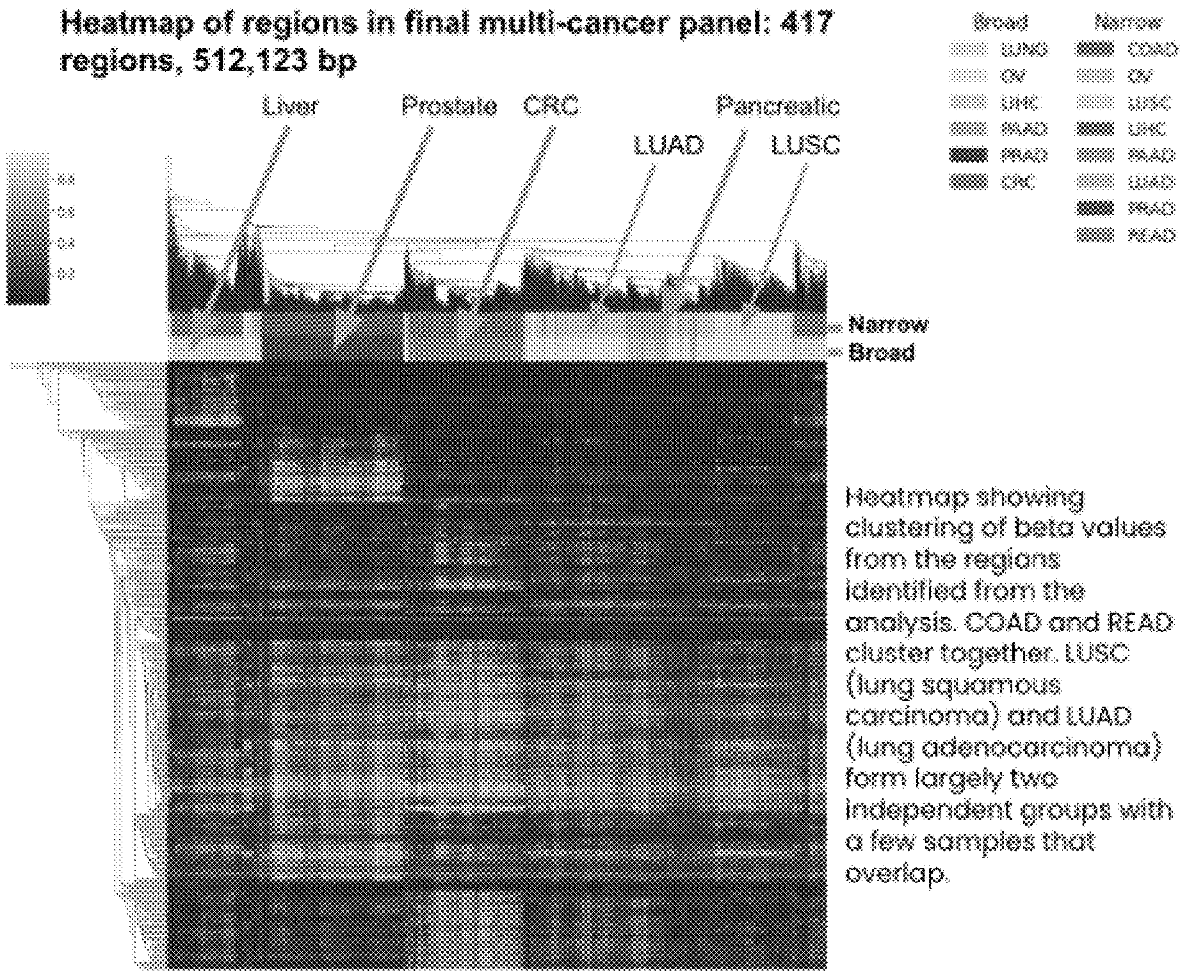
FIG. 3 provides a heatmap of the regions included in the multi-cancer panel. The heatmap shows that even with this smaller subset, there is appropriate separation between the different cancer types.

FIG. 3 shows a heatmap of the regions included in the multi-cancer panel. The heatmap shows distinct separation between the different cancer types even with this smaller subset. The heatmap shows clustering of beta values from the regions identified from the analysis. Colon adenocarcinoma (COAD) and Rectal adenocarcinoma (READ) clustered together. Lung squamous carcinoma (LUSC) and Lung adenocarcinoma (LUAD) formed largely two independent groups with a few samples that overlapped.

What is claimed is:

1. A method of treating a colorectal cancer in a subject using a computer specifically programmed to detect the colorectal cancer, the method comprising:

(a) converting unmethylated cytosines to uracils in a nucleic acid sample obtained or derived from the subject to provide a plurality of converted nucleic acids;

(b) amplifying the plurality of converted nucleic acids with polymerase chain reaction to provide amplified nucleic acids;

(c) contacting the amplified nucleic acids with nucleic acid probes, wherein each of the nucleic acid probes is complementary to a genomic region of a set of genomic regions, wherein each genomic region of the set of genomic regions comprises a genomic region starting position and a genomic region stopping position as set forth in Tables 1-4, wherein each genomic region of the set of genomic regions is differentially methylated in a population of subjects having the colorectal cancer, to provide enriched nucleic acids, wherein Tables 1-4 are given by:

TABLE 1

| Closest Gene | Chromosome Number | Genomic Region Starting Position | Genomic Region Stopping Position |
|---|---|---|---|
| CRIPAK, UVSSA | chr4 | 1410251 | 1411075 |
| MEOX2 | chr7 | 15685300 | 15688105 |
| LRRN2 | chr1 | 204684180 | 204685942 |
| ZNF177 | chr19 | 9362913 | 9363600 |
| DPYSL2 | chr8 | 26578930 | 26579269 |
| CPNE5 | chr6 | 36839707 | 36841032 |
| PHOX2B | chr4 | 41744645 | 41745232 |
| GLB1L3 | chr11 | 134275700 | 134278165 |
| GRIN2A | chr16 | 10181849 | 10183617 |
| SERPINE2 | chr2 | 224038504 | 224040310 |
| LRRC41 | chr1 | 46302590 | 46304060 |
| TMEM101 | chr17 | 44014457 | 44015264 |
| LRRC41 | chr1 | 46301753 | 46301753 |
| TFAP2E | chr1 | 35576535 | 35578237 |
| ZNF154 | chr19 | 57708612 | 57709440 |
| IRF2BP1 | chr19 | 45876550 | 45877420 |
| LYPLAL1-DT | chr1 | 219173767 | 219174230 |
| SCRG1 | chr4 | 173508370 | 173510040 |
| PDXK | chr21 | 43728573 | 43729711 |
| LOC100286906 | chr7 | 155371315 | 155374020 |
| HOPX | chr4 | 56655120 | 56656970 |
| ITGA4 | chr2 | 181456459 | 181458643 |
| PPP1R16B | chr20 | 38804789 | 38807565 |
| HOXAI | chr7 | 27095185 | 27097167 |
| TCE24 | chr8 | 66961153 | 66963484 |
| LOC100130992 | chr10 | 22252193 | 22254000 |
| LOC100286906 | chr7 | 155371315 | 155374020 |
| EMILIN2 | chr18 | 2847184 | 2848342 |
| IRF4 | chr6 | 391101 | 392638 |
| OR1F2P | chr16 | 3187792 | 3189855 |
| MOB3B | chr9 | 27528978 | 27529887 |
| IRF2BP1 | chr19 | 45876550 | 45877420 |
| AKRIB1 | chr7 | 134458200 | 134459533 |
| KLK10 | chr19 | 51018748 | 51020133 |
| ZSCANI12 | chr6 | 28399347 | 28400210 |
| RNVUI1-8 | chr1 | 147083835 | 147085351 |
| PPP1R16B | chr20 | 38804789 | 38807565 |
| LOC100130298 | chr8 | 60909799 | 60910469 |
| LOC100507557 | chr6 | 145814298 | 145815785 |
| UBXN10 | chr1 | 20185867 | 20186730 |
| ZNF625 | chr19 | 12155907 | 12156871 |
| LOC392232 | chr8 | 72251140 | 72251956 |
| BASP1-AS1 | chr5 | 17217516 | 17219975 |
| LINC01264 | chr10 | 42932936 | 42933788 |
| KIF7 | chr15 | 89654755 | 89655920 |
| TWIST1 | chr7 | 19112343 | 19112657 |
| SNORD12 | chr20 | 49318252 | 49319561 |
| ARHGEF16 | chr1 | 3393377 | 3394370 |
| SLCO3A1 | chr15 | 91852783 | 91854800 |
| TBX18 | chr6 | 84762839 | 84765672 |
| GTDC1 | chr2 | 143936690 | 143937919 |
| SHISA3 | chr4 | 42397040 | 423998745 |
| AKRIB1 | chr7 | 134458200 | 134459533 |
| HOXA1 | chr7 | 27095185 | 27097167 |
| SPAG6 | chr10 | 22334421 | 22337305 |
| IRF4 | chr6 | 391101 | 392638 |
| PRKCB | chr16 | 23835195 | 23837445 |
| PFKP | chr10 | 3066025 | 3067776 |
| FLT3 | chr13 | 28099335 | 28101240 |

TABLE 2

| Closest Gene | Chromosome Number | Genomic Region Starting Position | Genomic Region Stopping Position |
|---|---|---|---|
| GPC6 | chr13 | 93226527 | 93229026 |
| PLCB1 | chr20 | 8131515 | 8134057 |
| PNPLA5 | chr22 | 43890585 | 43892865 |
| NDUFA5P12 | chr8 | 47188540 | 47189584 |
| GRAMD1B | chr11 | 123357785 | 123358764 |

TABLE 2-continued

| Closest Gene | Chromosome Number | Genomic Region Starting Position | Genomic Region Stopping Position |
|---|---|---|---|
| RNU4-5P | chr10 | 109456465 | 109457325 |
| LRFN3 | chr19 | 35958969 | 35960233 |
| ABHD17AP6 | chr17 | 20852130 | 20853135 |
| GAMT | chr19 | 1400250 | 1401892 |
| WNT2 | chr7 | 117322020 | 117324934 |

TABLE 3

| Closest Gene | Chromosome Number | Genomic Region Starting Position | Genomic Region Stopping Position |
|---|---|---|---|
| SLC9A3-AS1 | chr5 | 474858 | 475204 |
| DKK2 | chr4 | 107034039 | 107034696 |
| LOX | chr5 | 122076761 | 122077388 |
| C1QL3 | chr10 | 16521666 | 16521939 |
| CSPG5 | chr3 | 47578577 | 47579390 |
| CCT6B | chr17 | 34961183 | 34962104 |
| ISL2 | chr15 | 76336381 | 76336866 |
| ZSWIM2 | chr2 | 186849081 | 186849342 |
| LINC00599 | chr8 | 9904982 | 9906090 |
| LINC01517 | chr10 | 28722124 | 28722695 |

TABLE 4

| Closest Gene | Chromosome Number | Genomic Region Starting Position | Genomic Region Stopping Position |
|---|---|---|---|
| CRIPAK, UVSSA | chr4 | 1410251 | 1411075 |
| MEOX2 | chr7 | 15685300 | 15688105 |
| LRRN2 | chrl | 204684180 | 204685942 |
| ZNF177 | chr19 | 9362913 | 9363600 |
| DPYSL2 | chr8 | 26578930 | 26579269 |
| CPNE5 | chr6 | 36839707 | 36841032 |
| PHOX2B | chr4 | 41744645 | 41745232 |
| CLB1L3 | chr11 | 134275700 | 134278165 |
| GRIN2A | chr16 | 10181849 | 10183617 |
| SERPINE2 | chr2 | 224038504 | 224040310 |

(d) sequencing the enriched nucleic acids or derivatives thereof to produce sequence reads;

(e) analyzing the sequence reads, wherein the analyzing comprises applying a trained machine learning model to the sequence reads to generate an output value, wherein the trained machine learning model was trained on the set of genomic regions with training data comprising: (i) a first set of differentially methylated nucleic acid sample data obtained or derived from subjects with the colorectal cancer, and (ii) a second set of differentially methylated nucleic acid sample data obtained or derived from subjects without the colorectal cancer;

(f) processing the output value to a predetermined threshold value associated with a presence of the colorectal cancer and determining the presence of the colorectal cancer in the subject, thereby detecting the colorectal cancer in the subject; and (g) responsive to the detecting in (f), administering to the subject a chemotherapy, a radiotherapy, or an immunotherapy, or performing a surgery, or a combination thereof, on the subject, thereby treating the colorectal cancer in the subject.

2. The method of claim 1, wherein the nucleic acid sample is a cell-free nucleic acid sample.

3. The method of claim 2, wherein the cell-free nucleic acid sample is a cell-free deoxyribonucleic acid (DNA) sample.

4. The method of claim 1, wherein the nucleic acid sample is selected from the group consisting of a body fluid, stool, colonic effluent, urine, blood plasma, blood serum, whole blood, isolated blood cells, cells isolated from the blood, and combinations thereof.

5. The method of claim 1, wherein each of the nucleic acid probes is complementary to six or more genomic regions from a starting position to a stopping position selected from Table 1, wherein the six or more genomic regions are differentially methylated in a population of subjects having the colorectal cancer.

6. The method of claim 1, wherein each of the nucleic acid probes is complementary to at least three genomic regions from a starting position to a stopping position selected from Table 2, at least three genomic regions from a starting position to a stopping position selected from Table 3, or at least three genomic regions from a starting position to a stopping position selected from Table 4.

7. The method of claim 1, wherein the genomic region is selected from the group consisting of differentially methylated genomic regions from a starting position to a stopping position in Table 2, 3, or 4, and is associated with a colorectal cancer tissue of origin.

* * * * *